United States Patent
Seshimo et al.

(10) Patent No.: US 8,124,313 B2
(45) Date of Patent: Feb. 28, 2012

(54) RESIST COMPOSITION, METHOD OF FORMING RESIST PATTERN, NOVEL COMPOUND, AND ACID GENERATOR

(75) Inventors: Takehiro Seshimo, Kawasaki (JP); Yoshiyuki Utsumi, Kawasaki (JP); Akiya Kawaue, Kawasaki (JP); Hideo Hada, Kawasaki (JP); Hiroaki Shimizu, Kawasaki (JP); Tsuyoshi Nakamura, Kawasaki (JP)

(73) Assignee: Tokyo Ohka Kogyo Co., Ltd., Kawaski-shi (JP)

( * ) Notice: Subject to any disclaimer, the term of this patent is extended or adjusted under 35 U.S.C. 154(b) by 162 days.

(21) Appl. No.: 12/692,513

(22) Filed: Jan. 22, 2010

(65) Prior Publication Data

US 2010/0121077 A1 May 13, 2010

Related U.S. Application Data

(63) Continuation of application No. 12/265,607, filed on Nov. 5, 2008, now Pat. No. 7,682,772.

(30) Foreign Application Priority Data

Nov. 19, 2007 (JP) ................. 2007-299527
Mar. 21, 2008 (JP) ................. 2008-074466
Sep. 25, 2008 (JP) ................. 2008-246643

(51) Int. Cl.
*G03F 7/004* (2006.01)
*C07D 327/02* (2006.01)

(52) U.S. Cl. ............. 430/270.1; 430/921; 430/922; 549/10; 562/100; 562/109; 562/115

(58) Field of Classification Search ........... 430/270.1, 430/921, 922; 549/10; 562/100, 109, 115
See application file for complete search history.

(56) References Cited

U.S. PATENT DOCUMENTS 5,945,517 A  8/1999 Nitta et al.
(Continued)

FOREIGN PATENT DOCUMENTS

EP  1 600 437 A  11/2005
(Continued)

OTHER PUBLICATIONS

Supplemental European Search Report issued for counterpart European Patent Application No. 08168403.7, dated Mar. 3, 2009.
(Continued)

*Primary Examiner* — John Chu
(74) *Attorney, Agent, or Firm* — Knobbe Martens Olson & Bear LLP

(57) ABSTRACT

A compound represented by general formula (I); and a compound represented by general formula (b1-1).

[Chemical Formula 1]

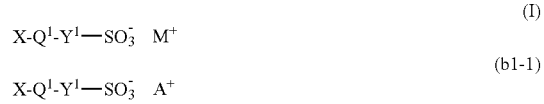

wherein $Q^1$ represents a divalent linkage group or a single bond; $Y^1$ represents an alkylene group which may have a substituent or a fluorinated alkylene group which may have a substituent; X represents a cyclic group of 3 to 30 carbon atoms which may have a substituent, and has an —$SO_2$— bond in the structure thereof; $M^+$ represents an alkali metal ion; and $A^+$ represents an organic cation.

19 Claims, No Drawings

U.S. PATENT DOCUMENTS

| | | | |
|---|---|---|---|
| 6,153,733 A | 11/2000 | Yukawa et al. | |
| 7,323,287 B2 | 1/2008 | Iwai et al. | |
| 7,682,772 B2 * | 3/2010 | Seshimo et al. | 430/270.1 |
| 2003/0113658 A1 | 6/2003 | Ebata et al. | |
| 2007/0078269 A1 | 4/2007 | Harada et al. | |
| 2007/0100158 A1 | 5/2007 | Harada et al. | |
| 2007/0100159 A1 | 5/2007 | Yoshida et al. | |

FOREIGN PATENT DOCUMENTS

| | | |
|---|---|---|
| GB | 1 431 251 A | 4/1976 |
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-241385 | 8/2003 |
| JP | A 2007-145823 | 6/2007 |
| JP | A 2007-145824 | 6/2007 |
| WO | WO 2004-074242 | 9/2004 |

OTHER PUBLICATIONS

Date-stamped correspondence acknowledging receipt of search report by Applicant, dated Mar. 23, 2009.

Office Action (Notice of Allowance) issued in counterpart Korean Patent Application No. 10-2008-0113890, dated Feb. 23, 2011.

* cited by examiner

RESIST COMPOSITION, METHOD OF FORMING RESIST PATTERN, NOVEL COMPOUND, AND ACID GENERATOR

RELATED APPLICATIONS

This application is a continuation of application Ser. No. 12/265,607, filed Nov. 5, 2008, which claims priority under 35 U.S.C. §119 to Japanese Patent Application No. 2007-299527, filed Nov. 19, 2007, Japanese Patent Application No. 2008-74466, filed Mar. 21, 2008, and Japanese Patent Application No. 2008-246643, filed Sep. 25, 2008, the contents of which are incorporated herein by reference.

TECHNICAL FIELD

The present invention relates to a resist composition, a method of forming a resist pattern, a novel compound useful as an acid generator for the resist composition, a compound useful as a precursor of the compound, and an acid generator.

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under action of acid and an acid generator that generates acid upon exposure. For example, a chemically amplified positive resist contains, as a base resin, a resin which exhibits increased solubility in an alkali developing solution under action of acid, and an acid generator. In the formation of a resist pattern, when acid is generated from the acid generator upon exposure, the exposed portions become soluble in an alkali developing solution.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm.

As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl (meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

As acid generators usable in a chemically amplified resist, various types have been proposed including, for example, onium salt-based acid generators such as iodonium salts and sulfonium salts.

[Patent Document 1] Japanese Unexamined Patent Application, First Publication No. 2003-241385

DISCLOSURE OF INVENTION

Problems to Be Solved By the Invention

Currently, as the anion moiety for the aforementioned onium salt-based acid generators, a perfluoroalkylsulfonic acid ion is generally used. It is considered that the perfluoroalkyl chain within the anion moiety is preferably long, as diffusion of acid after exposure can be suppressed. However, a perfluoroalkyl chain of 6 to 10 carbon atoms is hardly decomposable, and hence, for minimizing bioaccumulation to improve ease of handling, a nonafluorobutanesulfonic acid ion or the like is used. Therefore, development of a novel compound which is more useful as an acid generator for a resist composition has been demanded.

The present invention takes the above circumstances into consideration, with an object of providing a novel compound useful as an acid generator for a resist composition; a compound useful as a precursor for the aforementioned compound; an acid generator; a resist composition; and a method of forming a resist pattern.

Means to Solve the Problem

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including an acid generator (B1) consisting of a compound represented by general formula (b1-1) shown below.

[Chemical Formula 1.]

(b1-1)

wherein $Q^1$ represents a divalent linkage group or a single bond; $Y^1$ represents an alkylene group which may have a substituent or a fluorinated alkylene group which may have a substituent; X represents a cyclic group of 3 to 30 carbon atoms which may have a substituent, and has an —$SO_2$— bond in the structure thereof; and $A^+$ represents an organic cation.

A second aspect of the present invention is a method of forming a resist pattern, including: applying a resist composition of the first aspect to a substrate to form a resist film on the substrate; conducting exposure of the resist film; and alkali-developing the resist film to form a resist pattern.

A third aspect of the present invention is a compound represented by general formula (I) shown below (hereafter, this compound is referred to as "compound (I)").

[Chemical Formula 2.]

(I)

wherein $Q^1$ represents a divalent linkage group or a single bond; $Y^1$ represents an alkylene group which may have a substituent or a fluorinated alkylene group which may have a substituent; X represents a cyclic group of 3 to 30 carbon atoms which may have a substituent, and has an —$SO_2$— bond in the structure thereof; and $M^+$ represents an alkali metal ion.

A fourth aspect of the present invention is a compound represented by general formula (b1-1) shown below (hereafter, this compound is referred to as "compound (B1)").

[Chemical Formula 3.]

(b1-1)

wherein $Q^1$ represents a divalent linkage group or a single bond; $Y^1$ represents an alkylene group which may have a substituent or a fluorinated alkylene group which may have a substituent; X represents a cyclic group of 3 to 30 carbon atoms which may have a substituent, and has an —$SO_2$— bond in the structure thereof; and $A^+$ represents an organic cation.

A fifth aspect of the present invention is an acid generator including the compound (B1) of the fourth aspect.

In the present description and claims, the term "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "lower alkyl group" is an alkyl group of 1 to 5 carbon atoms.

A "halogenated alkyl group" is a group in which a part or all of the hydrogen atoms of an alkyl group is substituted with halogen atoms. Examples of halogen atoms include fluorine atoms, chlorine atoms, bromine atoms and iodine atoms.

The term "aliphatic" is a relative concept used in relation to the term "aromatic", and defines a group or compound that has no aromaticity.

The term "structural unit" refers to a monomer unit that contributes to the formation of a polymeric compound (polymer, copolymer).

The term "exposure" is used as a general concept that includes irradiation with any form of radiation.

Effect of the Invention

According to the present invention, there are provided a novel compound useful as an acid generator for a resist composition; a compound useful as a precursor for the aforementioned compound; an acid generator; a resist composition; and a method of forming a resist pattern.

BEST MODE FOR CARRYING OUT THE INVENTION

<<Compound (I)>>

Firstly, the compound (I) according to the third aspect of the present invention will be described. The compound (I) of the present invention is represented by general formula (I) above.

In general formula (I), $Q^1$ represents a divalent linkage group or a single bond; $Y^1$ represents an alkylene group which may have a substituent or a fluorinated alkylene group which may have a substituent; X represents a cyclic group of 3 to 30 carbon atoms which may have a substituent, and has an —$SO_2$ bond in the structure thereof; and $M^+$ represents an alkali metal ion.

In general formula (I), $Q^1$ represents a divalent linkage group or a single bond.

As the divalent group for $Q^1$, for example, an alkylene group and a group containing a hetero atom (hereafter, referred to as "hetero atom-containing linkage group") can be mentioned.

With respect to the hetero atom-containing linkage group, the "hetero atom" is an atom other than a carbon atom and a hydrogen atom, and examples thereof include an oxygen atom, a sulfur atom and a nitrogen atom.

The alkylene group for $Q^1$ may be linear or branched. The alkylene group preferably has 1 to 12 carbon atoms, more preferably 1 to 5, and most preferably 1 to 3.

Specific examples of the alkylene group include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$; an ethylene group [—$CH_2CH_2$—]; alkylethylene groups such as —CH($CH_3$)$CH_2$—, —CH($CH_3$)CH($CH_3$)—, —C($CH_3$)$_2CH_2$—, —CH($CH_2CH_3$)$CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$—and —$CH_2$CH ($CH_3$) $CH_2CH_2$—; and a pentamethylene group [—$CH_2CH_2CH_2CH_2CH_2$—].

As the hetero atom-containing linkage group for $Q^1$, for example, non-hydrocarbon, hetero atom-containing linkage groups such as an oxygen atom (an ether bond; —O—), a sulfur atom (a thioether bond; —S—), an —NH— bond (the H may be replaced with a substituent such as an alkyl group or an acyl group), an ester bond (—C(=O)—O—), an amido group (—C(=O)—NH—), a carbonyl group (—C(=O)—) and a carbonate group (—O—C(=O)—O—); and combinations of the aforementioned non-hydrocarbon, hetero atom-containing linkage groups and the aforementioned alkylene groups, can be mentioned. Specific examples of the combinations of the aforementioned non-hydrocarbon, hetero atom-containing linkage groups and the aforementioned alkylene groups include —$R^{91}$—O— and —$R^{92}$—O—C(=O)— (wherein each of $R^{91}$ and $R^{92}$ independently represents an alkylene group). In the formulas above, as the alkylene group for $R^{91}$ and $R^{92}$, the same divalent linkage groups as those for $Q^1$ above can be mentioned.

Among the above-mentioned examples, as $Q^1$, a divalent linkage group containing an ester bond or an ether bond is preferable.

Especially, an ester bond, an ether bond or —$R^{92}$—O—C(=O)— (wherein $R^{92}$ preferably represents an alkylene group of 1 to 3 carbon atoms) is preferable, and an ester bond is particularly desirable.

In general formula (I), $Y^1$ represents an alkylene group which may have a substituent or a fluorinated alkylene group which may have a substituent.

$Y^1$ is preferably linear or branched, and preferably has 1 to 6 carbon atoms, more prefe1 to 5, and most preferably 1 to 4.

Preferable examples rably of $Y^1$ include —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

As $Y^1$, a fluorinated alkylene group is more preferable, and a fluorinated alkylene group in which the carbon atom bonded to the adjacent sulfur atom is fluorinated is particularly desirable. Examples of such fluorinated alkylene groups include —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Among these, —$CF_2CF_2$—, —$CF_2CF_2CF_2$—, and $CH_2CF_2CF_2$— are preferable, —$CF_2$—, —$CF_2CF_2$— and —$CF_2CF_2CF_2$— are more preferable, and —$CF_2$— is particularly desirable.

The alkylene group or fluorinated alkylene group for $Y^1$ may have a substituent. Examples of the substituent include an alkyl group, an alkoxy group, a halogen atom, a halogenated alkyl group, a hydroxyl group and an oxygen atom (=O).

The alkyl group for the substituent is preferably an alkyl group having 1 to 5 carbon atoms, and most preferably a methyl group, an ethyl group, a propyl group, an n-butyl group, or a tert-butyl group.

The alkoxy group for the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

As the halogen atom for the substituent, a fluorine atom, a chlorine atom, a bromine atom and an iodine atom can be mentioned, and a fluorine atom is preferable.

As the halogenated alkyl group for the substituent, a group in which a part or all of the hydrogen atoms within the aforementioned alkyl group have been substituted with the aforementioned halogen atoms can be mentioned.

In general formula (I), $M^+$ represents an alkali metal ion. As the alkali metal ion for $M^+$, a sodium ion, lithium ion and potassium ion can be mentioned, and a sodium ion or a lithium ion is preferable.

In general formula (I), X represents a cyclic group of 3 to 30 carbon atoms which may have a substituent, and has an —$SO_2$— bond in the structure thereof.

The cyclic group for X refers to a cyclic group containing a ring having an —$SO_2$— bond, and this ring is counted as the first ring. A cyclic group in which a ring having an —$SO_2$— bond is the only ring structure is referred to as a monocyclic group, and a group containing other ring structures is described as a polycyclic group regardless of the structure of the other rings.

In the compound (I) of the present invention, it is preferable that X represent a cyclic group of 3 to 30 carbon atoms which may have a substituent, and has an —O—$SO_2$— bond in the structure thereof.

When an acid generator produced from a compound (I) having an —O—$SO_2$— bond as a precursor is used in a resist composition, the lithography properties of the resist composition are improved.

The cyclic group for X may have a substituent. Examples of the substituent include an alkyl group, an alkoxy group, a halogen atom, a halogenated alkyl group, a hydroxyl group and an oxygen atom (=O). Specific examples of the substituent include those mentioned above for the substituent which the alkylene group or fluorinated alkylene group for $Y^1$ may have.

Further, as the substituent, —COOR", —OC(=O)R", a hydroxyalkyl group and a cyano group can also be mentioned. R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably 1 to 5, and most preferably a methyl group or an ethyl group.

When R" represents a cyclic alkyl group, it preferably has 3 to 15 carbon atoms, more preferably 4 to 12, and most preferably 5 to 10.Examples of the cyclic alkyl group include groups in which one or more hydrogen atoms have been removed from a monocycloalkane or a polycycloalkane such as a bicycloalkane, tricycloalkane or tetracycloalkane, and which may or may not be substituted with a fluorine atom or a fluorinated alkyl group. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the hydroxyalkyl group for the substituent, a group in which at least one hydrogen atom of the aforementioned alkyl group for the substituent is substituted with a hydroxyl group can be mentioned.

The cyclic group for X has 3 to 30 carbon atoms, preferably 4 to 20, more preferably 4 to 15, and most preferably 4 to 12. Here, the number of carbon atoms does not include the number of carbon atoms within a substituent(s).

X is not particularly limited, and arbitrary groups can be mentioned, such as aliphatic cyclic groups which may have a substituent, and aromatic cyclic groups which may have a substituent.

Specifically, as the monocyclic group, for example, a group in which one hydrogen atom has been removed from a monocycloalkane having an —$SO_2$— bond can be mentioned.

Further, as the polycyclic group, for example, a group in which one hydrogen atom has been removed from a polycycloalkane such as a bicycloalkane, tricycloalkane or tetracycloalkane which includes a ring having an —$SO_2$— bond can be mentioned.

More specifically, as X, cyclic groups represented by general formulas (X-1) to (X-4) shown below can be mentioned.

[Chemical Formula 4.]

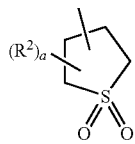
(X-1)

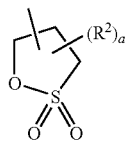
(X-2)

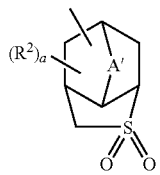
(X-3)

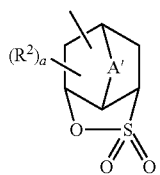
(X-4)

wherein $R^2$ represents an alkyl group of 1 to 6 carbon atoms, an alkoxy group of 1 to 6 carbon atoms, a halogenated alkyl group of 1 to 6 carbon atoms, a halogen atom, a hydroxyl group, —COOR", —OC(=O)R", a hydroxyalkyl group or a cyano group; a represents an integer of 0 to 2; and A' represents an alkylene group of 1 to 5 carbon atoms, —O—, —S—, —O—$R^3$— or —S—$R^4$—, wherein each of $R^3$ and $R^4$ independently represents an alkylene group of 1 to 5 carbon atoms.

In general formulas (X-1) to (X-4) above, the alkyl group for $R^2$ is preferably a linear or branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or an ethyl group is preferable, and a methyl group is particularly desirable.

As the alkoxy group for $R^2$, a group in which the aforementioned alkyl group for $R^2$ is bonded to an oxygen atom (—O—) can be mentioned.

As the halogen atom for $R^2$, a fluorine atom, a chlorine atom, a bromine atom and an iodine atom can be mentioned, and a fluorine atom is preferable.

As the halogenated alkyl group for $R^2$, a group in which a part or all of the hydrogen atoms within the aforementioned alkyl group for $R^2$ have been substituted with the aforementioned halogen atoms can be mentioned. As the halogenated alkyl group, a fluorinated alkyl group is preferable, and a perfluoroalkyl group is particularly desirable.

R" is as defined above.

As the hydroxyalkyl group for $R^2$, it is preferable that the alkyl group has 1 to 6 carbon atoms, and specific example includes a group in which at least one hydrogen atom of the aforementioned alkyl group has been substituted with a hydroxyl group.

a may be any one of 0 to 2, and is most preferably 0.

When a is 2, the plurality of $R^2$ may be the same or different.

In general formulas (X-3) and (X-4), A' represents an alkylene group of 1 to 5 carbon atoms, —O—, —S—, —O—$R^3$— or —S—$R^4$—.

As the alkylene group of 1 to 5 carbon atoms for A', a methylene group, an ethylene group, an n-propylene group and an isopropylene group can be mentioned.

Each of $R^3$ and $R^4$ independently represents an alkylene group of 1 to 5 carbon atoms. The alkylene group is preferably linear or branched, and preferably has 1 to 3 carbon atoms, more preferably 1 or 2.

As A', an alkylene group of 1 to 5 carbon atoms or —O— is preferable, an alkylene group of 1 to 5 carbon atoms is more preferable, and a methylene group is particularly desirable.

Specific examples of the cyclic groups represented by general formulas (X-1) to (X-4) are shown below. In the formulas shown below, "Ac" represents an acetyl group.

[Chemical Formula 5.]

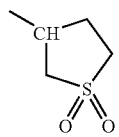
(X-1-1)

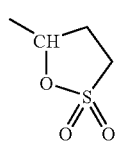
(X-2-1)

[Chemical Formula 6.]

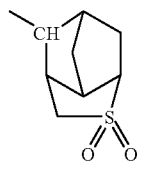
(X-3-1)

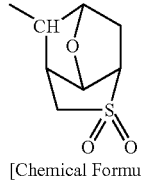
(X-3-2)

[Chemical Formula 7.]

-continued
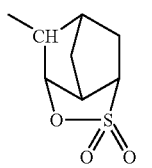 (X-4-1)
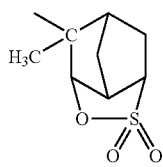 (X-4-2)
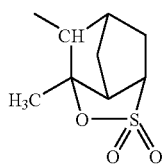 (X-4-3)
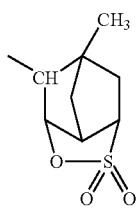 (X-4-4)
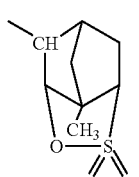 (X-4-5)
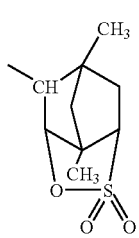 (X-4-6)
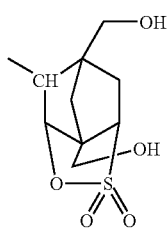 (X-4-7)
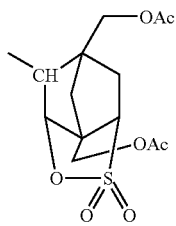 (X-4-8)
-continued
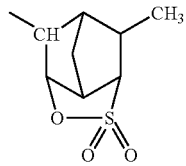 (X-4-9)
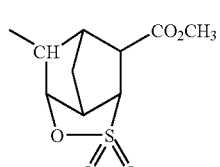 (X-4-10)
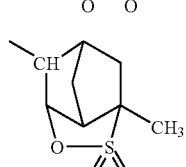 (X-4-11)
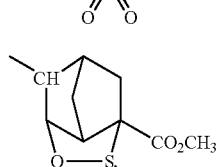 (X-4-12)
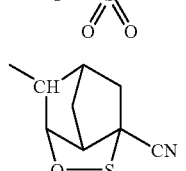 (X-4-13)
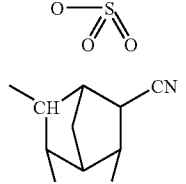 (X-4-14)
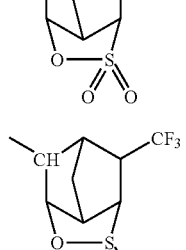 (X-4-15)
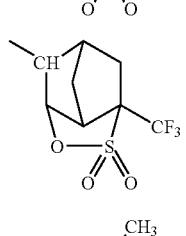 (X-4-16)
(X-4-17)
[Chemical Formula 8.]

(X-4-18) 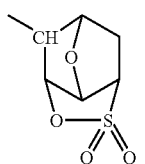

(X-4-19) 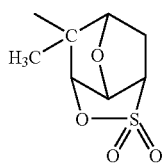

(X-4-20) 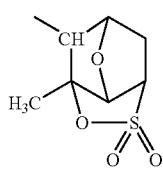

(X-4-21) 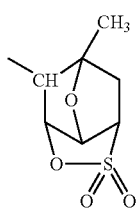

(X-4-22) 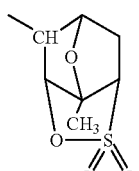

(X-4-23) 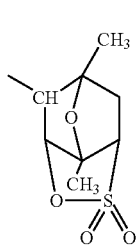

(X-4-24) 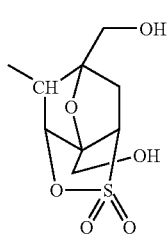

(X-4-25) 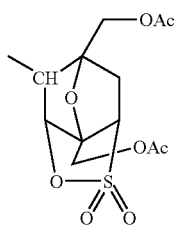

(X-4-26) 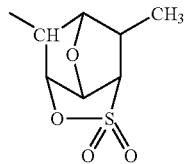

(X-4-27) 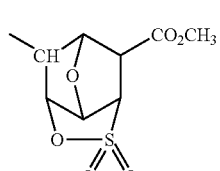

(X-4-28) 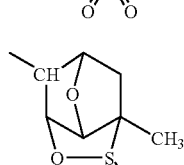

(X-4-29) 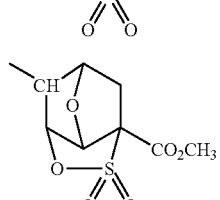

(X-4-30) 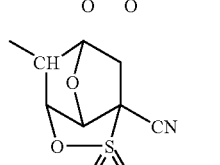

(X-4-31) 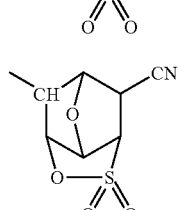

(X-4-32) 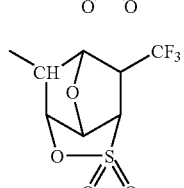

(X-4-33) 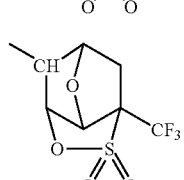

Among these, as X in general formula (I) above, a cyclic group of 3 to 30 carbon atoms which may have a substituent, and has an —O—SO$_2$— bond in the structure thereof is preferable, at least one member selected from the group consisting of cyclic groups represented by chemical formulas (X-4-1), (X-4-18), (X-1-1) and (X-2-1) above are more preferable, and the cyclic group represented by chemical formula (X-4-1) above is particularly desirable. When an acid generator produced from a compound (I) as a precursor in which X is any one of the groups mentioned above is used in a resist composition, the lithography properties of the resist composition are improved.

In the present invention, as the compound (I), a compound represented by general formula (I-11) shown below is particularly desirable.

[Chemical Formula 9.]

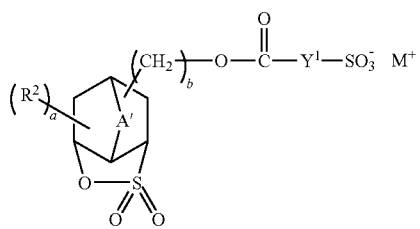
(I-11)

wherein A', $R^2$, a, $Y^1$ and $M^+$ are as defined above; and b represents an integer of 0 to 5.

b is preferably 0 or 1, and most preferably 0.

As $Y^1$, a group represented by the formula: —[C($R^5$)($R^6$)]$_c$— (wherein each of $R^5$ and $R^6$ independently represents a fluorine atom or a fluorinated alkyl group; and c represents an integer of 1 to 3) is preferable. In the formula above, c is most preferably 1. As the fluorinated alkyl group for $R^5$ and $R^6$, a linear or branched fluorinated alkyl group is preferable. Further, the fluorinated alkyl group is preferably a perfluoroalkyl group. The fluorinated alkyl group preferably has 1 to 5 carbon atoms, and most preferably 1. It is particularly desirable that each of $R^5$ and $R^6$ represents a fluorine atom.

The compound (I) is a novel compound.

The compound (I) is useful as a precursor in the production of the compound (B1) described below.

<Production Method of compound (I)>

The production method of the compound (I) according to the third aspect of the present invention is not particularly limited. For example, when a compound represented by general formula (I-11) above is to be produced as the compound (I), a method in which a compound (I-3) represented by general formula (I-3) shown below and a compound (I-4) represented by general formula (I-4) shown below are subjected to dehydration/condensation in the presence of an acidic catalyst can be preferably used.

[Chemical Formula 10.]

$$HO-\overset{O}{\underset{\|}{C}}-Y^1-SO_3^-\ M^+$$
(I-3)

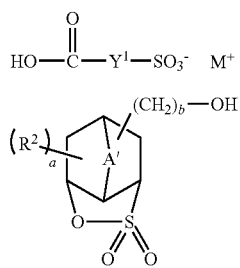
(I-4)

In general formulas (I-3) and (I-4), $Y^1$ and $M^+$ are respectively as defined for $Y^1$ and $M^+$ in general formula (I) above.

A', $R^2$, a and b are respectively as defined for A', $R^2$, a and b in general formula (I-11) above.

As the compound (I-3) and the compound (I-4), commercially available compounds may be used, or the compounds may be synthesized.

Although there is no particular limitation, the compound (I-3) can be synthesized by a method including the steps of subjecting a compound (I-1) represented by general formula (I-1) shown below to an alkali treatment to obtain a compound (I-2) represented by general formula (I-2) shown below (hereafter, this step is referred to as "step (i)"); and heating the compound (II) in the presence of an acid to thereby obtain the compound (I-3) (hereafter, this step is referred to as "step (ii)").

[Chemical Formula 11.]

$$R^1-O-\overset{O}{\underset{\|}{C}}-Y^1-SO_2F$$
(I-1)

$$M^+\ {}^-O-\overset{O}{\underset{\|}{C}}-Y^1-SO_3^-\ M^+$$
(I-2)

wherein $R^1$ represents an alkyl group of 1 to 5 carbon atoms; and $Y^1$ and $M^+$ are as defined above.

In step (i) above, as the compound (I), a commercially available compound may be used.

In step (i), the alkali treatment can be conducted, for example, by heating the compound (I-1) in the presence of an alkali. More specifically, the alkali treatment can be conducted by dissolving the compound (I-1) in a solvent such as water, tetrahydrofuran, or the like, and adding an alkali to the resulting solution and heating the solution.

Examples of the alkali include sodium hydroxide, potassium hydroxide and lithium hydroxide.

The amount of the alkali used is preferably 1 to 5 moles, and more preferably 2 to 4 moles, per 1 mole of the compound (I-1).

The heating temperature is preferably 20 to 120° C., and more preferably about 50 to 100° C. The heating time depends on the heating temperature, but in general, the heating time is preferably 0.5 to 12 hours, and more preferably 1 to 5 hours.

After the alkali treatment, neutralization may be conducted. The neutralization can be conducted by adding an acid such as hydrochloric acid, sulfuric acid, p-toluenesulfonic acid, or the like to the reaction liquid obtained after the alkali treatment. It is preferable to conduct the neutralization so that the pH of the reaction liquid after addition of an acid becomes within the range of 6 to 8.

After the reaction, the compound (I-2) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

Step (ii) above may be performed, for example, by dissolving the compound (I-2) in a solvent such as acetonitrile, methyl ethyl ketone, or the like, and adding an acid to the resulting solution and heating the solution.

In step (ii), as the acid, an acid which exhibits stronger acidity that the compound (I-3) is used. Examples of such an acid include p-toluenesulfonic acid, sulfuric acid and hydrochloric acid.

The amount of the acid used is preferably 0.5 to 3 moles, and more preferably 1 to 2 moles, per 1 mole of the compound (I-2).

The heating temperature is preferably 20 to 150° C., and more preferably about 50 to 120° C. The heating time depends on the heating temperature, but in general, the heating time is preferably 0.5 to 12 hours, and more preferably 1 to 5 hours.

After the reaction, the compound (I-3) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

The dehydration/condensation reaction of the compound (I-3) and the compound (I-4) can be conducted, for example, by dissolving the compound (I-3) and the compound (I-4) in an aprotic organic solvent such as dichloroethane, benzene, toluene, ethylbenzene, chlorobenzene, acetonitrile or N,N-dimethylformamide, followed by stirring in the presence of an acidic catalyst.

In the dehydration/condensation reaction, as the organic solvent, it is particularly desirable to use an aromatic organic solvent such as toluene, xylene or chlorobenzene, as the yield, purity and the like of the obtained compound (I) are improved.

The reaction temperature for the dehydration/condensation reaction is preferably about 20 to 200° C., and more preferably 50 to 150° C. The reaction time varies, depending on the reactivity of the compound (I-3) and the compound (I-4), the reaction temperature, and the like, but in general, the reaction time is preferably 1 to 30 hours, and more preferably 3 to 30 hours.

In the dehydration/condensation reaction, the amount of the compound (I-3) is not particularly limited, but in general, the amount of the compound (I-3) is preferably 0.2 to 3 moles, more preferably 0.5 to 2 moles, and most preferably 0.75 to 1.5 moles, per 1 mole of the compound (I-4).

Examples of acidic catalysts include an organic acid such as p-toluenesulfonic acid, and organic acids such as sulfuric acid and hydrochloric acid. These acidic catalysts may be used individually, or in a combination of two or more.

In the dehydration/condensation reaction, the acidic catalyst may be used in a catalyst amount, or in an amount corresponding to the solvent. In general, the amount of the acidic catalyst is 0.001 to 5 moles, per 1 mole of the compound (I-4).

The dehydration/condensation reaction may be conducted while removing water by using a Dean-Stark apparatus. In this manner, the reaction time can be shortened. Further, in the dehydration/condensation reaction, a dehydrating agent such as 1,1'-carbonyldiimidazole or N,N'-dicyclohexylcarbodiimide may also be used.

When a dehydrating agent is used, in general, the amount of the dehydrating agent is preferably 0.2 to 5 moles, more preferably 0.5 to 3 moles, per 1 mole of the compound (I-4).

The structure of the compound obtained in the above-described manner can be confirmed by a general organic analysis method such as $^{1}$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Compound (B1)>>

Next, the compound (B1) according to the fourth aspect of the present invention will be described. The compound (B1) of the present invention is represented by general formula (b1-1) above.

In general formula (b1-1), $Q^1$, $Y^1$ and X are respectively as defined for $Q^1$, $Y^1$ and X in general formula (I) above.

In the compound (B1), it is preferable that $Q^1$ represent a divalent linkage group containing an ester bond or an ether bond.

Further, in the compound (B1), it is preferable that X represent a cyclic group of 3 to 30 carbon atoms which may have a substituent, and has an —O—SO$_2$— bond in the structure thereof.

As the organic cation for A$^+$, there is no particular limitation, and any of those conventionally known as cation moiety for an onium salt-based acid generator can be appropriately selected for use. More specifically, a cation moiety represented by general formula (b'-1), (b'-2), (b'-5) or (b-6) show below can be preferably used.

[Chemical Formula 12.]

(b'-1)

(b'-2)

wherein $R^{1"}$ to $R^{3"}$, $R^{5"}$ and $R^{6"}$ each independently represents an aryl group or alkyl group, wherein two of $R^{1"}$ to $R^{3"}$ in formula (b'-1) may be bonded to each other to form a ring with the sulfur atom, with the proviso that at least one of $R^{1"}$ to $R^{3"}$ represents an aryl group, and at least one of $R^{5"}$ and $R^{6"}$ represents an aryl group.

[Chemical Formula 13.]

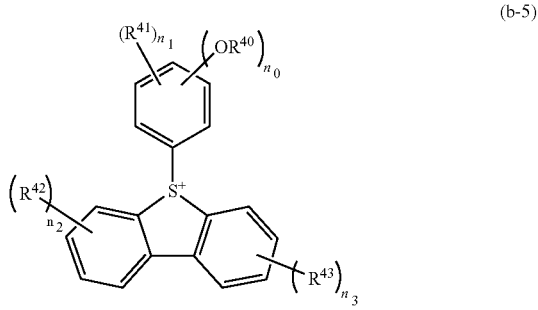

(b-5)

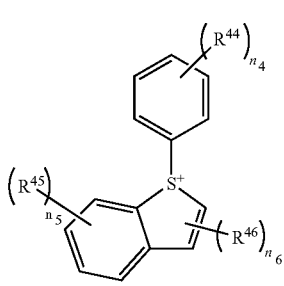
(b-6)

wherein $R^{40}$ represents a hydrogen atom or an alkyl group; $R^{41}$ represents an alkyl group, an acetyl group, a carboxy group or a hydroxyalkyl group; each of $R^{42}$ to $R^{46}$ independently represents an alkyl group, an acetyl group, an alkoxy group, a carboxy group, a hydroxyl group or a hydroxyalkyl group; each of $n_0$ to $n_5$ independently represents an integer of 0 to 3, with the proviso that $n_0+n_1$ is 5 or less; and $n_6$ represents an integer of 0 to 2.

In formula (b'-1), $R^{1\prime\prime\prime}$ to $R^{3\prime\prime\prime}$ each independently represents an aryl group or an alkyl group. In formula (b'-1), two of $R^{1\prime\prime\prime}$ to $R^{3\prime\prime\prime}$ may be bonded to each other to form a ring with the sulfur atom.

Further, among $R^{1\prime\prime\prime}$ to $R^{3\prime\prime\prime}$, at least one group represents an aryl group. Among $R^{1\prime\prime\prime}$ to $R^{3\prime\prime\prime}$, two or more groups are preferably aryl groups, and it is particularly desirable that all of $R^{1\prime\prime\prime}$ to $R^{3\prime\prime\prime}$ are aryl groups.

The aryl group for $R^{1\prime\prime\prime}$ to $R^{3\prime\prime\prime}$ is not particularly limited. Examples thereof include an unsubstituted aryl group having 6 to 20 carbon atoms, a substituted aryl group in which a part or all of the hydrogen atoms of the aforementioned unsubstituted aryl group has been substituted with alkyl groups, alkoxy groups, alkoxyalkyloxy groups, alkoxycarbonylalkyloxy groups, halogen atoms, hydroxyl groups, alkoxycarboxyl groups, —O—C(=O)—$R^{6\prime}$ or the like, and —($R^{4\prime}$)—C—(=O)—$R^{5\prime}$. $R^{4\prime}$ represents an alkylene group of 1 to 5 carbon atoms. $R^{5\prime}$ represents an aryl group. As the aryl group for $R^{5\prime}$, the same aryl groups as those for $R^{1\prime\prime\prime}$ to $R^{3\prime\prime\prime}$ can be mentioned. $R^{6\prime}$ represents a cyclic alkyl group.

The unsubstituted aryl group is preferably an aryl group having 6 to 10 carbon atoms because it can be synthesized at a low cost. Specific examples thereof include a phenyl group and naphthyl group.

The alkyl group as the substituent for the substituted aryl group is preferably an alkyl group having 1 to 5 carbon atoms, and most preferably a methyl group, an ethyl group, a propyl group, an n-butyl group, or a tert-butyl group.

The alkoxy group as the substituent for the substituted aryl group is preferably a group represented by the formula: —O—$R^{52}$ (wherein $R^{52}$ represents an alkyl group of 1 to 10 carbon atoms which may have a fluorine atom), and more preferably a group having 1 to 7 carbon atoms. As the alkyl group for $R^{52}$, a methyl group, an ethyl group, an n-propyl group, an isopropyl group, an n-butyl group, a t-butyl group or an n-hexyl group is particularly desirable.

When $R^{52}$ has a fluorine atom, it is preferably a group represented by the formula: —(CH$_2$)$_e$—(CF$_2$)$_f$—CF$_3$ (wherein e+f≦9). In the formula above, it is preferable that e represents an integer of 3 to 5 and f represents an integer of 1 to 3, and it is particularly desirable that both of e and f be 3.

The halogen atom as the substituent for the substituted aryl group is preferably a fluorine atom.

The alkoxycarboxyl group as the substituent for the substituted aryl group is preferably a group represented by the formula: —O—$R^{55}$—COOH (wherein $R^{55}$ represents a linear or branched alkylene group of 1 to 5 carbon atoms), and more preferably a group having 1 to 3 carbon atoms. As the alkylene group for $R^{55}$, a methylene group or an ethylene group is particularly desirable.

Examples of the alkoxyalkyloxy group as the substituent for the substituted aryl group include a group represented by a general formula —O—C($R^{47}$)($R^{48}$)—O—$R^{49}$ (wherein each of $R^{47}$ and $R^{48}$ independently represents a hydrogen atom or a linear or branched alkyl group; and $R^{49}$ represents an alkyl group).

The alkyl group for $R^{47}$ and $R^{48}$ preferably has 1 to 5 carbon atoms, and may be either linear or branched, and is preferably an ethyl group or a methyl group, and most preferably a methyl group.

It is preferable that at least one of $R^{47}$ and $R^{48}$ be a hydrogen atom, and it is particularly desirable that either one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, ethyl group, propyl group, n-butyl group and tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of polycycloalkane include adamantane, norbornane, isobornane, tricyclodecane and tetracyclododecane. Among these, groups in which one or more hydrogen atoms have been removed from adamantane are preferable.

An example of the alkoxycarbonylalkyloxy group as the substituent for the substituted aryl group includes a group represented by a general formula: —O—$R^{50}$—C(=O)—O—$R^{51}$ (wherein $R^{50}$ represents a linear or branched alkylene group; and $R^{51}$ represents an alkyl group).

The linear or branched alkylene group for $R^{50}$ preferably has 1 to 5 carbon atoms, and examples thereof include a methylene group, ethylene group, trimethylene group, tetramethylene group and 1,1-dimethylethylene group.

As the alkyl group for $R^{51}$, a methyl group, an ethyl group, a propyl group, an n-butyl group, a cyclopentyl group, a cyclohexyl group, an adamantyl group, a norbornyl group, an isobornyl group, a tricyclodecanyl group and a tetracycododecanyl group can be mentioned. Alternatively, the alkyl group for $R^{51}$ may be a tertiary alkyl group, and examples thereof include 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group, 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group, 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group and tert-hexyl group.

In the group represented by the formula —O—C(=O)—R$^{6\prime\prime}$ as the substituent for the substituted aryl group, R$^{6\prime\prime}$ represents a cyclic alkyl group of 3 to 20 carbon atoms, and the same cyclic groups as those for R$^{49}$ above can be mentioned. R$^{6\prime\prime}$ is most preferably an adamantyl group.

The aryl group for R$^{1\prime\prime}$ to R$^{3\prime\prime}$ is preferably a phenyl group or a naphthyl group.

The alkyl group for R$^{1\prime\prime}$ to R$^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Among these, a methyl group is most preferable because it is excellent in resolution and can be synthesized at a low cost.

When two of R$^{1\prime\prime}$ to R$^{3\prime\prime}$ are bonded to each other to form a ring with the sulfur atom, it is preferable that the two of R$^{1\prime\prime}$ to R$^{3\prime\prime}$ form a 3 to 10-membered ring including the sulfur atom, and it is particularly desirable that the two of R$^{1\prime\prime}$ to R$^{3\prime\prime}$ form a 5 to 7-membered ring including the sulfur atom.

When two of R$^{1\prime\prime}$ to R$^{3\prime\prime}$ are bonded to each other to form a ring with the sulfur atom, the remaining one of R$^{1\prime\prime}$ to R$^{3\prime\prime}$ is preferably an aryl group. As examples of the aryl group, the same aryl groups as those for R$^{1\prime\prime}$ to R$^{3\prime\prime}$ can be mentioned.

Specific examples of cation moiety represented by general formula (b'-1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethylphenyl) diphenylsulfonium, (4-(2-methyl-2-adamantyloxycarbonylmethyloxy)phenyl) diphenylsulfonium, (4-(2-methyl-2-adamantyloxycarbonylmethyloxy)-3,5-dimethylphenyl) diphenylsulfonium, tri(4-methylphenyl)sulfonium, dimethyl (4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl) phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl) tetrahydrothiopyranium and 1-(4-methylphenyl)tetrahydrothiopyranium.

In formula (b'-2), R$^{5\prime\prime}$ and R$^{6\prime\prime}$ each independently represents an aryl group or alkyl group. At least one of R$^{5\prime\prime}$ and R$^{6\prime\prime}$ represents an aryl group. It is preferable that both of R$^{5\prime\prime}$ and R$^{6\prime\prime}$ represent an aryl group.

As the aryl group for R$^{5\prime\prime}$ and R$^{6\prime\prime}$, the same aryl groups as those for R$^{1\prime\prime}$ to R$^{3\prime\prime}$ can be mentioned.

As the alkyl group for R$^{5\prime\prime}$ and R$^{6\prime\prime}$, the same alkyl groups as those for R$^{1\prime\prime}$ to R$^{3\prime\prime}$ can be mentioned.

It is particularly desirable that both of R$^{5\prime\prime}$ and R$^{6\prime\prime}$ represents a phenyl group.

Specific examples of cation moiety represented by general formula (b'-2) include diphenyliodonium and bis(4-tert-butylphenyl)iodonium.

In general formulas (b'-5) and (b-6), with respect to R$^{40}$ to R$^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

$n_0$ is preferably 0 or 1.

$n_1$ is preferably 0 to 2.

It is preferable that each of $n_2$ and $n_3$ independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1.

In the present invention, as A$^+$, a cation moiety represented by general formula (b'-1) or (b'-5) is preferable. Especially, a cation moiety represented by any one of formulas (b'-1-1) to (b'-1-20) and (b-5-1) to (b-5-5) shown below are preferable, and a cation moiety having a triphenyl skeleton such as a cation moiety represented by any one of formulas (b'-1-1) to (b'-1-8) and (b'-1-11) to (b'-1-15) shown below are more preferable.

In formulas (b'-1-9) and (b'-1-10), each of R$^8$ and R$^9$ independently represents a phenyl group or naphthyl group which may have a substituent, an alkyl group of 1 to 5 carbon atoms, an alkoxy group or a hydroxy group.

u is an integer of 1 to 3, and most preferably 1 or 2.

[Chemical Formula 14.]

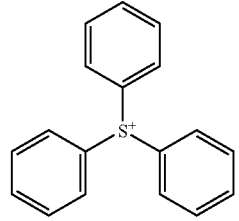

(b'-1-1)

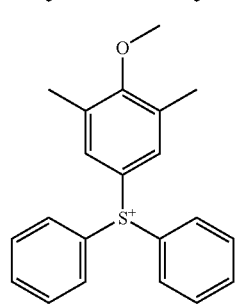

(b'-1-2)

(b'-1-3)
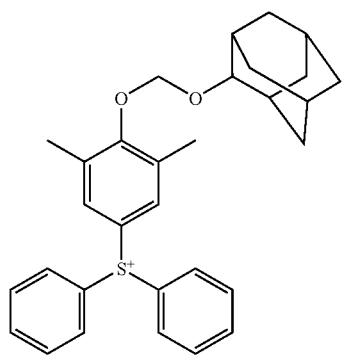
(b'-1-4)
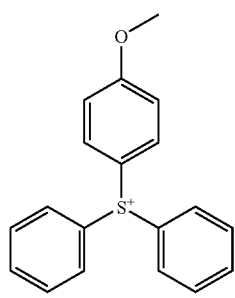
(b'-1-5)
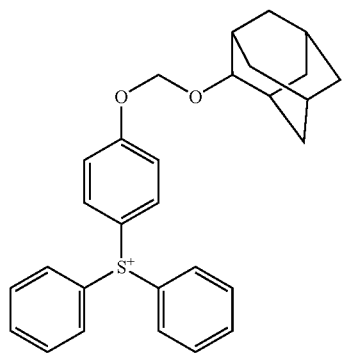
(b'-1-6)
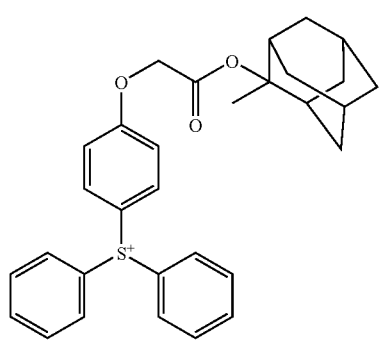
(b'-1-7)
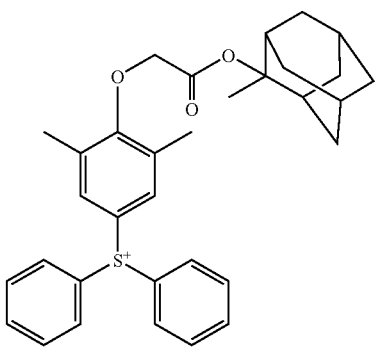
(b'-1-8)
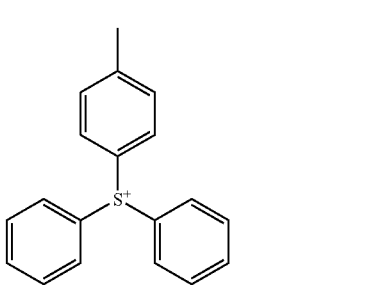
(b'-1-9)
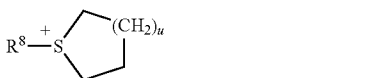
(b'-1-10)
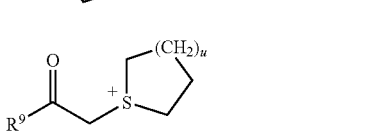
[Chemical Formula 15.]
(b'-1-11)
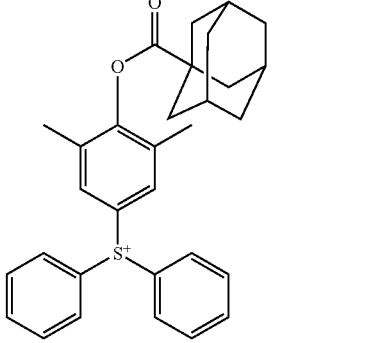
(b'-1-12)
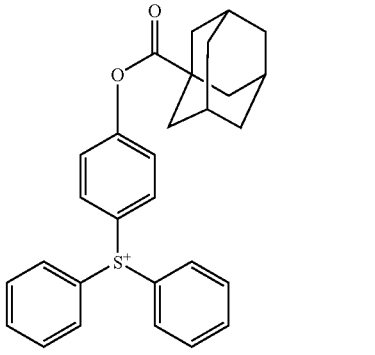

-continued
(b'-1-13)
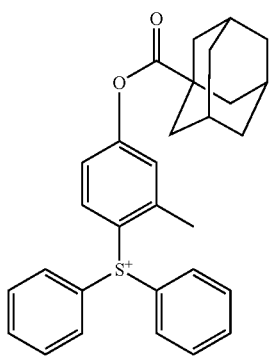
(b'-1-14)
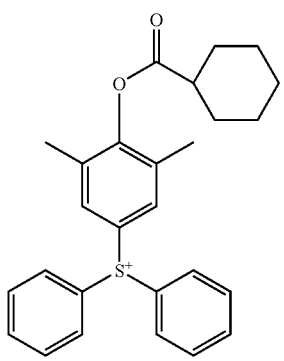
(b'-1-15)
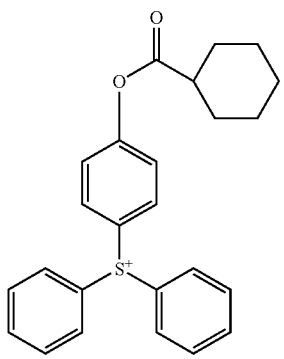
[Chemical Formula 16.]
(b'-1-16)
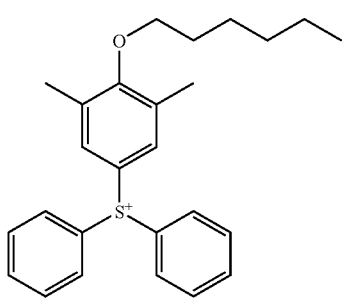
-continued
(b'-1-17)
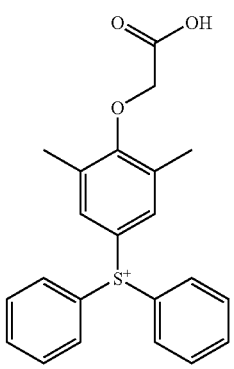
(b'-1-18)
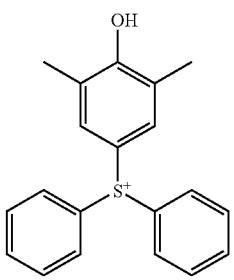
(b'-1-19)
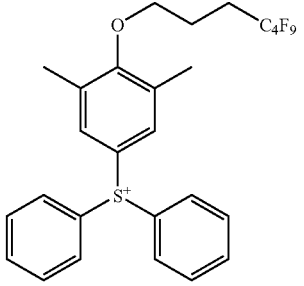
(b'-1-20)
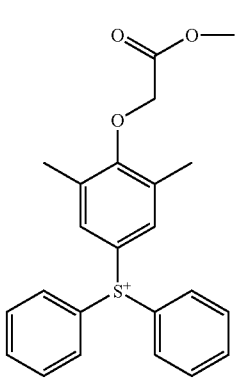
[Chemical Formula 17.]
(b-5-1)
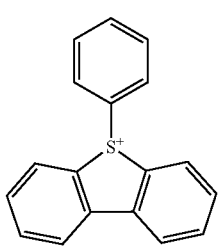

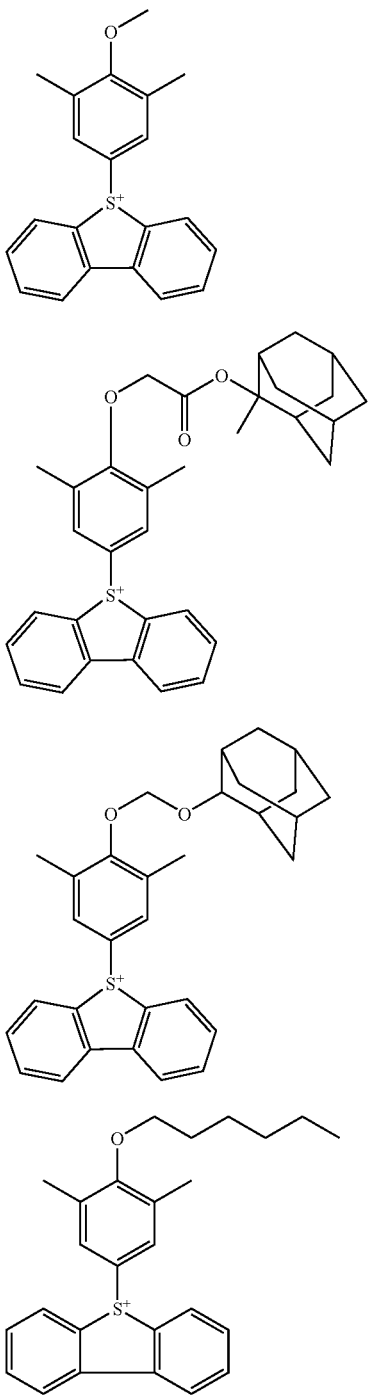

In the present invention, as the compound (B1), compounds in which the anion moiety is represented by general formula (I-11) above and the cation moiety is represented by any one of formulas (b'-1-1) to (b'-1-20) and (b-5-1) to (b-5-5) are preferable. Among these, compounds in which the cation moiety is represented by the formula (b'-1-1), (b'-1-7), (b'-1-8), (b'-1-9), (b'-1-10), (b'-1-11), (b'-1-16), to (b'-1-19) or (b-5-5) are particularly desirable.

The method for producing the compound (B1) is not particularly limited. For example, the compound (B1) can be produced by reacting the aforementioned compound (I) with a compound (II) represented by general formula (II) shown below.

[Chemical Formula 18.]

$$A^+Z^- \qquad (II)$$

wherein $A^+$ is as defined above; and $Z^-$ represents a low nucleophilic halogen ion, an ion which is capable of forming an acid exhibiting a lower acidity than the compound (I), $BF_4^-$, $AsF_6^-$, $SbF_6^-$, $PF_6^-$ or $ClO_4^-$.

As the low nucleophilic halogen ion for $Z^-$, a bromine ion and a chlorine ion can be mentioned.

As the ion for $Z^-$ which is capable of forming an acid exhibiting a lower acidity than the compound (I), a p-toluenesulfonic acid ion, a methanesulfonic acid ion, a benzenesulfonic acid ion, and a trifluoromethanesulfonic acid ion can be mentioned.

The compound (I) can be reacted with the compound (II), for example, by dissolving the compound (I) and the compound (II) in a solvent such as water, dichloromethane, acetonitrile, methanol, chloroform or methylene chloride, and stirring the resulting solution to effect a reaction.

The reaction temperature is preferably 0 to 150° C., and more preferably 0 to 100° C. The reaction time varies, depending on the reactivity of the compound (I) and the compound (II), the reaction temperature, and the like. However, in general, the reaction time is preferably 0.5 to 10 hours, and more preferably 1 to 5 hours.

Generally, the amount of the compound (II) used in the reaction is preferably 0.5 to 2 moles, per 1 mole of the compound (I).

The structure of the compound obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The compound (B1) is a novel compound useful as an acid generator, and can be blended within a resist composition.

<<Acid Generator>>

The acid generator according to the fifth aspect of the present invention consists of the compound (B1) according to the aforementioned fourth aspect of the present invention.

The acid generator is useful as an acid generator for a chemically amplified resist composition, for example, an acid-generator component (B) for the resist composition according to the first aspect of the present invention described below.

<<Resist Composition>>

The resist composition according to the first aspect of the present invention includes a base component (A) (hereafter, referred to as "component (A)") which exhibits changed solubility in an alkali developing solution under action of acid and an acid-generator component (B) (hereafter, referred to as "component (B)") which generates acid upon exposure, and the component (B) includes an acid generator (B1) consisting of a compound represented by general formula (b1-1) above.

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, frequently referred to as "low molecular weight compounds") and high molecular weight resins (polymeric materials) having a molecular weight of 2,000 or more. Generally, as the aforementioned low molecular weight compound, a non-polymer is used. With respect to the aforementioned resin (polymer or copolymer), the molecular weight is the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under action of acid may be used. Alternatively, as the component (A), a low molecular weight material which exhibits changed solubility in an alkali developing solution under action of acid may be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of $\alpha$-(hydroxyalkyl)acrylic acid and a lower alkyl ester of $\alpha$-(hydroxyalkyl)acrylic acid, as it enables formation of a satisfactory resist pattern with minimal swelling. Here, the term "$\alpha$-(hydroxyalkyl) acrylic acid" refers to one or both of acrylic acid in which a hydrogen atom is bonded to the carbon atom on the $\alpha$-position having the carboxyl group bonded thereto, and $\alpha$-hydroxyalkylacrylic acid in which a hydroxyalkyl group (preferably a hydroxyalkyl group of 1 to 5 carbon atoms) is bonded to the carbon atom on the $\alpha$-position.

As the cross-linking agent, typically, an amino-based cross-linking agent such as a glycoluril having a methylol group or alkoxymethyl group is preferable, as it enables formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, as the component (A), a base component which exhibits increased solubility in an alkali developing solution by action of acid is used. The component (A) is insoluble in an alkali developing solution prior to exposure, and when acid is generated from the component (B) upon exposure, the solubility of the component (A) in an alkali developing solution increases. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component which exhibits increased solubility in an alkali developing solution under action of acid. That is, the resist composition of the present invention is preferably a positive resist composition.

The component (A) may be a resin component (A1) which exhibits increased solubility in an alkali developing solution under action of acid (hereafter, referred to as "component (A1)"), a low molecular weight compound (A2) which exhibits increased solubility in an alkali developing solution under action of acid (hereafter, referred to as "component (A2)"), or a mixture of the component (A1) and the component (A2). It is preferable that the component (A) contain the component (A1).

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the $\alpha$-position, and acrylate esters having a substituent (an atom other than a hydrogen atom or a group) bonded to the carbon atom on the $\alpha$-position. As the substituent, a lower alkyl group or a halogenated lower alkyl group can be mentioned.

With respect to the "structural unit derived from an acrylate ester", the "$\alpha$-position (the carbon atom on the $\alpha$-position)" refers to the carbon atom having the carbonyl group bonded thereto, unless specified otherwise.

With respect to the acrylate ester, specific examples of the lower alkyl group for the substituent at the $\alpha$-position include linear or branched alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

It is particularly desirable that the component (A1) have a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

Structural Unit (a1)

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution.

Generally, groups that form either a cyclic or chain-like tertiary alkyl ester with the carboxyl group of the (meth) acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be mentioned. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, as the groups bonded to the oxygen atom of the carbonyl group (—C(O)—O—) within the structural units represented by general formulas (a1"-1) to (a1"-6) shown below, can be mentioned.

[Chemical Formula 19.]

(a1"-1)

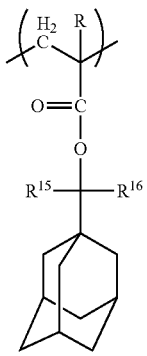

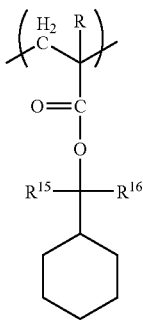
(a1″-2)

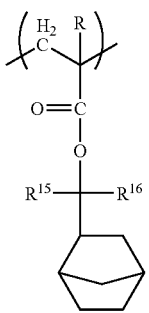
(a1″-3)

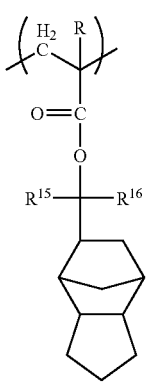
(a1″-4)

(a1″-5)

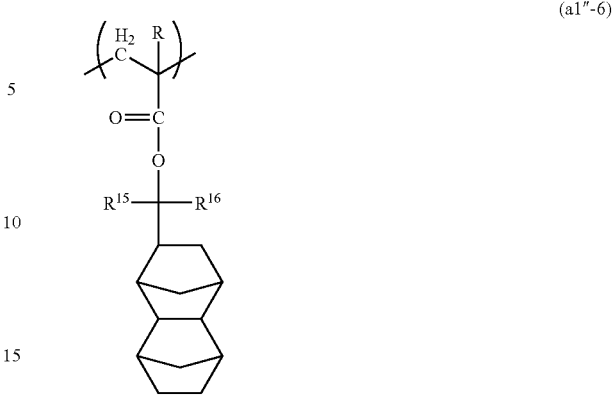
(a1″-6)

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 20.]

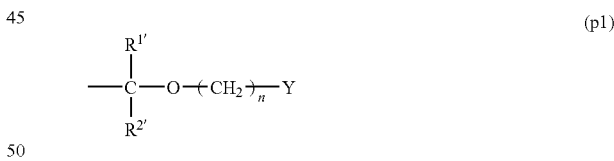
(p1)

wherein $R^{1'}$ and $R^{2'}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1'}$ and $R^{2'}$, the same lower alkyl groups as those for R above can be mentioned. As the lower alkyl group for $R^{1'}$ and $R^{2'}$, a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 21.]

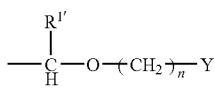
(p1-1)

wherein $R^{1\prime}$, n and Y are as defined above.

As the lower alkyl group for Y, the same lower alkyl groups as those for R above can be mentioned.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be mentioned.

Further, as the acetal-type, acid dissociable, dissolution inhibiting group, groups represented by general formula (p2) shown below can also be mentioned.

[Chemical Formula 22.]

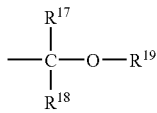
(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be mentioned. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 23.]

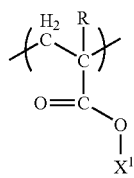
(a1-0-1)

wherein R represents a hydrogen atom, a lower alkyl group or a halogenated lower alkyl group; and $X^1$ represents an acid dissociable, dissolution inhibiting group.

[Chemical Formula 24.]

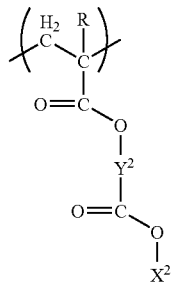
(a1-0-2)

wherein R represents a hydrogen atom, a lower alkyl group or a halogenated lower alkyl group; $X^2$ represents an acid dissociable, dissolution inhibiting group; and $Y^2$ represents an alkylene group, an aliphatic cyclic group or a divalent linkage group having an ether bond.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is as defined for $X^1$ in general formula (a1-0-1).

$Y^2$ represents an alkylene group, an aliphatic cyclic group or a divalent linkage group having an ether bond.

When $Y^2$ is an alkylene group, it is preferably an alkylene group of 1 to 10 carbon atoms, more preferably an alkylene group of 1 to 6 carbon atoms, still more preferably an alkylene group of 1 to 4 carbon atoms, and most preferably an alkylene group of 1 to 3 carbon atoms.

When $Y^2$ is an aliphatic cyclic group, it is preferably a divalent aliphatic cyclic group. As the aliphatic cyclic group, the same aliphatic cyclic groups as those mentioned above in connection with the explanation of "aliphatic cyclic group" can be used, except that two hydrogen atoms have been removed therefrom.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ is a divalent linkage group having an ether bond, it is preferably a group represented by the formula: —$Y^a$—O—$Y^b$—.

In the group represented by the formula: —$Y^a$—O—$Y^b$—, $Y^a$ represents a divalent hydrocarbon group of 2 or more carbon atoms which may have a substituent. The hydrocarbon group may be either an aliphatic hydrocarbon group or an aromatic hydrocarbon group, although an aliphatic hydrocarbon group is preferable. As the aliphatic hydrocarbon group, a linear or branched aliphatic hydrocarbon group and an aliphatic hydrocarbon group containing a ring in the structure thereof can be mentioned. More specifically, such groups are the same as the divalent aliphatic cyclic group and alkylene group for $Y^2$ which have 2 or more carbon atoms. Further, $Y^a$ may have a substituent. When $Y^a$ is a linear or branched aliphatic hydrocarbon group, as the substituent, a fluorine atom, a fluorinated alkyl group of 1 to 5 carbon atoms and an oxygen atom (=O) can be mentioned. When $Y^a$ is an aliphatic hydrocarbon group containing a ring in the structure thereof, as the substituent, the same substituents as those for the aforementioned "aliphatic cyclic group" can be mentioned.

$Y^a$ is preferably a linear aliphatic hydrocarbon group, more preferably a linear alkylene group, still more preferably a linear alkylene group of 2 to 5 carbon atoms, and most preferably an ethylene group.

$Y^b$ represents a divalent hydrocarbon group of 1 or more carbon atoms which may have a substituent. As the hydrocarbon group for $Y^b$, the same as the divalent hydrocarbon group of 2 or more carbon atoms for $Y^a$, and a methylene group which may have a substituent can be mentioned. As the substituent which a methylene group may have, the same substituents as those which a linear or branched aliphatic hydrocarbon group may have can be mentioned.

As $Y^b$, a linear or branched aliphatic hydrocarbon group is preferable, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 25.]

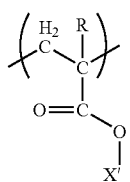
(a1-1)

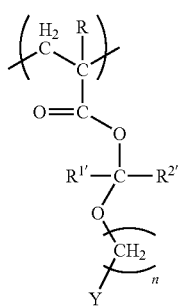
(a1-2)

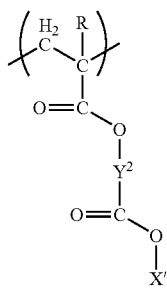
(a1-3)

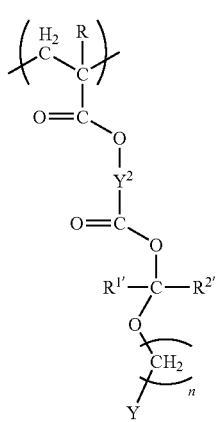
(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group, an aliphatic cyclic group or a divalent linkage group having an ether bond; R is as defined above; and each of $R^{1\prime}$ and $R^{2\prime}$ independently represents a hydrogen atom or a lower alkyl group of 1 to 5 carbon atoms.

Examples of the tertiary alkyl ester-type acid dissociable, dissolution inhibiting group for X' are the same as the above-mentioned tertiary alkyl ester-type acid dissociable, dissolution inhibiting groups for $X^1$.

As $R^{1\prime}$, $R^{2\prime}$, n and Y, the same as $R^{1\prime}$, $R^{2\prime}$, n and Y defined for general formula (p1) described above in connection with the "acetal-type acid dissociable, dissolution inhibiting group" may be mentioned.

As $Y^2$, the same as $Y^2$ defined for general formula (a1-0-2) above may be mentioned.
Specific examples of structural units represented by general formula (a1-1) to (a1-4) are shown below.
[Chemical Formula 26.]
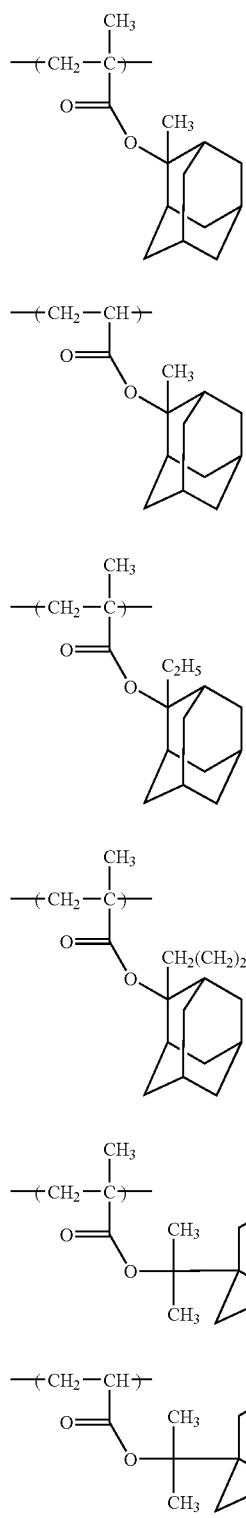
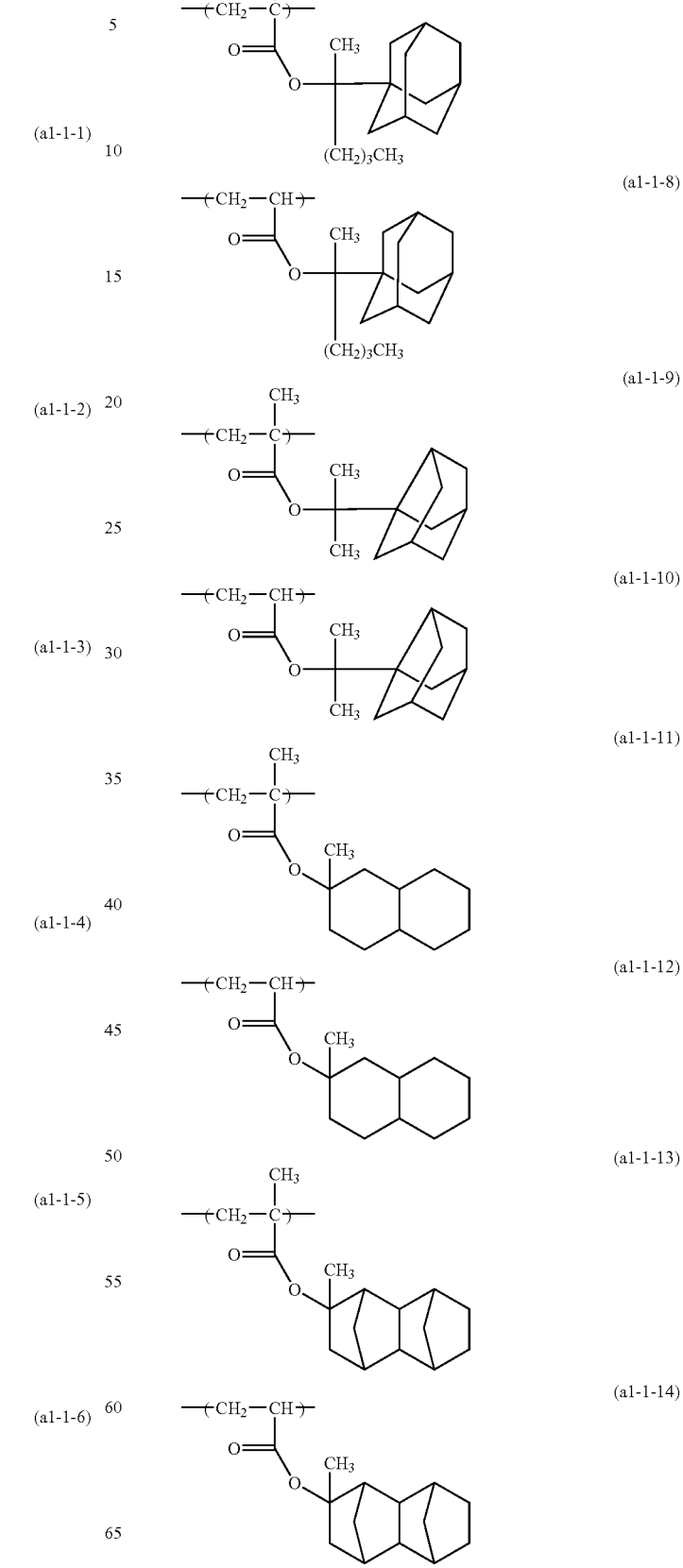

(a1-1-15)
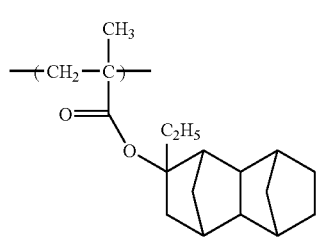
(a1-1-16)
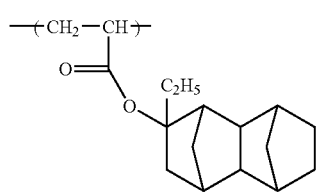
[Chemical Formula 27.]
(a1-1-17)
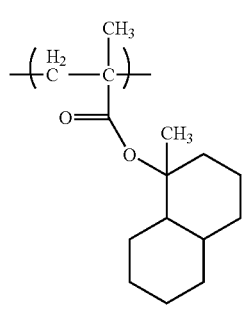
(a1-1-18)
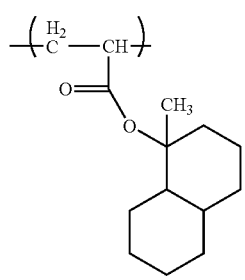
(a1-1-19)
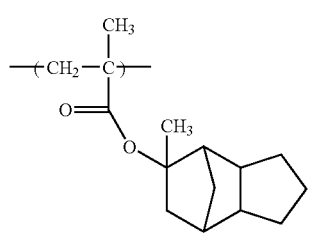
(a1-1-20)
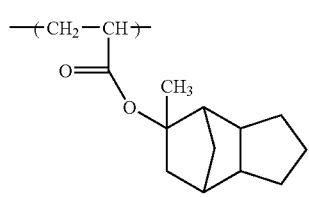
(a1-1-21)
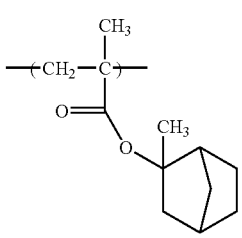
(a1-1-22)
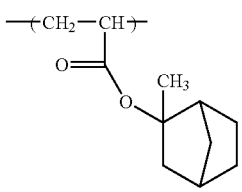
(a1-1-23)
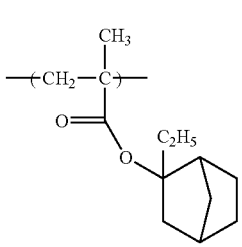
(a1-1-24)
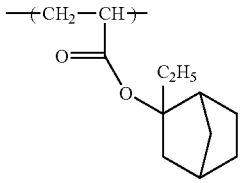
(a1-1-25)
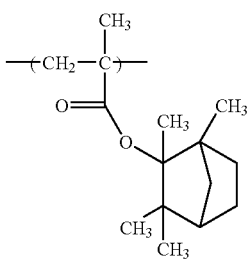
(a1-1-26)
(a1-1-27)
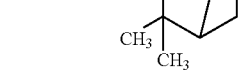

(a1-1-28)
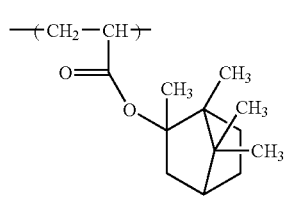
(a1-1-29)
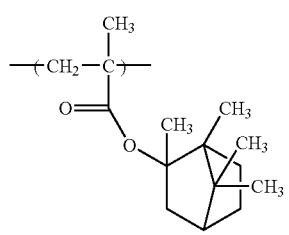
(a1-1-30)
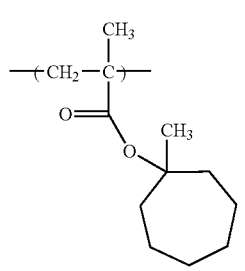
(a1-1-31)
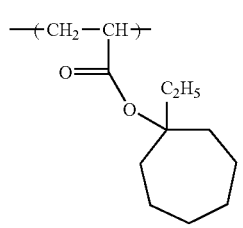
(a1-1-32)
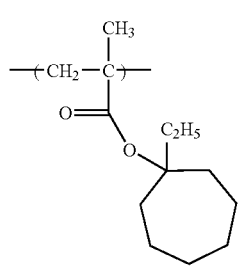
[Chemical Formula 28.]
(a1-1-33)
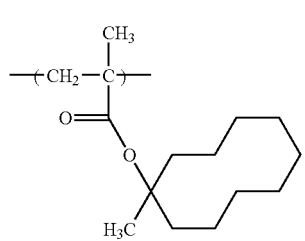
(a1-1-34)
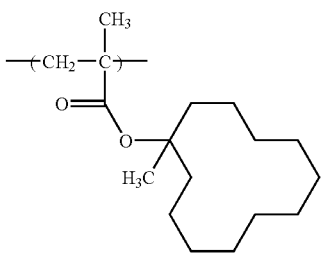
(a1-1-35)
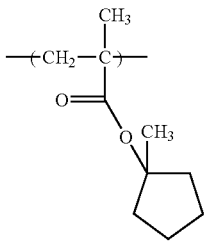
(a1-1-36)
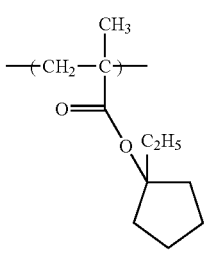
(a1-1-37)
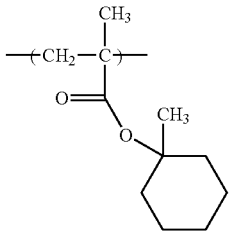
(a1-1-38)
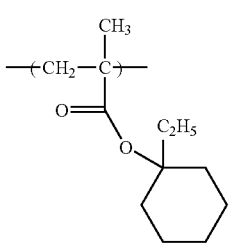
(a1-1-39)
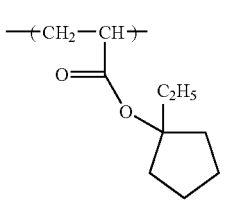
(a1-1-40)

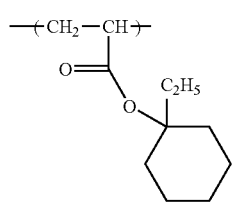 (a1-1-41)
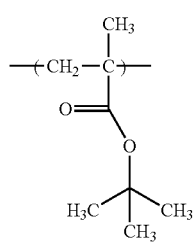 (a1-1-42)
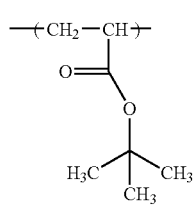 (a1-1-43)
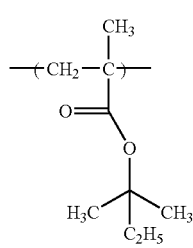 (a1-1-44)
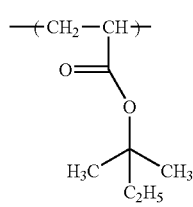 (a1-1-45)
[Chemical Formula 29.]
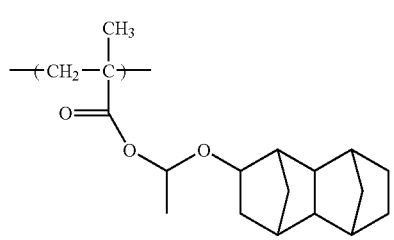 (a1-2-1)
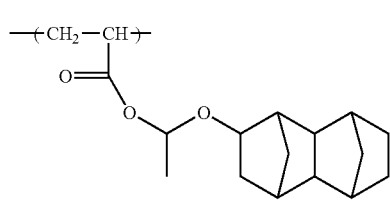 (a1-2-2)
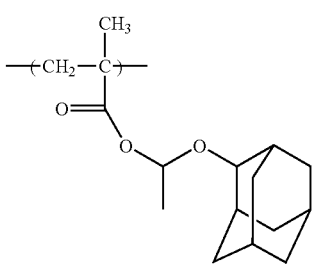 (a1-2-3)
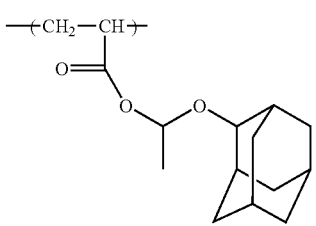 (a1-2-4)
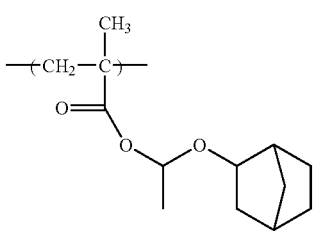 (a1-2-5)
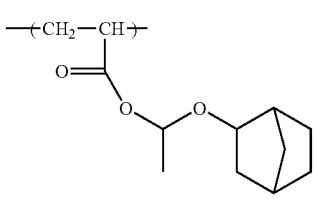 (a1-2-6)
[Chemical Formula 30.]
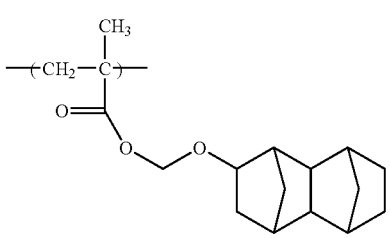 (a1-2-7)
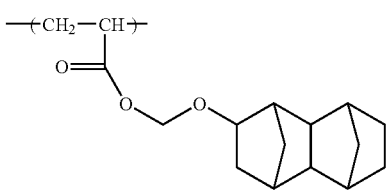 (a1-2-8)
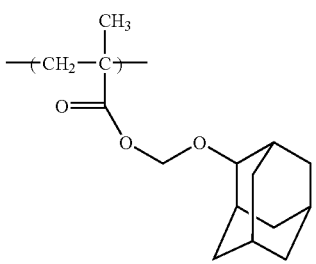 (a1-2-9)

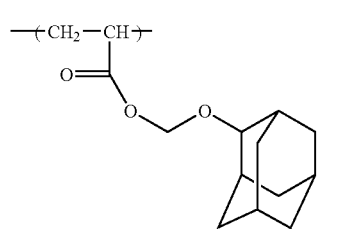 (a1-2-10)
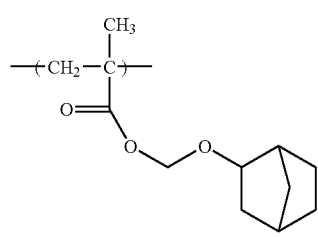 (a1-2-11)
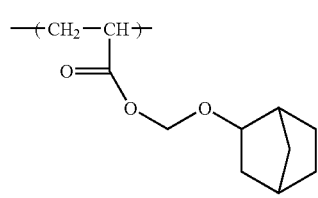 (a1-2-12)
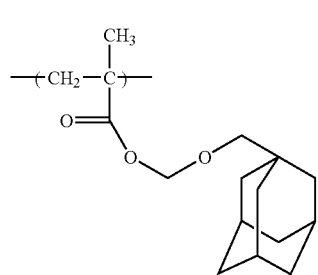 (a1-2-13)
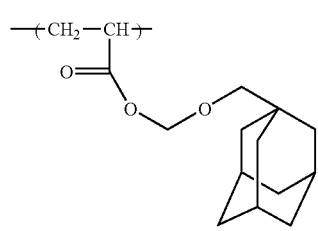 (a1-2-14)
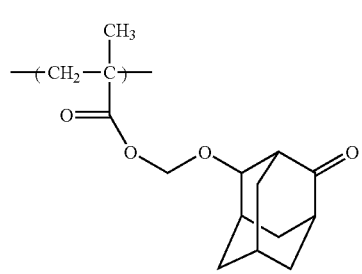 (a1-2-15)
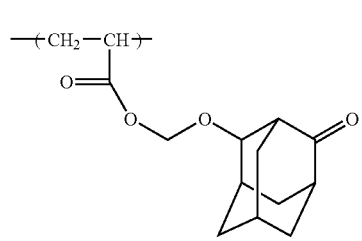 (a1-2-16)
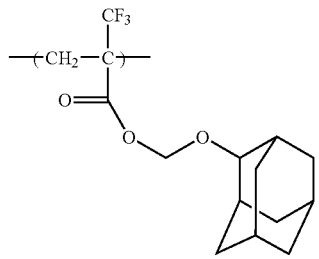 (a1-2-17)
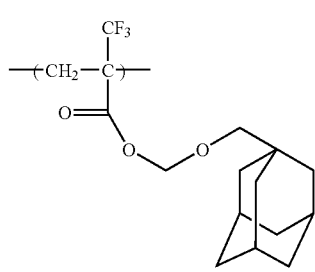 (a1-2-18)
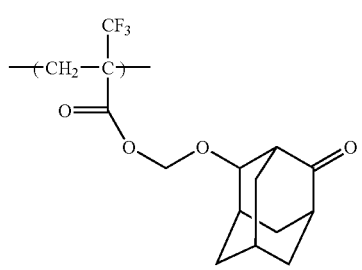 (a1-2-19)
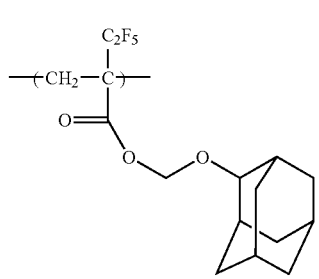 (a1-2-20)
[Chemical Formula 31.]
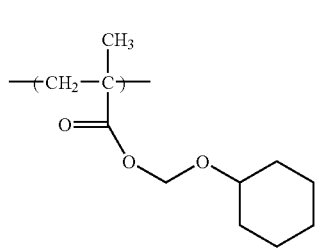 (a1-2-21)
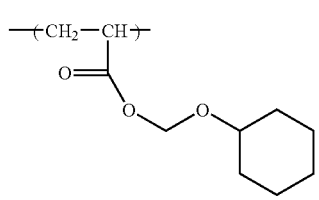 (a1-2-22)

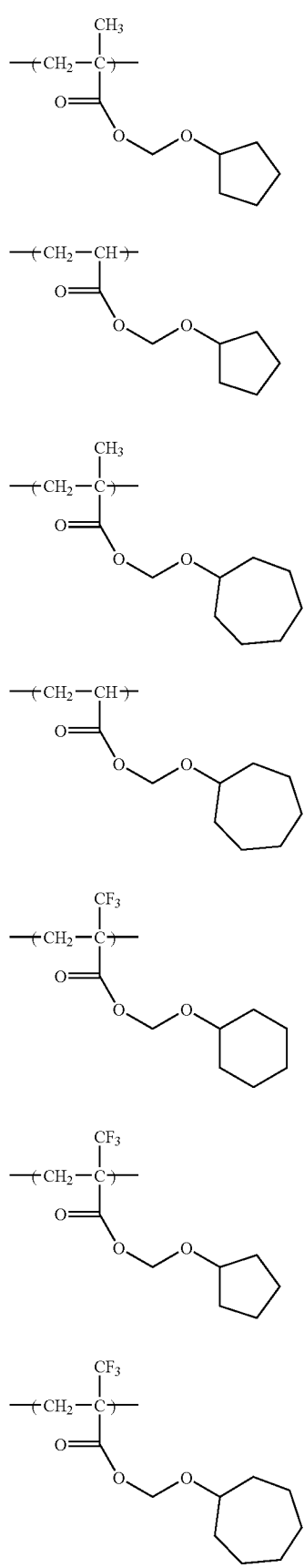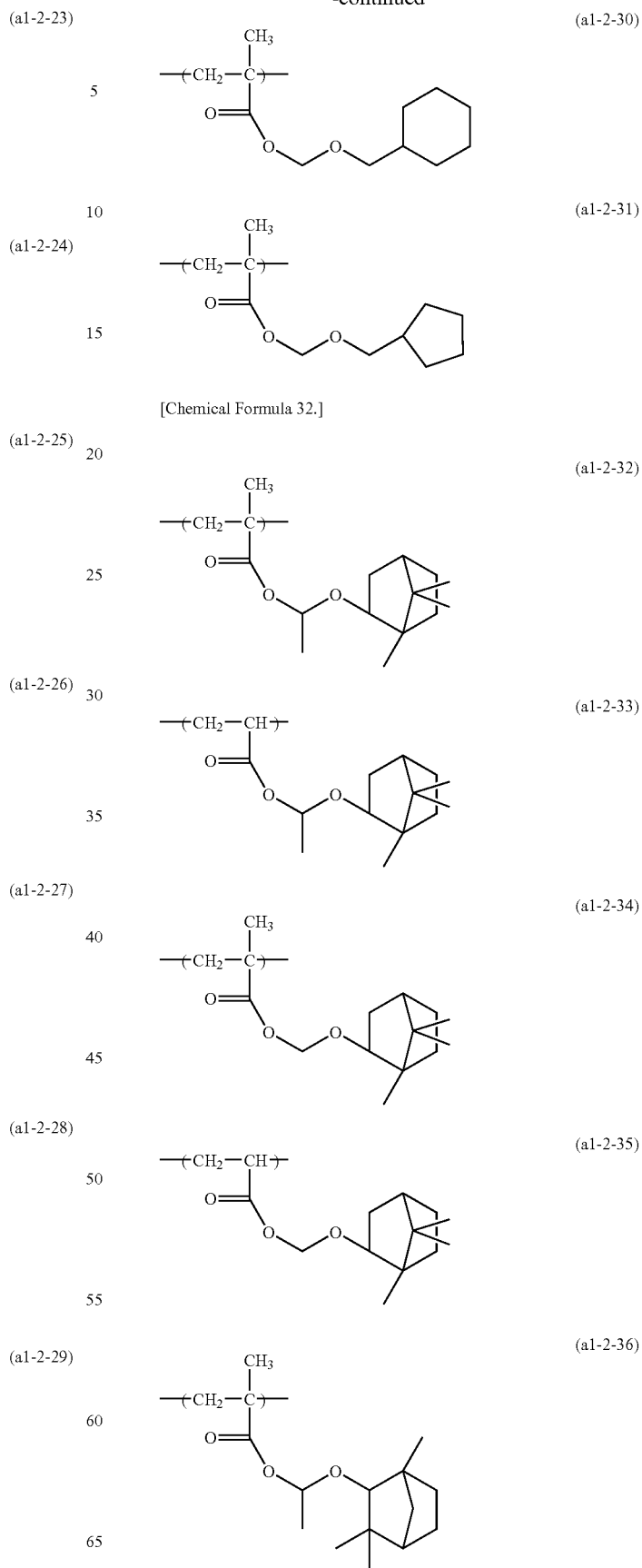

(a1-2-37)
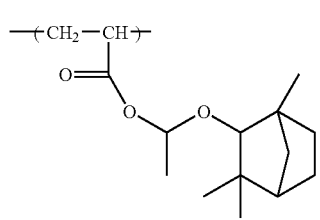
(a1-2-38)
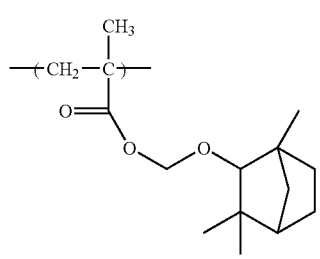
(a1-2-39)
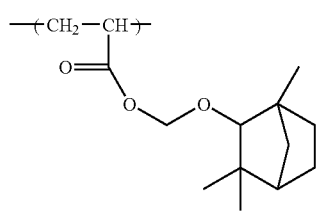
[Chemical Formula 33.]
(a1-3-1)
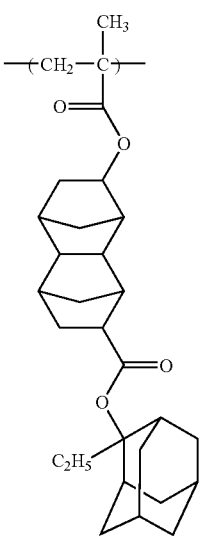
(a1-3-2)
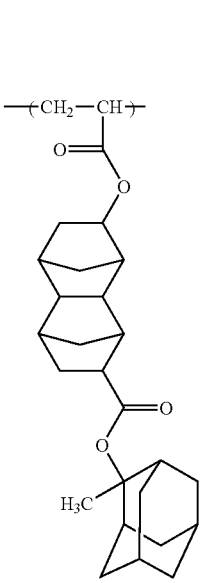
(a1-3-3)
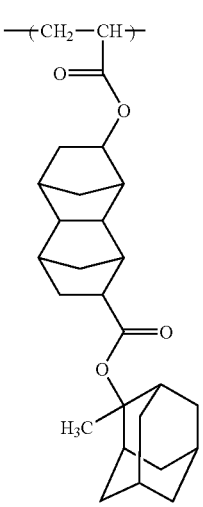
(a1-3-4)
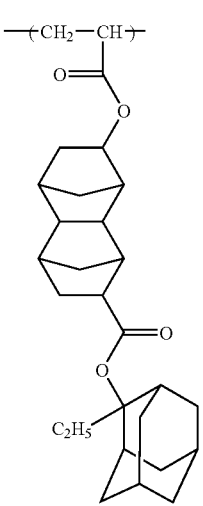

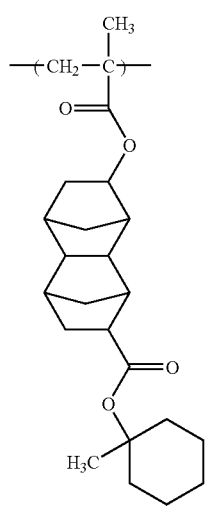
(a1-3-5)
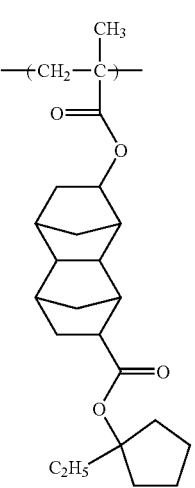
(a1-3-8)
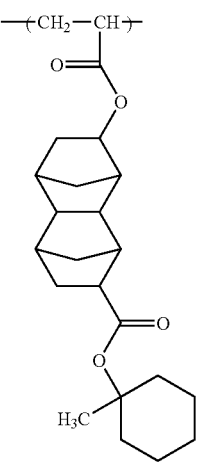
(a1-3-9)
(a1-3-6)
(a1-3-7)
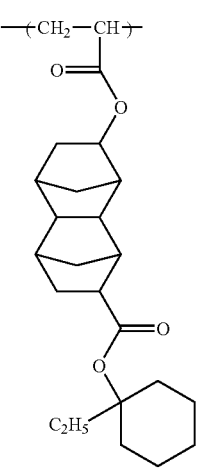
(a1-3-10)

(a1-3-11)
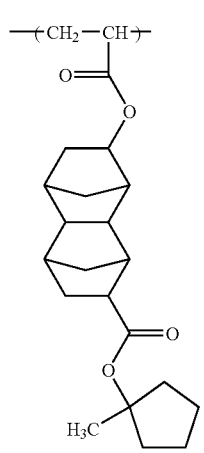
(a1-3-14)
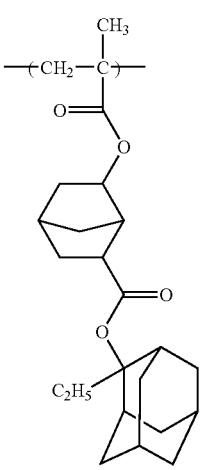
(a1-3-12)
(a1-3-15)
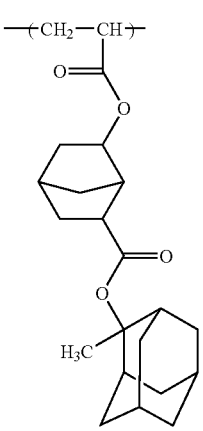
(a1-3-13)
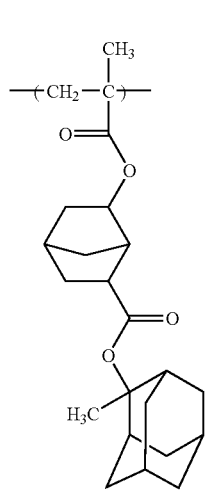
(a1-3-16)
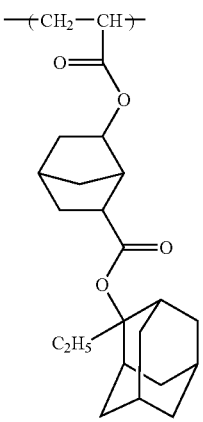

(a1-3-17)
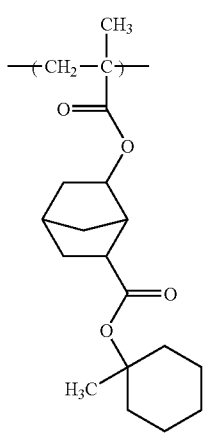
(a1-3-21)
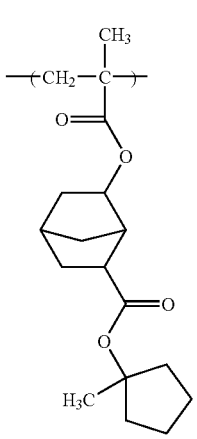
(a1-3-18)
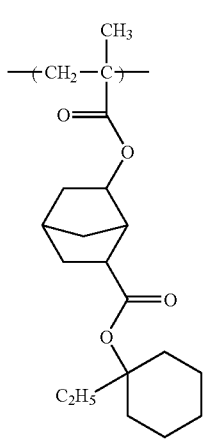
(a1-3-22)
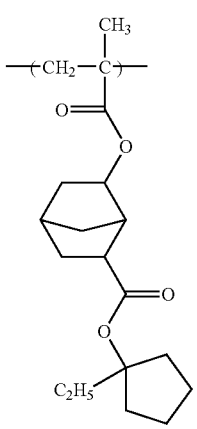
[Chemical Formula 34.]
(a1-3-19)
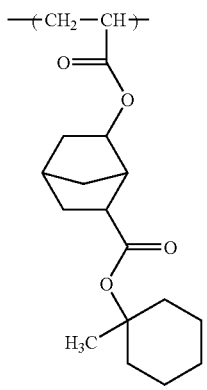
(a1-3-23)
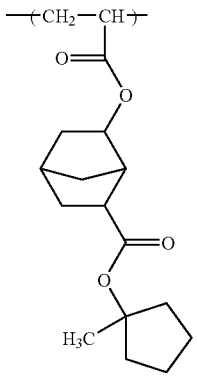
(a1-3-20)
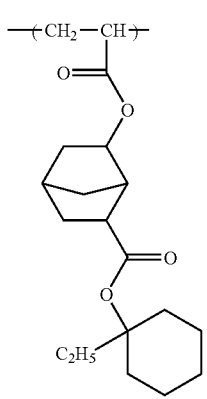
(a1-3-24)
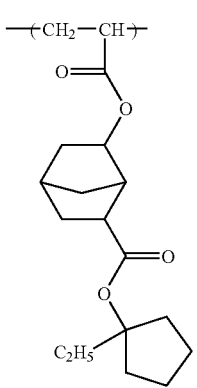

[Chemical Formula 35.]
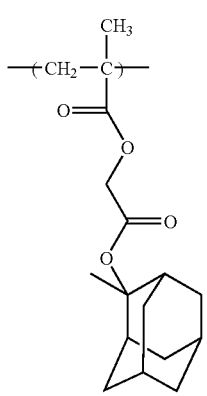 (a1-3-25)
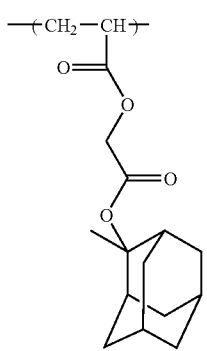 (a1-3-26)
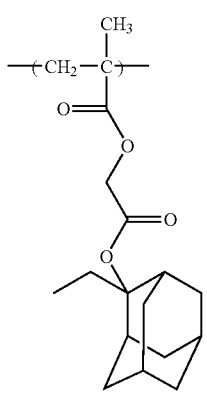 (a1-3-27)
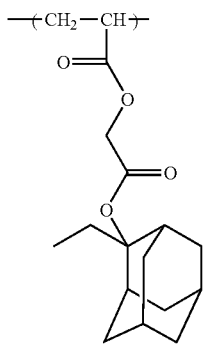 (a1-3-28)
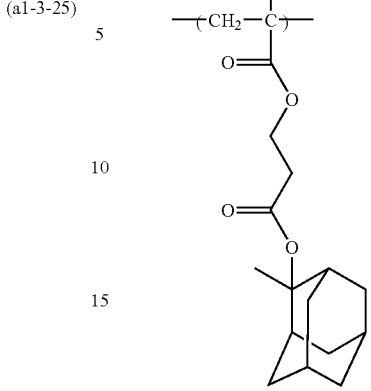 (a1-3-29)
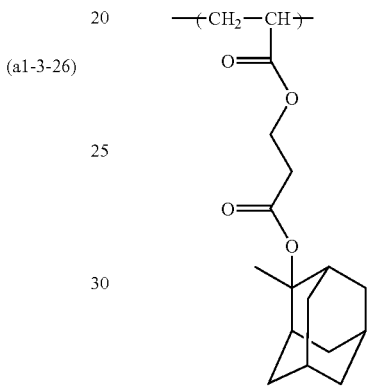 (a1-3-30)
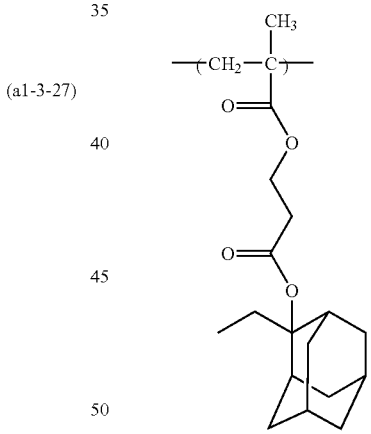 (a1-3-31)
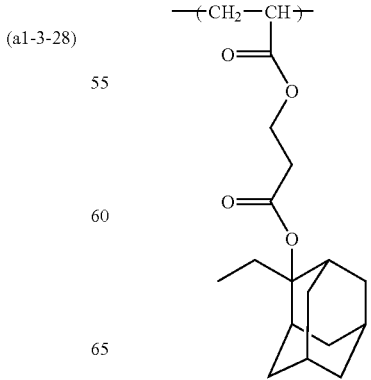 (a1-3-32)

(a1-3-33)
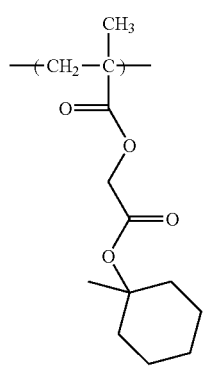
(a1-3-34)
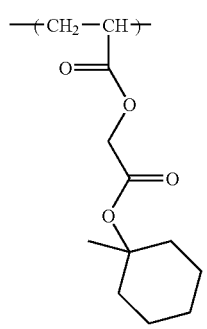
(a1-3-35)
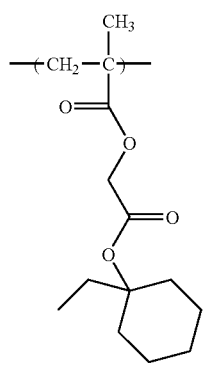
(a1-3-36)
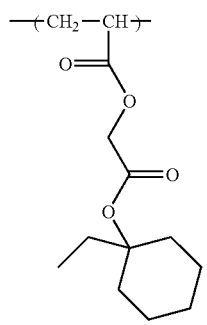
[Chemical Formula 36.]
(a1-3-37)
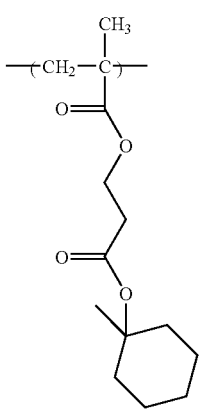
(a1-3-38)
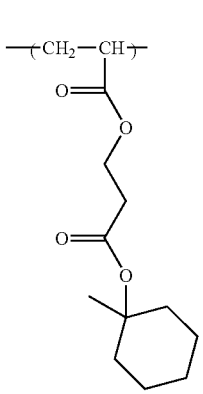
(a1-3-39)
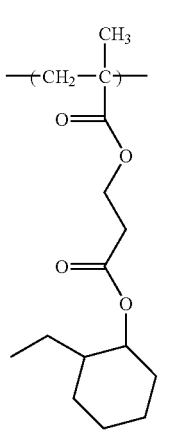
(a1-3-40)
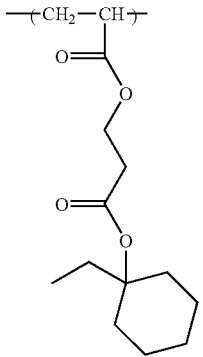

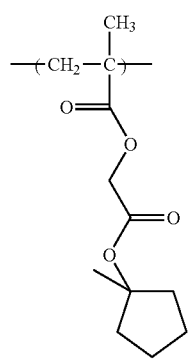
(a1-3-41)
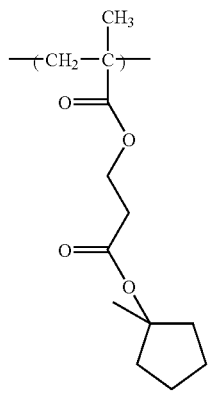
(a1-3-45)
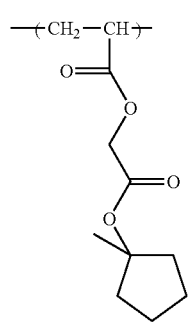
(a1-3-42)
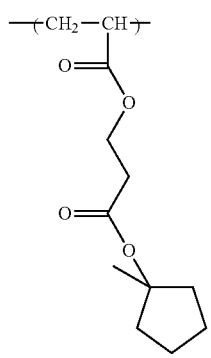
(a1-3-46)
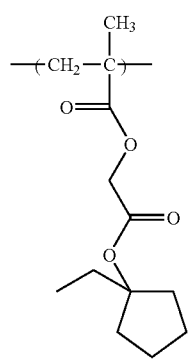
(a1-3-43)
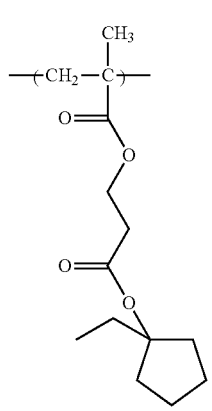
(a1-3-47)
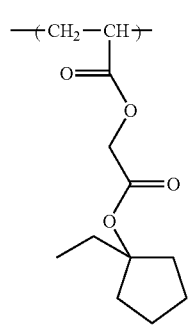
(a1-3-44)
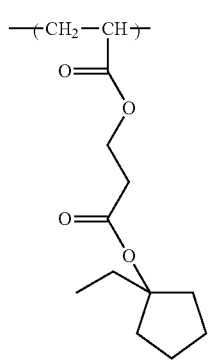
(a1-3-48)

[Chemical Formula 37.]
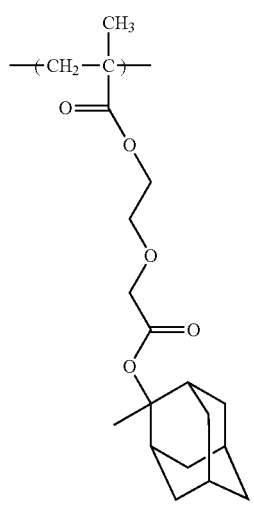
(a1-3-49)
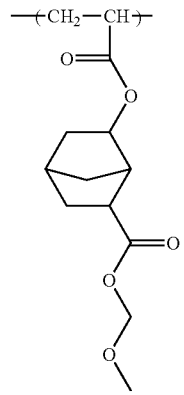
(a1-4-2)
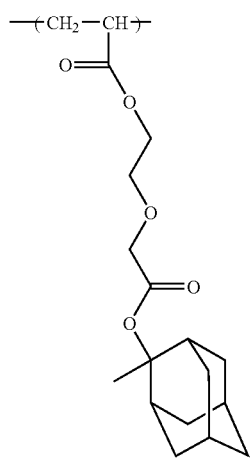
(a1-3-50)
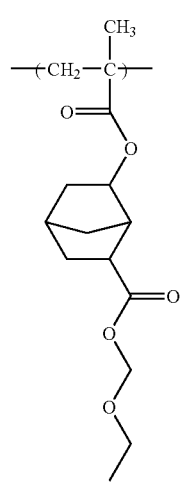
(a1-4-3)
[Chemical Formula 38.]
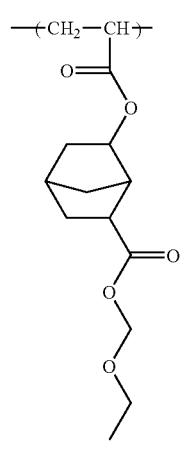
(a1-4-1)
(a1-4-4)

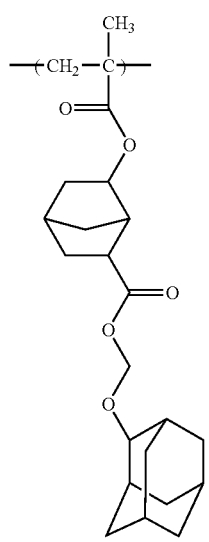 (a1-4-5)
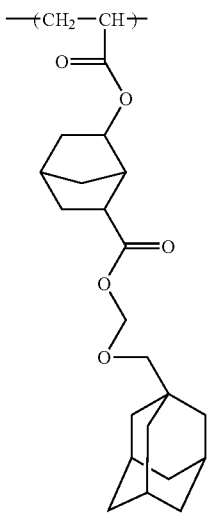 (a1-4-8)
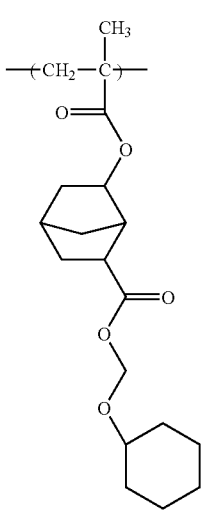 (a1-4-6)
(a1-4-9)
(a1-4-7)
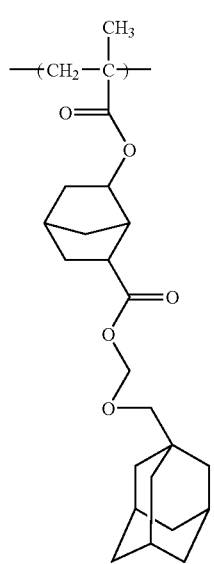 (a1-4-10)

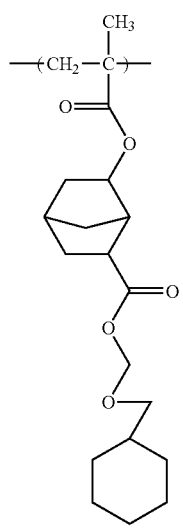 (a1-4-11)
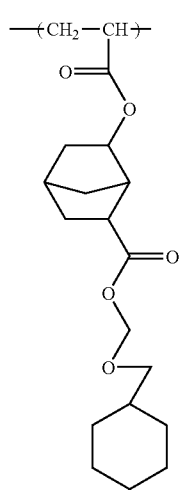 (a1-4-12)
(a1-4-13)
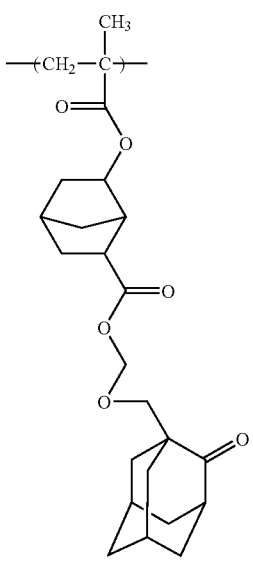 (a1-4-14)
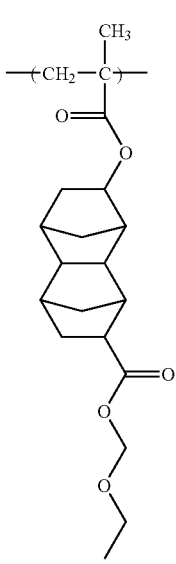 (a1-4-15)
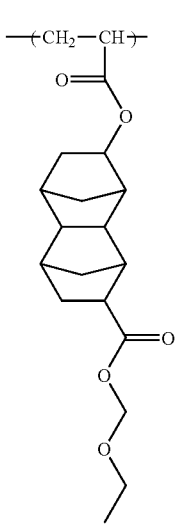 (a1-4-16)

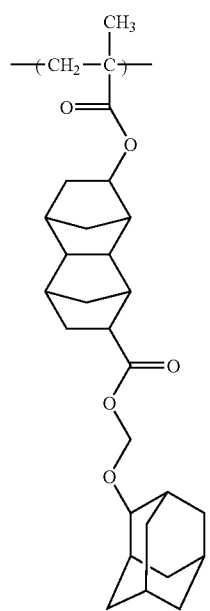
(a1-4-17)
[Chemical Formula 39.]
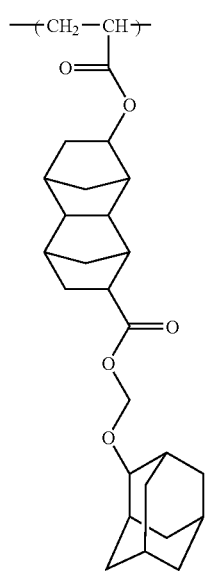
(a1-4-18)
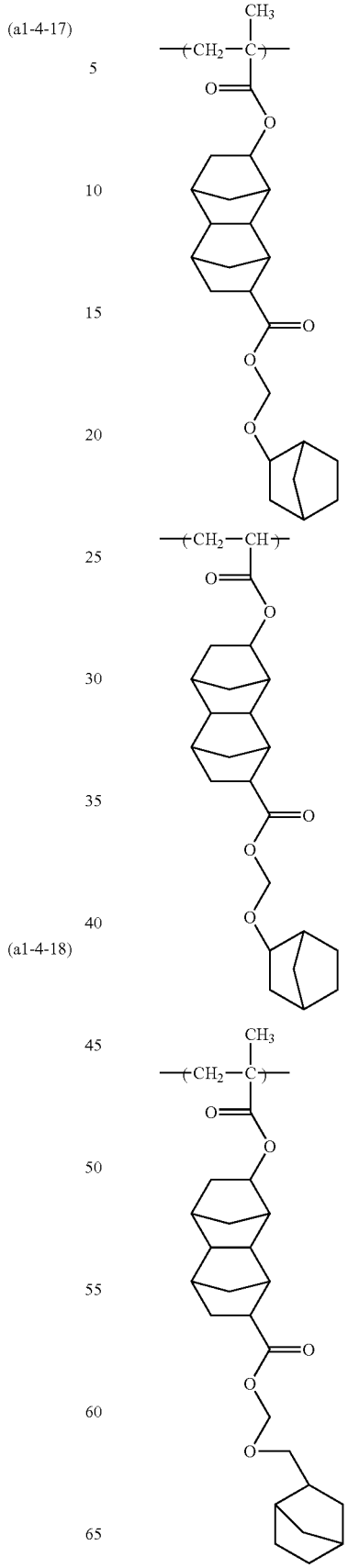
(a1-4-19)
(a1-4-20)
(a1-4-21)

-continued
(a1-4-22)
(a1-4-23)
(a1-4-22) (a1-4-24)
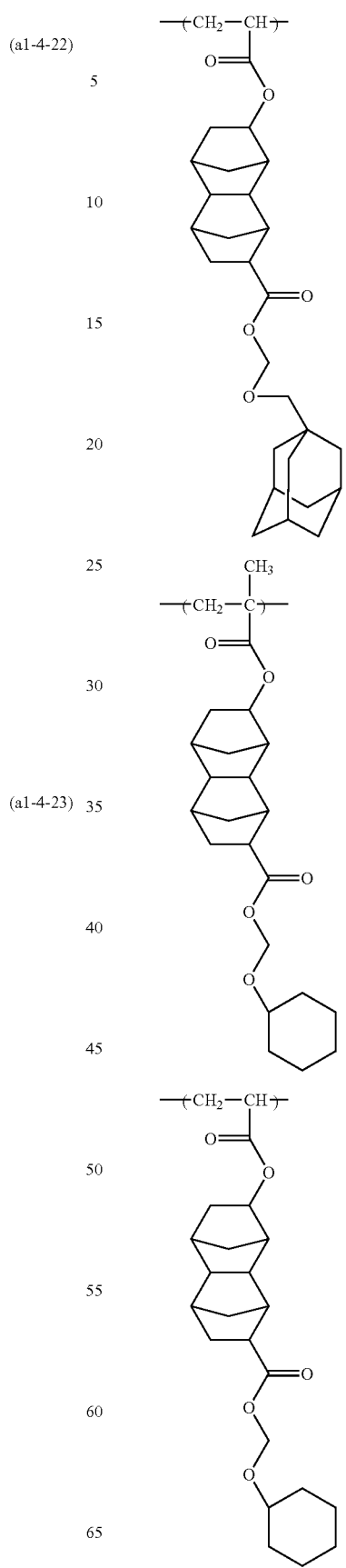
(a1-4-25)
(a1-4-26)

(a1-4-27)

(a1-4-28)

(a1-4-29)
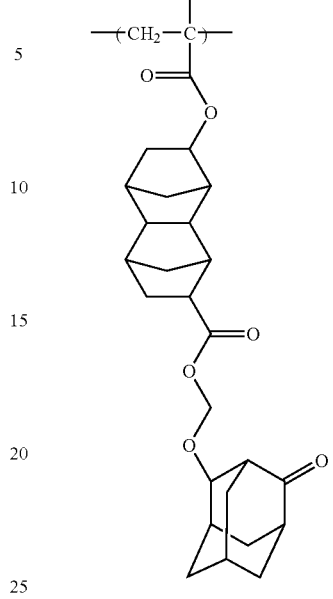

(a1-4-30)
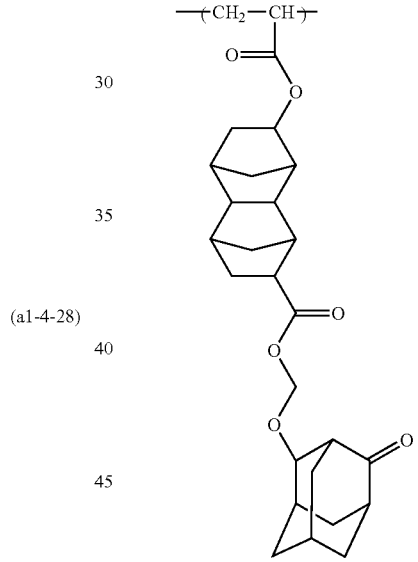

As the structural unit (a1), one type of structural unit may be used alone, or two or more types may be used in combination.

Among these, structural units represented by general formula (a1-1) are preferable. More specifically, at least one structural unit selected from the group consisting of structural units represented by formulas (a1-1-1) to (a-1-1-6), (a1-1-35) to (a1-1-41), (a1-3-49) and (a1-3-50) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 40.]

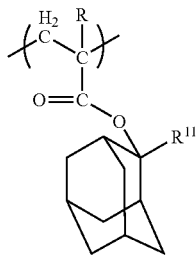

(a1-1-01)

wherein R represents a hydrogen atom, a lower alkyl group or a halogenated lower alkyl group; and $R^{11}$ represents a lower alkyl group.

[Chemical Formula 41.]

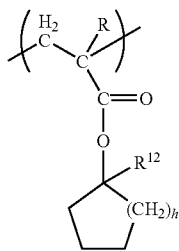

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, and is preferably a methyl group or an ethyl group.

In general formula (a1-1-02), R is as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

As the structural unit (a1), one type of structural unit may be used alone, or two or more types may be used in combination.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the component (A1). On the other hand, by making the amount of the structural unit (a1) no more than the upper limit of the above-mentioned range, a good balance can be achieved with the other structural units.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemial Formula 42.]

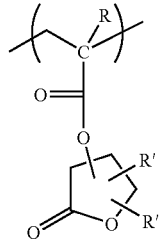

(a2-1)

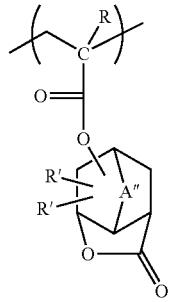

(a2-2)

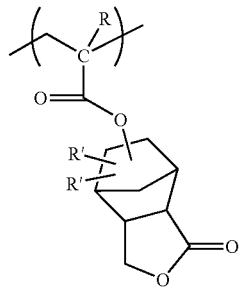

(a2-3)

-continued

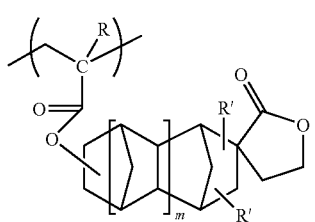
(a2-4)

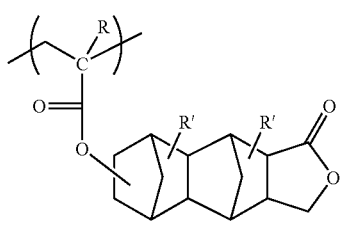
(a2-5)

wherein R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents 0 or 1; and A" represents an alkylene group of 1 to 5 carbon atoms which may contain an oxygen atom or a sulfur atom, an oxygen atom, or a sulfur atom.

In general formulas (a2-1) to (a2-5), R is the same as R in the structural unit (a1).

The lower alkyl group for R' is the same as the lower alkyl group for R in the structural unit (a1).

When R" is a linear or branched alkyl group, it preferably has 1 to 10 carbon atoms, more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

In the structural units represented by general formulas (a2-1) to (a2-5), in consideration of industrial availability, R' is preferably a hydrogen atom.

As specific examples of the alkylene group of 1 to 5 carbon atoms for A" which may contain an oxygen atom or a sulfur atom, a methylene group, an ethylene group, an n-propylene group, an isopropylene group, —O—CH$_2$—, —CH$_2$—O—CH$_2$—, —S—CH$_2$— and —CH$_2$—S—CH$_2$— can be mentioned.

Specific examples of structural units represented by general formulas (a2-1) to (a2-5) above are shown below.

[Chemical Formula 43.]

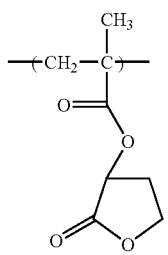
(a2-1-1)

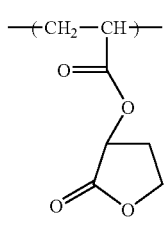
(a2-1-2)

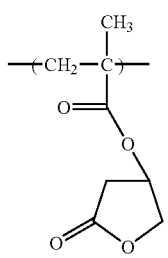
(a2-1-3)

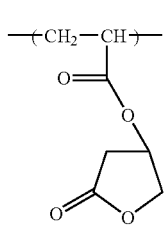
(a2-1-4)

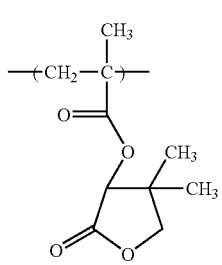
(a2-1-5)

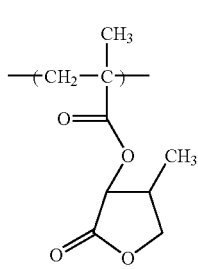
(a2-1-6)

-continued
[Chemical Formula 44.]
(a2-2-1) 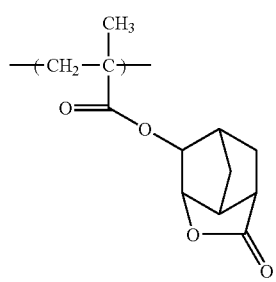
(a2-2-2) 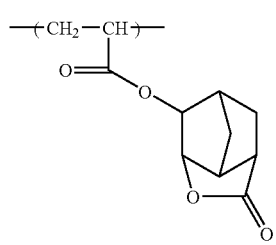
(a2-2-3) 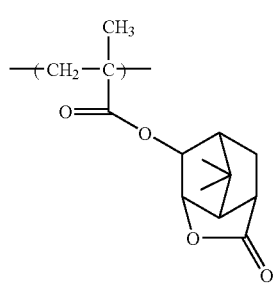
(a2-2-4) 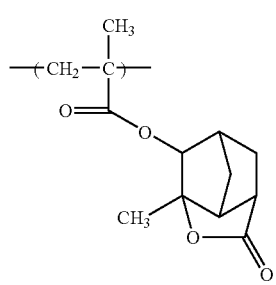
(a2-2-5) 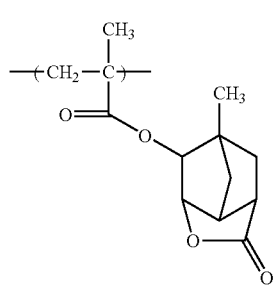
(a2-2-6) 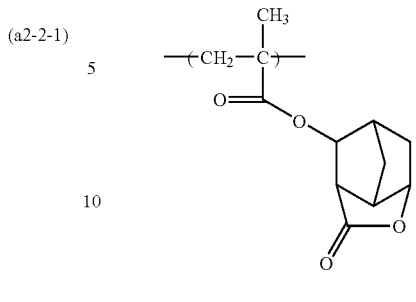
(a-2-2-7) 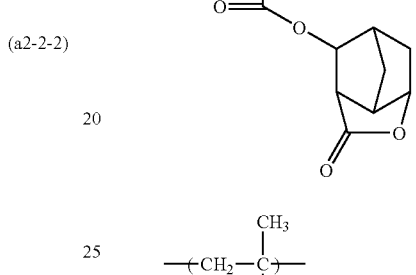
(a2-2-8) 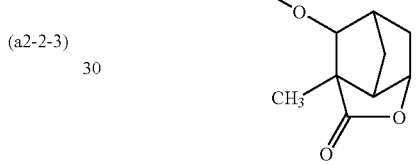
(a2-2-9) 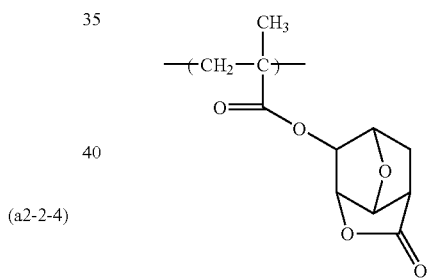
(a2-2-10) 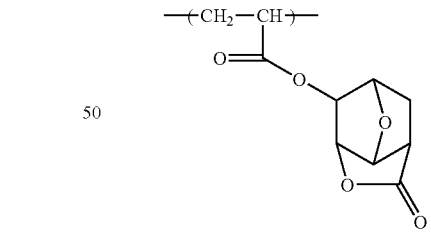
(a2-2-11) 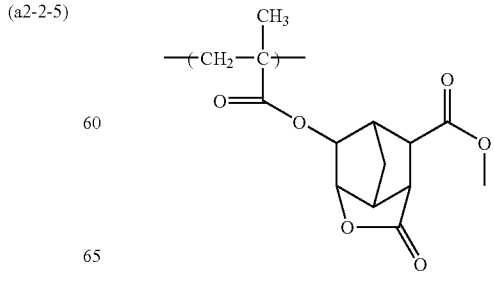

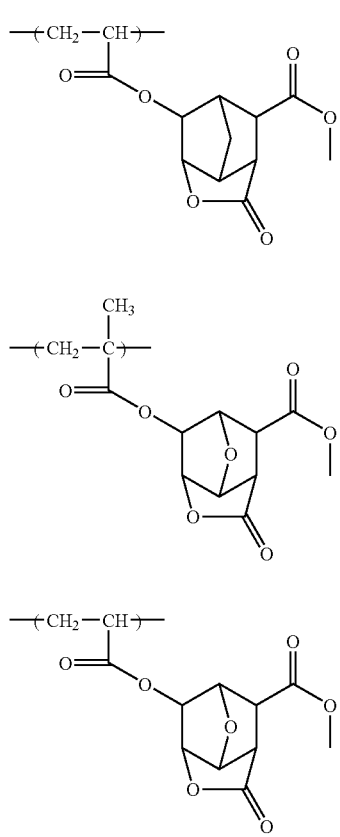
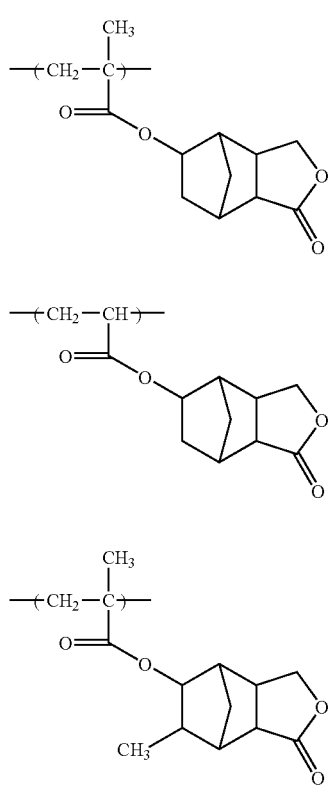
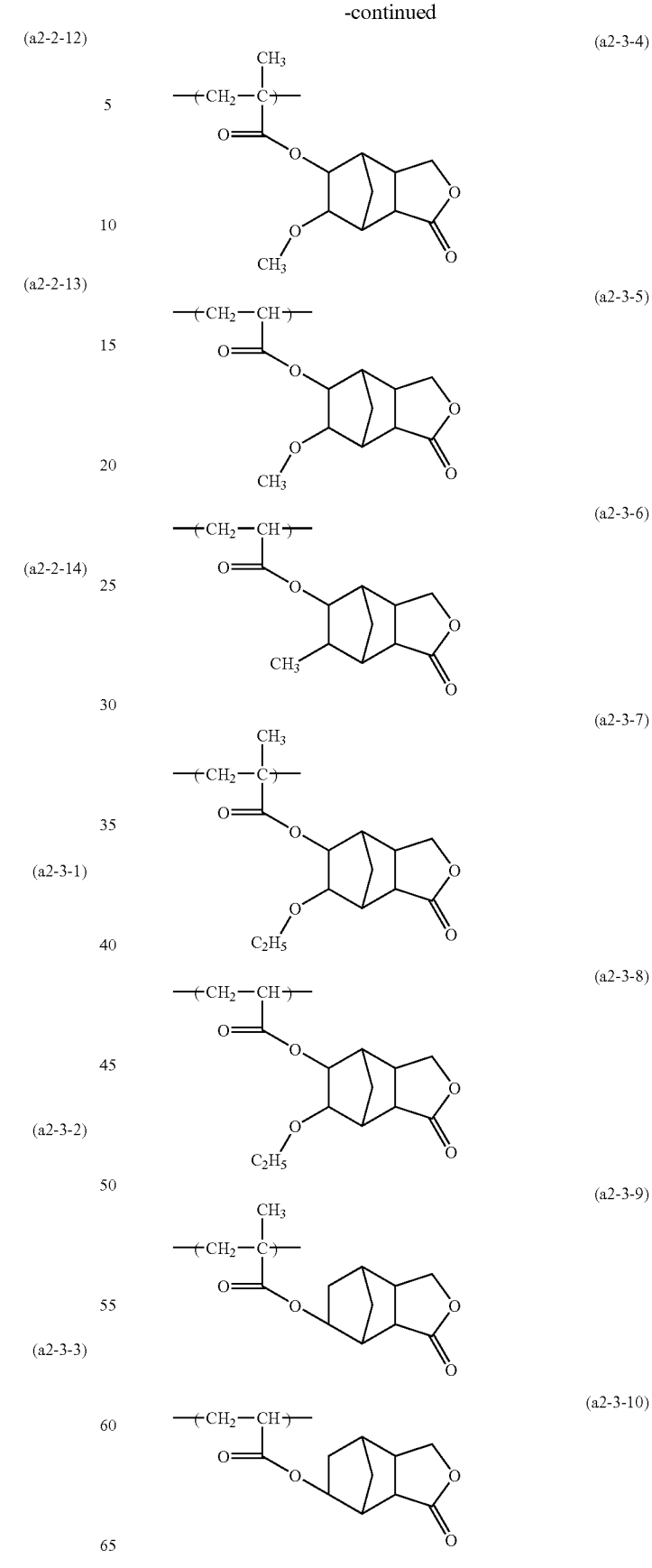

[Chemical Formula 46.]
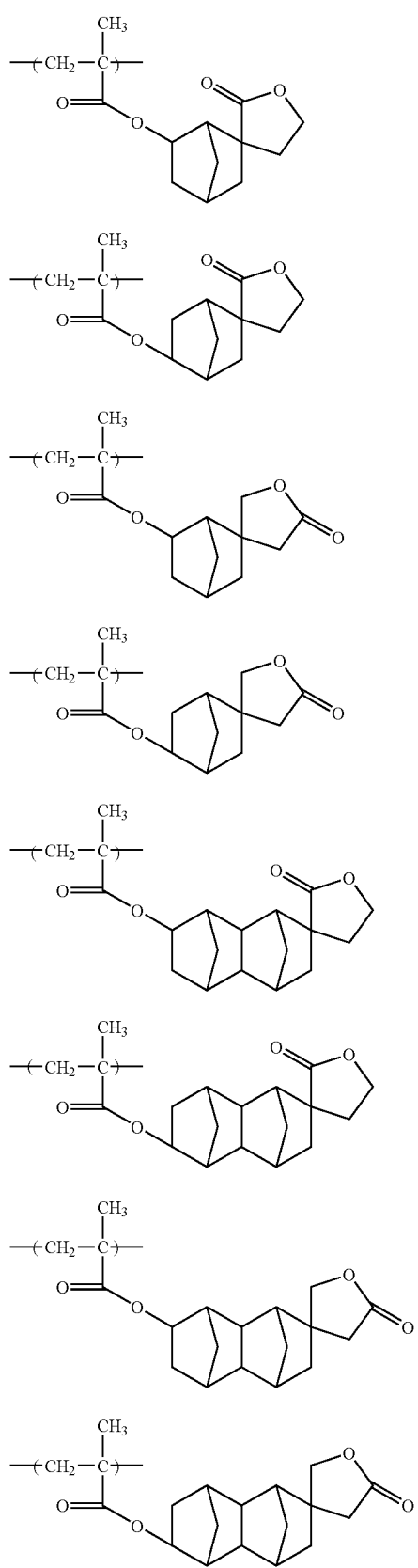
(a2-4-1)
(a2-4-2)
(a2-4-3)
(a2-4-4)
(a2-4-5)
(a2-4-6)
(a2-4-7)
(a2-4-8)
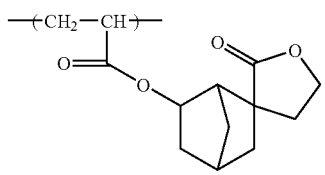
(a2-4-9)
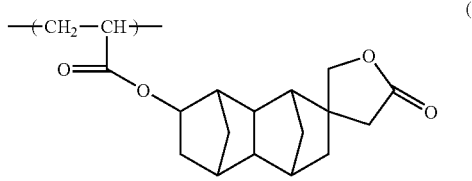
(a2-4-10)
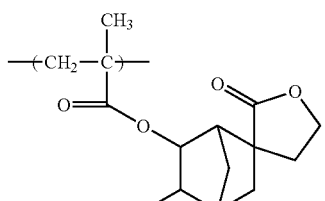
(a2-4-11)
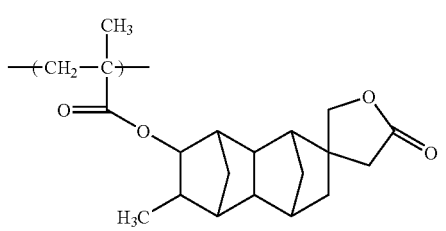
(a2-4-12)
[Chemical Formula 47.]
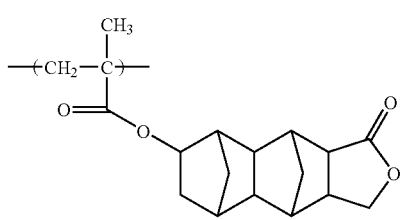
(a2-5-1)
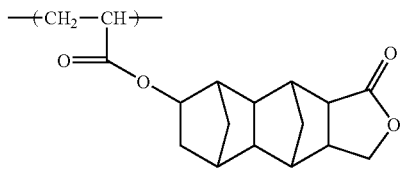
(a2-5-2)
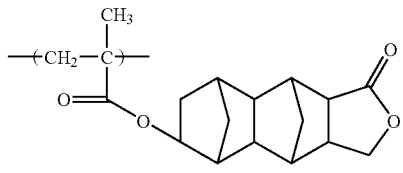
(a2-5-3)
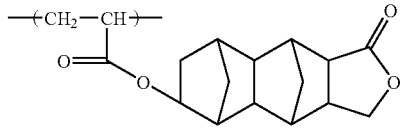
(a2-5-4)

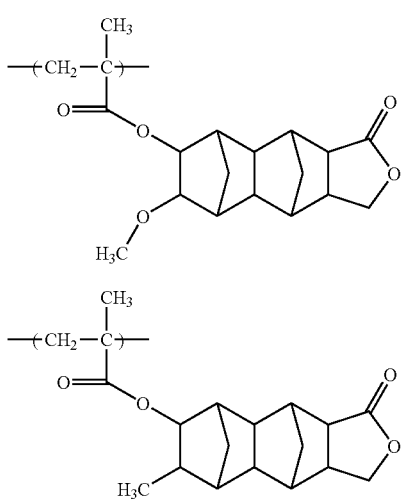

(a2-5-5)

(a2-5-6)

As the structural unit (a2), at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-2-1), (a2-2-2), (a2-2-9), (a2-2-10), (a2-3-1), (a2-3-2), (a2-3-9) and (a2-3-10).

As the structural unit (a2), one type of structural unit may be used, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A1) is improved, and hence, the compatibility of the component (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 48.]

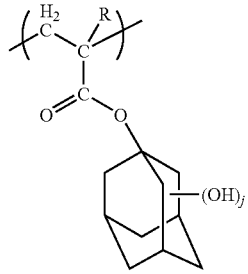

(a3-1)

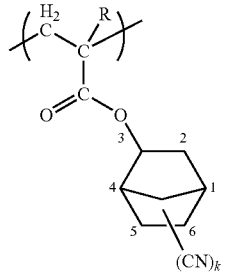

(a3-2)

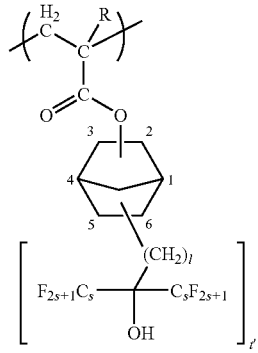

(a3-3)

wherein R is as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbonyl group.

In formula (a3-3), t' is preferably 1, l is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbonyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 49.]

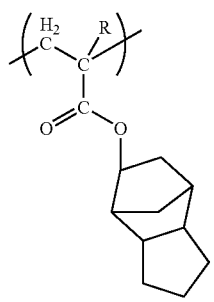

(a4-1)

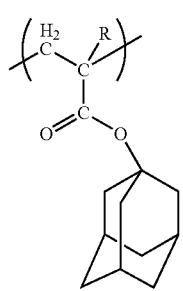

(a4-2)

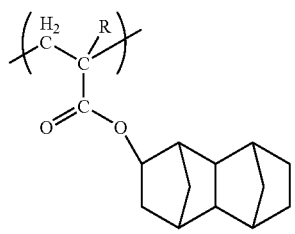

(a4-3)

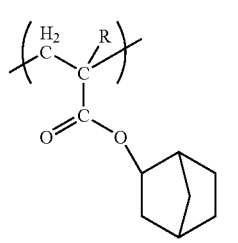

(a4-4)

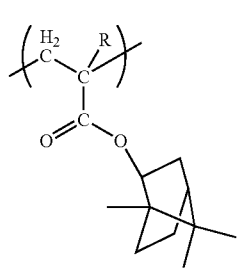

(a4-5)

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) preferably contains a copolymer having the structural units (a1), (a2) and (a3). Examples of such a copolymer include a copolymer consisting of the structural units (a1) and (a2) and (a3), and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—CH$_2$—CH$_2$—CH$_2$—C(CF$_3$)$_2$—OH, a —C(CF$_3$)$_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferable to use a compound that has a molecular weight of at least 500 and less than 2,000, contains a hydrophilic group, and also contains an acid dissociable, dissolution inhibiting group mentioned above in connection with the component (A1). Specific examples include compounds containing a plurality of phenol skeletons in which a part of the hydrogen atoms within hydroxyl groups have been substituted with the aforementioned acid dissociable, dissolution-inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (A), one type may be used, or two or more types may be used in combination.

In the resist composition of the present invention, the amount of the component (A) can be appropriately adjusted depending on the thickness of the resist film to be formed, and the like.

<Component (B)>

The component (B) includes an acid generator (B1) (hereafter, referred to as "component (B1)") consisting of a compound represented by general formula (b1-1) above. The component (B1) is the same as the aforementioned compound (B1) of the present invention.

As the component (B1), one type may be used, or two or more types may be used in combination.

In the resist composition of the present invention, the amount of the component (B1) within the component (B) is preferably 40% by weight or more, more preferably 70% by weight or more, and may be even 100% by weight. It is particularly desirable that the amount of the component (B1) within the component (B) be 100% by weight. By making the amount of the component (B1) at least as large as the lower limit of the above-mentioned range, lithography properties such as resolution, mask reproducibility and line width roughness are improved when a resist pattern is formed using the resist composition of the present invention.

In the component (B), an acid generator (B2) other than the aforementioned component (B1) (hereafter, referred to as "component (B2)") may be used in combination with the component (B1).

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator a compound represented by general formula (b-1) or (b-2) shown below can be preferably used.

[Chemical Formula 50.]

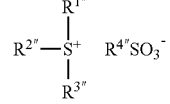

(b-1)

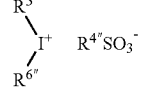

(b-2)

wherein R$^{1"}$ to R$^{3"}$, R$^{5"}$ and R$^{6"}$ each independently represents an aryl group or alkyl group, wherein two of R$^{1"}$ to R$^{3"}$ in formula (b-1) may be bonded to each other to form a ring with the sulfur atom; and R$^{4"}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ in formula (b-1) may be bonded to each other to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used in which some or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group, ethoxy group, n-propoxy group, iso-propoxy group, n-butoxy group or tert-butoxy group.

The alkoxy group, with which hydrogen atoms of the aryl group may be substituted, is preferably an alkoxy group having 1 to 5 carbon atoms, and most preferably a methoxy group or an ethoxy group The halogen atom, with which hydrogen atoms of the aryl group may be substituted, is preferably a fluorine atom.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{1\prime\prime}$ to $R^{3\prime\prime}$ is a phenyl group or a naphthyl group.

When two of $R^{1\prime\prime}$ to $R^{3\prime\prime}$ in formula (b-1) are bonded to each other to form a ring with the sulfur atom, it is preferable that the two of $R^{1\prime\prime}$ to $R^{3\prime\prime}$ form a 3 to 10-membered ring including the sulfur atom, and it is particularly desirable that the two of $R^{1\prime\prime}$ to R3" form a 5 to 7-membered ring including the sulfur atom. When two of $R^{1\prime\prime}$ to $R^{3\prime\prime}$ in formula (b-1) are bonded to each other to form a ring with the sulfur atom, the remaining one of $R^{1\prime\prime}$ to $R^{3\prime\prime}$ is preferably an aryl group. As examples of the aryl group, the same aryl groups as those for $R^{1\prime\prime}$ to $R^{3\prime\prime}$ can be mentioned.

$R^{4\prime\prime}$ represents a linear, branched or cyclic alkyl or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1}-$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (percentage of fluorine atoms within the alkyl group) is preferably from 10 to 100%, more preferably from 50 to 100%, and a fluorinated alkyl group in which all hydrogen atoms are substituted with fluorine atoms (i.e., a perfluoroalkyl group) is particularly desirable because the acid strength increases.

$R^{4\prime\prime}$ is most preferably a linear or cyclic alkyl group or fluorinated alkyl group.

In formula (b-2), $R^{5\prime\prime}$ and $R^{6\prime\prime}$ each independently represents an aryl group or alkyl group. At least one of $R^{5\prime\prime}$ and $R^{6\prime\prime}$ represents an aryl group. It is preferable that both of $R^{5\prime\prime}$ and $R^{6\prime\prime}$ represent an aryl group.

As the aryl group for $R^{5\prime\prime}$ and $R^{6\prime\prime}$, the same aryl groups as those for $R^{1\prime\prime}$ to $R^{3\prime\prime}$ can be mentioned.

As the alkyl group for $R^{5\prime\prime}$ and $R^{6\prime\prime}$, the same alkyl groups as those for $R^{1\prime\prime}$ to $R^{3\prime\prime}$ can be mentioned.

It is particularly desirable that both of $R^{5\prime\prime}$ and $R^{6\prime\prime}$ represent a phenyl group.

As $R^{4\prime\prime}$ in formula (b-2), the same as those mentioned above for $R^{4\prime\prime}$ in formula (b-1) can be mentioned.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 51.]

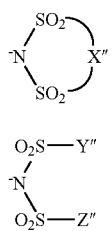

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

Furthermore, as an onium salt-based acid generator, a sulfonium salt having a cation moiety represented by general formula (b-5') or (b-6') shown below may be used.

[Chemical Formula 52.]

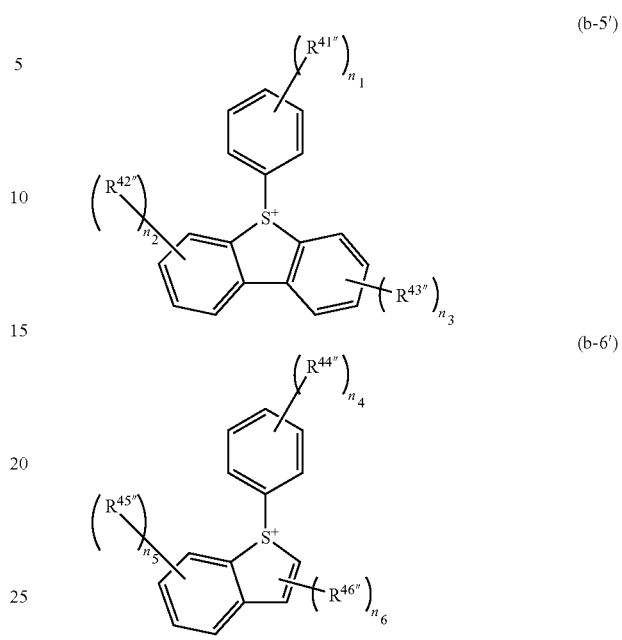

wherein $R^{41\prime\prime}$ to $R^{46\prime\prime}$ each independently represents an alkyl group, an acetyl group, an alkoxy group, a carboxy group, a hydroxyl group or a hydroxyalkyl group; $n_1$ to $n_5$ each independently represents an integer of 0 to 3; and $n_6$ represents an integer of 0 to 2.

With respect to $R^{41\prime\prime}$ to $R^{46\prime\prime}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

When the subscripts $n_1$ to $n_6$ of $R^{41\prime\prime}$ to $R^{46\prime\prime}$ represent an integer of 2 or more, the plurality of $R^{41\prime\prime}$ to $R^{46\prime\prime}$ may be the same or different.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5') or (b-6') is not particularly limited, and the same anion moieties for onium salt-based acid generators which have been proposed may be used. Examples of such anion moieties include fluorinated alkylsulfonic acid ions such as anion moieties ($R^{4\prime\prime}SO_3^-$) for onium salt-based acid generators represented by general formula (b-1) or (b-2) shown above; and anion moieties represented by general formula (b-3) or (b-4) shown above.

Among these, a fluorinated alkylsulfonic acid ion is preferable, a fluorinated alkylsulfonic acid ion of 1 to 4 carbon atoms is more preferable, and a linear perfluoroalkylsulfonic acid ion of 1 to 4 carbon atoms is particularly desirable. Specific examples include a trifluoromethylsulfonic acid ion, a heptafluoro-n-propylsulfonic acid ion and a nonafluoro-n-butylsulfonic acid ion.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 53.]

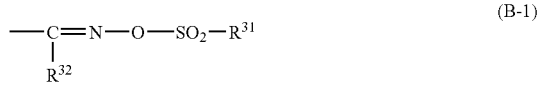

(B-1)

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 54.]

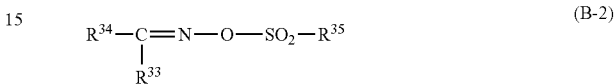

(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 55.]

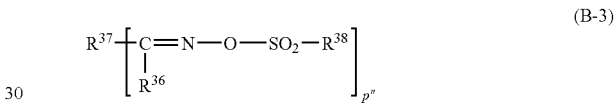

(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be mentioned.

[Chemical Formula 56.]

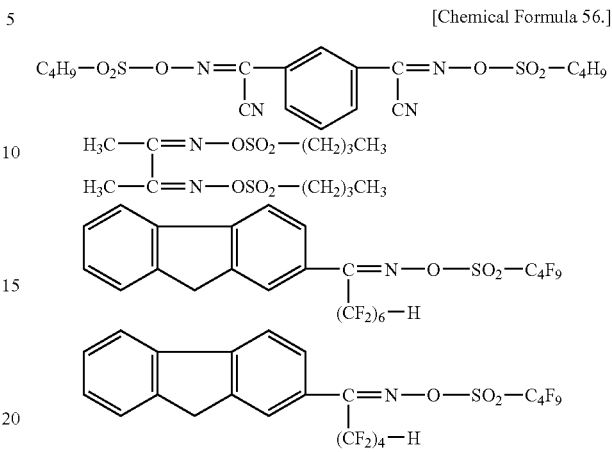

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be mentioned.

As the component (B2), one type of acid generator may be used, or two or more types may be used in combination.

The total amount of the component (B) within the resist composition of the present invention is typically 0.5 to 30 parts by weight, and preferably 1 to 20 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Component (D)>

In the resist composition of the present invention, for improving the resist pattern shape and the post exposure stability of the latent image formed by the pattern-wise exposure of the resist layer, it is preferable to add a nitrogen-containing organic compound (D) (hereafter referred to as the component (D)).

A multitude of these components (D) have already been proposed, and any of these known compounds may be used, although an aliphatic amine, and particularly a secondary aliphatic amine or tertiary aliphatic amine is preferable. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines in which three alkyl groups of 5 to 10 carbon atoms are bonded to the nitrogen atom are preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.01]-5-nonene, 1,8-diazabicyclo[5.4.01]-7-undecene, hexamethylenetetramine, and 1,4-diazabicyclo[2.2.2]octane.

Apart from the nitrogen-containing organic compounds mentioned above, stearyldiethanolamine or lauryldiethanolamine can also be preferably used.

These compounds can be used either alone, or in combinations of two or more different compounds.

The component (D) is typically used in an amount within a range from 0.01 to 5.0 parts by weight, relative to 100 parts by weight of the component (A).

<Optional Components>

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the materials for the resist composition in an organic solvent (S) (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as y-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

<<Method of Forming a Resist Pattern>>

The method of forming a resist pattern according to the second aspect of the present invention includes: applying a resist composition according to the first aspect of the present invention to a substrate to form a resist film on the substrate; conducting exposure of the resist film; and alkali-developing the resist film to form a resist pattern.

More specifically, the method for forming a resist pattern according to the present invention can be performed, for example, as follows. Firstly, a resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, alkali developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the alkali developing. In this manner, a resist pattern that is faithful to the mask pattern can be obtained.

The substrate is not specifically limited and a conventionally known substrate can be used. For example, substrates for electronic components, and such substrates having wiring patterns formed thereon can be mentioned. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be mentioned. As the organic film, an organic antireflection film (organic BARC) can be mentioned.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The positive resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

The resist composition of the present invention is a novel composition which was conventionally unknown.

By the resist composition of the present invention, a resist pattern exhibiting excellent lithography properties with respect to mask reproducibility (e.g., mask linearity, circularity of the holes of a hole pattern, and the like). The reason for this has not been elucidated yet, but is presumed as follows.

In the resist composition of the present invention, the aforementioned component (B1) is used as an acid generator.

The anion moiety of the component (B1) has a structure in which the skeleton "$Y^1$—$SO_3^-$" has a bulky ring of 3 to 30 carbon atoms having the group "—$SO_2$—" on the ring skeleton thereof bonded through "-$Q^1$-". As a result, the anion moiety of the component (B1) exhibits a high polarity and has a three-dimensionally bulky structure, as compared to a fluorinated alkylsulfonic ion which has been conventionally used as an anion moiety. By virtue of the intermolecular force due to the high polarity, and the three-dimensionally bulky structure, it is presumed that diffusion of the anion moiety within the resist film is chemically and physically suppressed, as compared to the anion moiety of a conventional acid generator such as nonafluorobutanesulfonate. Therefore, by using the component (B1), diffusion of the acid generated in the exposed regions to the unexposed regions can be suppressed, and hence, the difference in alkali solubility between the exposed regions and the unexposed regions (i.e., dissolution contrast) can be improved, and it is presumed that resist pattern shapes can be improved.

Further, for the same reason as described above, improvement in the exposure margin (EL margin) is also expected. The EL margin is the range of the exposure dose at which a resist pattern can be formed with a size within a predetermined range of variation from a target size, when exposure is conducted by changing the exposure dose, i.e., the range of the exposure dose at which a resist pattern faithful to the mask pattern can be formed. The larger the exposure margin, the smaller the variation in the pattern size depending on the change in the exposure dose, thereby resulting in favorable improvement in the process margin.

Furthermore, the alkyl chain of the alkylene group or fluorinated alkyl group for $Y^1$ which may have a substituent exhibits an excellent decomposability, as compared to, for example, a perfluoroalkyl chain of 6 to 10 carbon atoms. Therefore, the effect of minimizing bioaccumulation to improve ease of handling can be achieved.

EXAMPLES

As follows is a description of examples of the present invention, although the scope of the present invention is by no way limited by these examples.

Example 1

(i) 192.1 g of methyl fluorosulfonyl(difluoro)acetate and 480 g of pure water were maintained at 10° C. or lower in an ice bath, and 440 g of a 30% by weight aqueous solution of sodium hydroxide was dropwise added thereto. Then, the resultant was refluxed at 100° C. for 3 hours, followed by cooling and neutralizing with 10% by weight hydrochloric acid. The resulting solution was dropwise added to 9,074 g of acetone, and the precipitate was collected by filtration and dried, thereby obtaining 257.6 g of a compound (1) in the form of a white solid (purity: 80.7%, yield: 94.5%).

[Chemical Formula 57.]

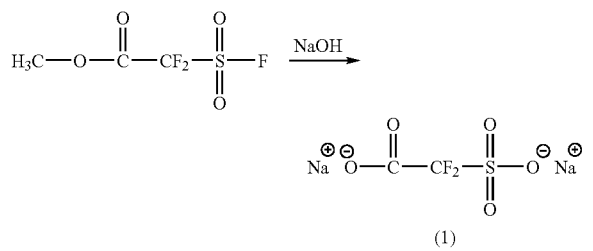

(ii) 56.2 g of the compound (1) and 562.2 g of acetonitrile were prepared, and 77.4 g of p-toluenesulfonic acid hydrate was added thereto. The resultant was refluxed at 110° C. for 3 hours. Then, the reaction liquid was filtered, and the filtrate was concentrated and dried to obtain a solid.

900 g of t-butyl methyl ether (TBME) was added to the obtained solid and stirred. Thereafter, the resultant was filtered, and the residue was dried, thereby obtaining 25.7 g of a compound (2) in the form of a white solid (purity: 91.0%, yield: 52.0%).

[Chemical Formula 58.]

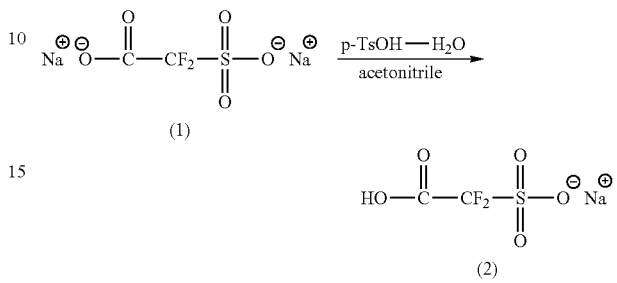

(iii) 5.00 g of the compound (2) (purity: 91.0%), 4.80 g of sultone—OH (3) and 25.0 g of toluene were prepared, and 0.935 g of p-toluenesulfonic acid hydrate was added thereto. The resultant was refluxed at 110° C. for 26 hours. Then, the reaction liquid was filtered, and 25.0 g of toluene was added and stirred at room temperature for 10 minutes. This filtration procedure was repeated twice, thereby obtaining a white powder.

The obtained white powder was dried under reduced pressure for one night. Then, on the following day, 5 g of acetone was added to the white powder and stirred at room temperature for 15 minutes, followed by filtration. The resulting filtrate was dropwise added slowly to 25.0 g of TBME and 25.0 g of methylene chloride. Thereafter, the precipitated solid was collected by filtration and dried, thereby obtaining 5.89 g of a compound (4) in the form of a white powder (purity: 98.4%, yield: 68.1%).

[Chemical Formula 59.]

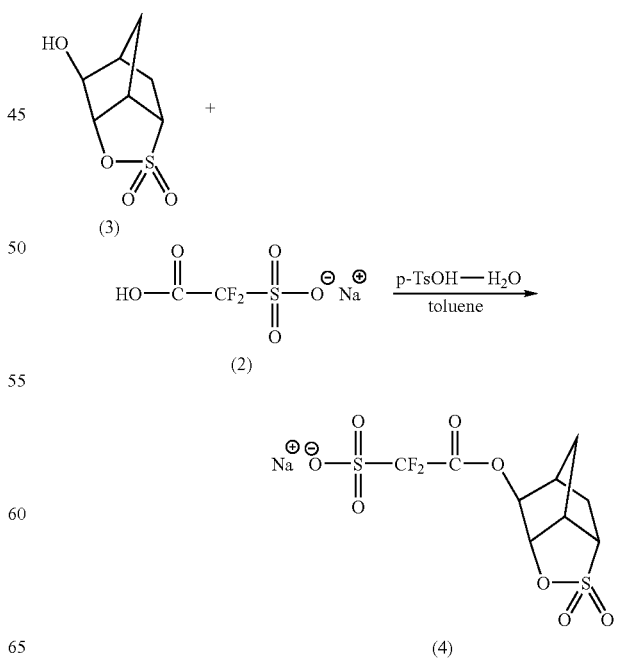

The obtained compound (4) was analyzed by $^1$H-NMR and $^{19}$F-NMR.

$^1$H-NMR(DMSO-d6, 400 MHz): δ(ppm)1.73-2.49(m,4H, Ha,Hb), 2.49(m,1H,Hc), 3.34(m,1H,Hd), 3.88(t,1H,He), 4.66(t,1H,Hf), 4.78(m,1H,Hg)

$^{19}$F-NMR(DMSO-d6, 400 MHz): δ(ppm)-107.7(m,2F,Fa) (the peak of hexafluorobenzene was regarded as −160 ppm)

From the results above, it was confirmed that the compound (4) had a structure shown below.

[Chemical Formula 60.]

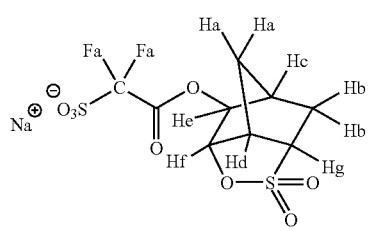

Compound (4)

Example 2

(iv) 3.21 g of the compound (4) was dissolved in 32.1 g of pure water, and 3.72 g of 4-methyltriphenylsulfonium bromide was added thereto. Then, 32.1 g of methylene chloride was added thereto, and stirred at room temperature for 1 hour. Thereafter, the resultant was subjected to liquid separation to take out the organic phase. The organic phase was washed three times with 1% by weight aqueous solution of HCl, and four times with pure water. The resulting organic phase was concentrated, thereby obtaining 4.94 g of a compound (5) in the form of a white solid (purity: 98.8%, yield: 86.8%).

[Chemical Formula 61.]

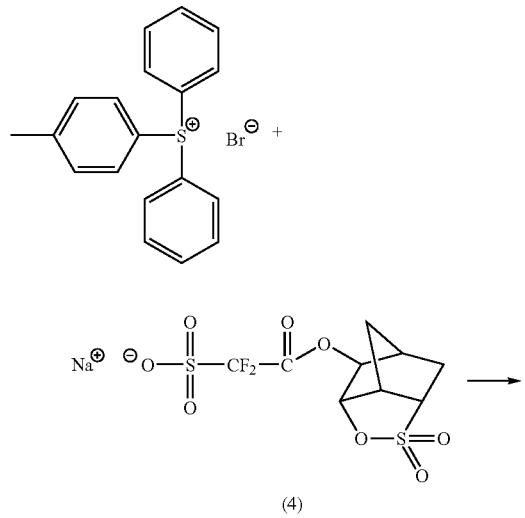

(4)

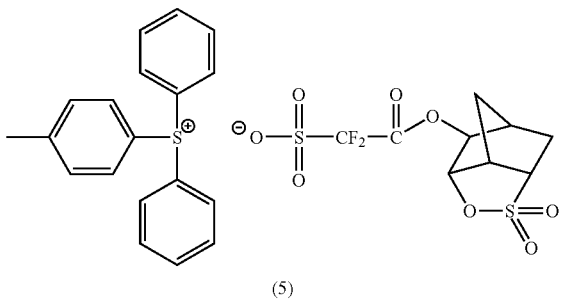

(5)

The obtained compound (5) was analyzed by $^1$H-NMR and $^{19}$F-NMR.

$^1$H-NMR(DMSO-d6, 400 MHz): δ(ppm)1.74-2.21(m,4H, Ha,Hb), 2.41(t,3H,Hh), 2.58(m,1H,Hc), 3.47(m,1H,Hd), 3.87(t,1h,He), 4.66(t,1H,Hf), 4.78(m,1H,Hg), 7.58(m,2H, Hi), 7.64-7.84(m,12H,Hj)

$^{19}$F-NMR(DMSO-d6, 400 MHz): δ(ppm) -107.6(m,2F, Fa), (the peak of hexafluorobenzene was regarded as −160 ppm).

From the results above, it was confirmed that the compound (5) had a structure shown below.

[Chemical Formula 62.]

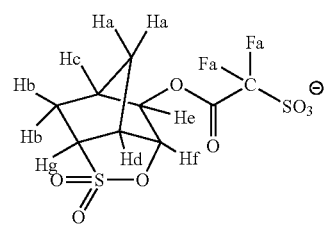

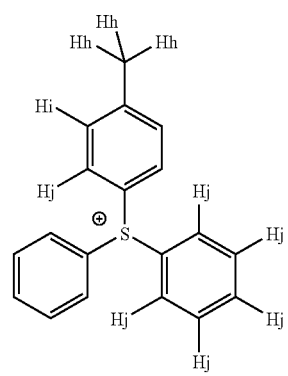

Example 3

The components shown in Table 1 were mixed together and dissolved to obtain a positive resist composition.

TABLE 1

|  | Component (A) | Component (B) | Component (D) | Component (E) | Component (S) | |
|---|---|---|---|---|---|---|
| Example 3 | (A)-1 [100] | (B)-1 [6.5] | (D)-1 [0.50] | (E)-1 [1.32] | (S)-1 [2000] | (S)-2 [10] |

In Table 1, the values in brackets [ ] indicate the amount (in terms of parts by weight) of the component added.
Further, the reference characters indicate the following.
(A)-1: a copolymer represented by chemical formula (A)-1 shown below (wherein l/m/n = 45/35/20 (molar ratio)) with Mw = 7,000 and Mw/Mn = 1.8
(B)-1: the aforementioned compound (5)
(D)-1: tri-n-pentylamine
(E)-1: salicylic acid
(S)-1: a mixed solvent of PGMEA/PGME = 6/4 (weight ratio)
(S)-2: γ-butyrolactone
[Chemical Formula 63.]
(A)-1

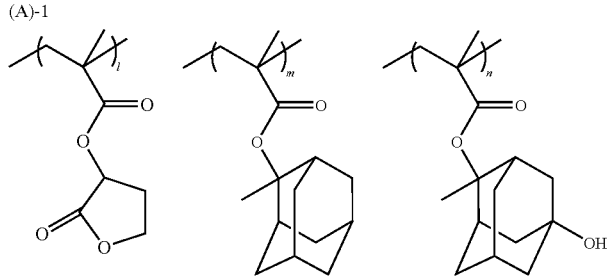

[Resolution•Sensitivity]

An organic anti-reflection film composition (product name: ARC29, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. Then, the positive resist composition obtained in Example 3 was applied onto the anti-reflection film using a spinner, and was then prebaked (PAB) on a hotplate at 100° C. for 60 seconds and dried, thereby forming a resist film having a film thickness of 120 nm.

Subsequently, the resist film was selectively irradiated with an ArF excimer laser (193 nm) through a mask pattern, using an ArF exposure apparatus NSR-S302 (manufactured by Nikon Corporation, NA (numerical aperture)=0.60, ⅔ annular illumination).

Thereafter, a post exposure bake (PEB) treatment was conducted at 100° C. for 60 seconds, followed by alkali development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, a line and space pattern with a line width of 130 nm and a pitch of 260 nm was formed on the resist film.

From the results above, it was confirmed that the resist composition of Example 3 exhibited excellent lithography properties.

Example 4, Comparative Example 1

The components shown in Table 2 were mixed together and dissolved to obtain positive resist compositions.

TABLE 2

|  | Component (A) | Component (B) | Component (D) | Component (E) | Component (S) | |
|---|---|---|---|---|---|---|
| Ex. 4 | (A)-1 [100] | (B)-1 [8.67] | (D)-1 [1.20] | (E)-1 [1.32] | (S)-1 [2120] | (S)-2 [10] |
| Comp. Ex. 1 | (A)-1 [100] | (B)-2 [8.00] | (D)-1 [1.20] | (E)-1 [1.32] | (S)-1 [2120] | (S)-2 [10] |

In Table 2, the values in brackets [ ] indicate the amount (in terms of parts by weight) of the component added. Further, the reference characters indicate the following.
(A)-1: a copolymer represented by chemical formula (A)-1 above (wherein l/m/n = 45/35/20 (molar ratio)) with Mw = 7,000 and Mw/Mn = 1.8
(B)-1: the aforementioned compound (5)
(B)-2: a compound represented by chemical formula (B)-2 shown below
(D)-1: tri-n-pentylamine TABLE 2-continued

| Component (A) | Component (B) | Component (D) | Component (E) | Component (S) |
| --- | --- | --- | --- | --- |

(E)-1: salicylic acid
(S)-1: a mixed solvent of PGMEA/PGME = 6/4 (weight ratio)
(S)-2: γ-butyrolactone
[Chemical Formula 64.]
(B)-2

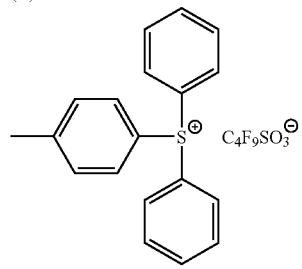

[Resolution•sensitivity]

An organic anti-reflection film composition (product name: ARC29, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. Then, each of the positive resist compositions obtained in Example 4 and Comparative Example 1 was applied onto the anti-reflection film using a spinner, and was then prebaked (PAB) on a hotplate at 110° C. for 60 seconds and dried, thereby forming a resist film having a film thickness of 150 nm.

Subsequently, the resist film was selectively irradiated with an ArF excimer laser (193 nm) through a mask pattern, using an ArF exposure apparatus NSR-S302 (manufactured by Nikon Corporation, NA (numerical aperture)=0.60, ⅔ annular illumination).

Thereafter, a post exposure bake (PEB) treatment was conducted at 110° C. for 60 seconds, followed by alkali development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a line and space pattern (L/S pattern) with a line width of 120 nm and a pitch of 260 nm was formed on the resist film. The optimum exposure dose Eop (mJ/cm$^2$) with which the pattern was formed, i.e., sensitivity was determined. The results are shown in Table 3.

Further, the lithography properties (LWR, pattern shape, MEF, EL margin) of the obtained L/S patterns were evaluated. The results are shown in Table 3.

[Line Width Roughness]

With respect to each of the L/S patterns obtained above, the line width at 5 points in the lengthwise direction of the line were measured using a measuring SEM (product name: S-9220, manufactured by Hitachi, Ltd.), and from the results, the value of 3 times the standard deviation s (i.e., 3s) was calculated as a yardstick of LWR.

The smaller this 3s value is, the lower the level of roughness of the line width, indicating that a resist pattern with a uniform width was obtained.

[Evaluation of Pattern Shape]

The cross-sectional shape of the obtained L/S patterns was observed using a measuring SEM (product name: S-9220, manufactured by Hitachi, Ltd.), and the shape of the L/S patterns was evaluated with the following criteria.

A: Footing of the pattern was small, and the rectangularity of the pattern was high
B: Footing of the pattern was large

[Evaluation of Mask Error Factor (MEF)]

With the above-mentioned Eop, L/S patterns were formed using a mask pattern targeting a L/S pattern having a line width of 130 nm and a pitch of 260 nm and a mask pattern targeting a L/S pattern having a line width of 120 nm and a pitch of 260 nm. With respect to the formed L/S patterns, the MEF was determined by the following formula.

$$MEF = |CD_{130} - CD_{120}| / |MD_{130} - MD_{120}|$$

In this formula, $CD_{130}$ and $CD_{120}$ represent the respective line widths (nm) of the actual L/S patterns respectively formed using the mask pattern targeting a line width of 130 nm and the mask pattern targeting a line width of 120 nm, and $MD_{130}$ and $MD_{120}$ represent the respective target line widths (nm), meaning $MD_{130}$=130 and $MD_{120}$=120. The closer the MEF value is to 1, the better the mask reproducibility of the resist pattern formed.

[Evaluation of EL Margin]

The exposure dose with which a L/S pattern having a dimension of the target dimension (line width: 120 nm)±5% (i.e., 114 nm to 126 nm) was determined, and the EL margin (unit: %) was determined by the following formula.

$$EL\ margin\ (\%) = (|E1 - E2|/Eop) \times 100$$

wherein E1 represents the exposure dose (mJ/cm$^2$) for forming a L/S pattern having a line width of 114 nm, and E2 represents the exposure dose (mJ/cm$^2$) for forming a L/S pattern having a line width of 126 nm.

The larger the exposure margin, the smaller the variation in the pattern size depending on the change in the exposure dose, thereby resulting in favorable improvement in the process margin.

TABLE 3

| | Eop (mJ/cm$^2$) | LWR (nm) | Shape | MEF | EL (%) |
| --- | --- | --- | --- | --- | --- |
| Ex. 4 | 46.5 | 10.4 | A | 1.68 | 8.49 |
| Comp. Ex. 1 | 31.5 | 10.4 | B | 2.03 | 5.70 |

As seen from Table 3, the resist composition of Example 4 exhibited excellent pattern shape, MEF and EL margin as compared to the resist composition of Comparative Example 1. Further, the resist composition of Example 4 exhibited the same or higher level of LWR as that of the resist composition of Comparative Example 1.

Examples 5 and 6

The components shown in Table 4 were mixed together and dissolved to obtain positive resist compositions.

TABLE 4

| | Component (A) | Component (B) | Component (D) | Component (S) |
|---|---|---|---|---|
| Ex. 5 | (A)-2 [100] | (B)-1 [5.0] | — | (S)-1 [2400] |
| Ex. 6 | (A)-2 [100] | (B)-1 [5.0] | (D)-4 [0.30] | (S)-1 [2400] |

In Table 4, the values in brackets [ ] indicate the amount (in terms of parts by weight) of the component added. Further, the reference characters indicate the following.
(A)-2: Polymeric compound (A)-2 (synthesized in Reference Example 3 below)
(B)-1: the aforementioned compound (5)
(D)-4: stearyldiethanolamine
(S)-1: a mixed solvent of PGMEA/PGME = 6/4 (weight ratio)

[Synthesis Example of Polymeric Compound (A)-2]

Reference Example 1

4.8 g of sodium hydride (NaH) was charged into a 1L three-necked flask. While maintaining the temperature of the three-necked flask at 0° C. in an ice bath, 300 g of tetrahydrofuran (THF) was added, 124 g of a compound (1') was further added while stirring, and stirring was continued for 10 minutes. Then, 30 g of a compound (2') was added while stirring, and a reaction was effected for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography (SiO$_2$, heptane:ethyl acetate=8:2). The obtained fraction was concentrated and dried under reduced pressure, thereby obtaining 12 g of a compound (3').

[Chemical Formula 65.]

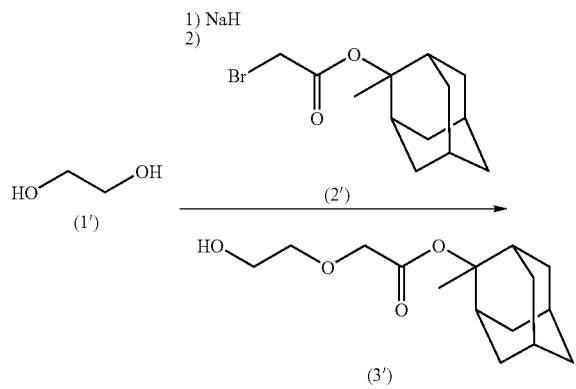

The obtained compound (3') was analyzed by $^1$H-NMR. The results are shown below.

$^1$H-NMR (solvent: CDCl$_3$, 400 MHz): δ(ppm)=4.09(s,2H (H$^a$)), 3.75(t,2H(H$^b$), 3.68(t,2H(H$^c$), 3.03(brs,2H(H$^d$)), 1.51-2.35(m,17H(H$^e$).

From the results shown above, it was confirmed that the compound (3') had a structure shown below.

[Chemical Formula 66.]

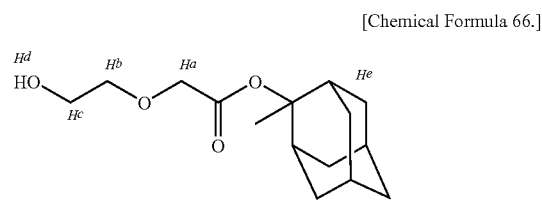

Reference Example 2

5 g of the compound (3'), 3.04 g of triethylamine (Et$_3$N) and 10 g of THF were charged into a 300 mL three-necked flask, and stirred for 10 minutes. Then, 2.09 g of a compound (4') and 10 g of THF were added to the three-necked flask, and a reaction was effected at room temperature for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography (SiO$_2$, heptane:ethyl acetate=8:2). The obtained fraction was concentrated and dried under reduced pressure, thereby obtaining 4.9 g of a compound (5').

[Chemical Formula 67.]

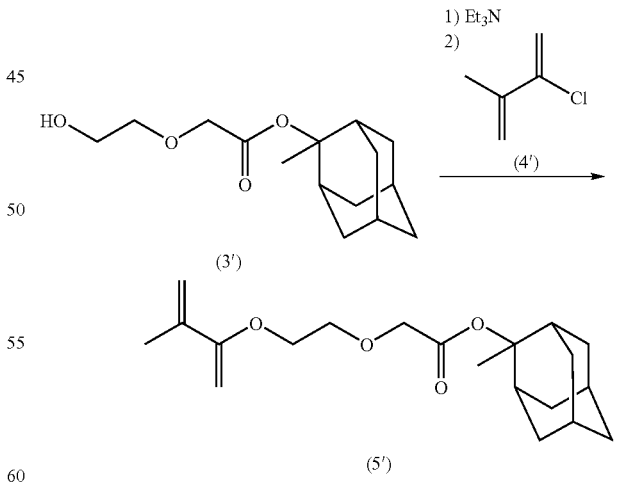

The obtained compound (5') was analyzed by $^1$H-NMR. The results are shown below.

$^1$H-NMR (solvent: CDCl$_3$, 400 MHz): δ(ppm)=6.15(s,1H (H$^a$)), 5.58(s,1H(H$^b$)), 4.35(t,2H(H$^e$)), 4.08(s,2H(H$^d$)), 3.80 (t,2H(H$^e$)), 1.51-2.35(m,20H(H$^f$)).

From the results shown above, it was confirmed that the compound (5') had a structure shown below.

[Chemical Formula 68.]

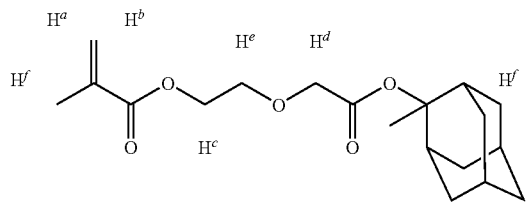

Reference Example 3

Synthesis of Polymeric Compound (A)-2

6.19 g (29.76 mmol) of a compound (6) shown below, 10.00 g (29.76 mmol) of the compound (5') and 3.51 g (14.88 mmol) of a compound (7) shown below were dissolved in 78.80 g of methyl ethyl ketone to obtain a solution. Then, 13.39 mmol of a polymerization initiator (product name: V-601, manufactured by Wako Pure Chemical Industries, Ltd.) was added and dissolved in the obtained solution. The resultant was dropwise added to 32.83 g of methyl ethyl ketone heated to 75° C. in a nitrogen atmosphere over 6 hours. The resulting reaction liquid was heated while stirring for 1 hour, and then cooled to room temperature.

Subsequently, the resulting polymerization liquid was concentrated to a solid content of 30% by weight, and dropwise added to 370 ml of n-heptane at room temperature to deposit a copolymer. Then, 66 g of a THF solution of the obtained copolymer was prepared, and the THF solution was dropwise added to 370 ml of n-heptane to deposit a copolymer.

The obtained copolymer was dispersed in a methanol/water=60/40 (weight ratio) mixed solution to wash the copolymer, and then the copolymer was dispersed in a methanol/water=70/30 (weight ratio) mixed solution to wash the copolymer, followed by filtration to collect the copolymer.

The thus obtained copolymer was dried at 40° C. for 3 days, thereby obtaining 14.9 g of a white powder (yield: 76%).

The obtained copolymer was designated as "polymeric compound (A)-2". The structure of the polymeric compound (A)-2 is shown below.

The polymeric compound (A)-2 was analyzed by $^{13}$C-NMR (600 MHz,). As a result, it was found that the composition of the polymer (ratio (molar ratio) of the respective structural units within the structural formula) was 1/m/n=42.4/37.2/19.9. Further, with respect to the polymeric compound (A)-2, the weight average molecular weight and the dispersity were determined by the polystyrene equivalent value as measured by gel permeation chromatography (GPC). As a result, it was found that the weight average molecular weight was 6,400, and the dispersity was 1.80. From the results above, it was found that the polymeric compound (A)-2 was a copolymer of the compound (6), the compound (5') and the compound (7).

[Chemical Formula 69.]

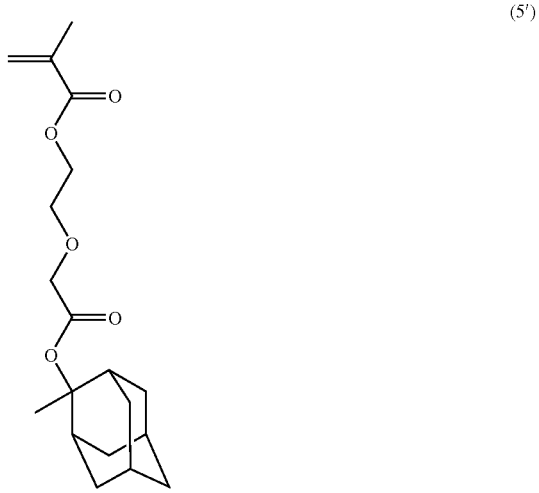

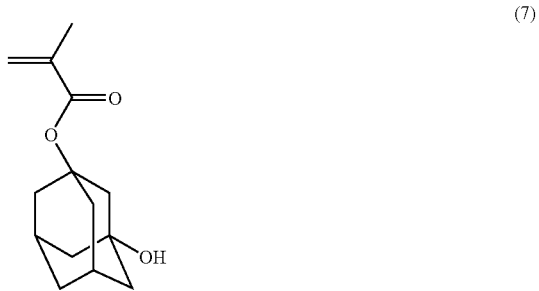

[Chemical Formula 70.]

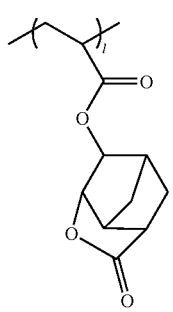

-continued

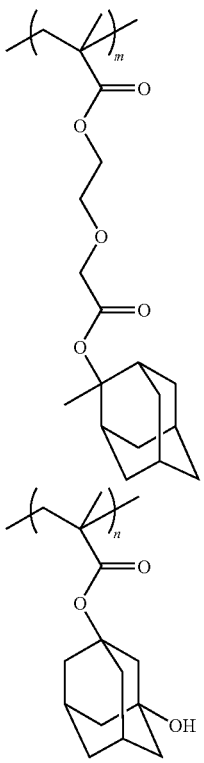

[Resolution·Sensitivity]

An organic anti-reflection film composition (product name: ARC29, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. Then, each of the positive resist compositions obtained in Examples 5 and 6 was applied onto the anti-reflection film using a spinner, and was then prebaked (PAB) on a hotplate at 90° C. for 60 seconds and dried, thereby forming a resist film having a film thickness of 120 nm.

Subsequently, the resist film was selectively irradiated with an ArF excimer laser (193 nm) through a mask pattern, using an ArF exposure apparatus NSR-S302 (manufactured by Nikon Corporation, NA (numerical aperture)=0.60, ⅔ annular illumination).

Thereafter, a post exposure bake (PEB) treatment was conducted at 90° C. for 60 seconds, followed by alkali development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a dense contact hole pattern (C/H pattern) in which holes having a hole diameter of 140 nm were equally spaced (pitch: 280 nm) was formed on the resist film. The optimum exposure dose Eop (mJ/cm$^2$) with which the pattern was formed, i.e., sensitivity was determined. The results are shown in Table 5.

Further, the lithography properties (circularity, EL margin) of the obtained C/H patterns were evaluated. The results are shown in Table 5.

[Evaluation of Circularity]

The shape of the holes of the dense C/H patterns was observed from the upper side thereof using a measuring SEM (product name: S-9220, manufactured by Hitachi, Ltd.). As a result, it was found that in each of the C/H patterns, no unevenness was observed at the circumferential portions of the holes of the hole pattern, and hence, the dense C/H patterns had excellent shape and high circularity.

[Evaluation of EL Margin]

The exposure dose with which a dense C/H pattern having a dimension of the target dimension (hole diameter: 140 nm)±5% (i.e., 133 nm to 147 nm) was determined, and the EL margin (unit: %) was determined by the following formula. The results are shown in Table 5.

$$EL\ margin\ (\%)=(|E1-E2/Eop)\times100$$

wherein E1 represents the exposure dose (mJ/cm$^2$) for forming a C/H pattern having a hole diameter of 133 nm, and E2 represents the exposure dose (mJ/cm$^2$) for forming a C/H pattern having a line width of 147 nm.

TABLE 5

|  | Eop (mJ/cm$^2$) | Circularity | EL (%) |
|---|---|---|---|
| Ex. 5 | 11.77 | Extremely high | 3.96 |
| Ex. 6 | 27.11 | Extremely high | 3.06 |

As seen from Table 5, the resist compositions of Examples 5 and 6 exhibited excellent properties with respect to both of circularity and EL margin.

Example 7

5.00 g of the compound (4) was dissolved in 50.0 g of pure water, and 6.19 g of a compound (e) was added thereto. Then, 50.0 g of methylene chloride was added thereto, and stirred at room temperature for 10 hours. Thereafter, the resultant was subjected to liquid separation to take out the organic phase. The organic phase was washed three times with a 1% aqueous solution of HCl, once with a 1% aqueous solution of ammonia, and four times with pure water. The resulting organic phase was concentrated, thereby obtaining 8.58 g of a compound (e') in the form of a white solid (yield: 90.4%).

The obtained compound (e') was analyzed by $^1$H-NMR and $^{19}$F-NMR.

$^1$H-NMR(DMSO-d6, 400 MHz): δ (ppm)=1.47-1.95(m, 15H, Ad, 3H, ST), 2.13-2.16(m, 2H, Ad, 1H, ST), 2.30(s, 6H, PhCH$_3$), 2.49(m, 1H, ST), 3.48(m,1H,ST), 3.88(t,1H,ST), 4.58(s,2H,CH$_2$), 4.66(t,1H,ST), 4.78(m,1H,ST), 7.57(m,2H, Ph), 7.72-7.84(m, 10H, Ph).

$^{19}$F-NMR(DMSO-d6, 400 MHz): δ(ppm) -107.8(m, 2F, CF$_2$), (the peak of hexafluorobenzene was regarded as -160 ppm).

Here, "ST" refers to a peak ascribed to the sultone ring within the anion moiety, and the same applies for the NMR data shown below.

From the results above, it was confirmed that the compound (e') had a structure shown below.

[Chemical Formula 71.]

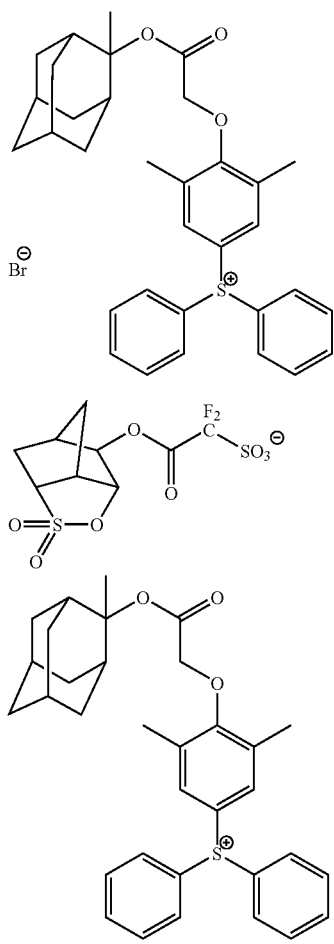

(e)

(e')

Example 8

5.00 g of the compound (4) was dissolved in 50.0 g of pure water, and 5.31 g of a compound (f) was added thereto. Then, 50.0 g of methylene chloride was added thereto, and stirred at room temperature for 10 hours. Thereafter, the resultant was subjected to liquid separation to take out the organic phase. The organic phase was washed three times with a 1% aqueous solution of HCl, and four times with pure water. The resulting organic phase was concentrated, thereby obtaining 7.43 g of a compound (f') in the form of a white solid (yield: 91.2%).

The obtained compound (f') was analyzed by $^1$H-NMR and $^{19}$F-NMR.

$^1$H-NMR(DMSO-d6, 400 MHz): δ(ppm)=0.86(t, 3H,CH3), 1.28-1.30(m, 4H, CH$_3$CH$_2$CH$_2$), 1.45(m, 2H, CH$_3$CH$_2$CH$_2$CH$_2$), 1.74-1.96(m, 2H, OCH$_2$CH$_2$,3H, ST), 2.13-2.34(m, 6H, PhCH$_3$, 1H, ST), 2.49(m, 1H, ST), 3.49(m, 1H,ST), 3.85-3.88(m,2H, OCH$_2$, 1H, ST), 4.66(t,1H,ST), 4.78(m,1H,ST), 7.55(m,2H, Ph), 7.75-7.85(m, 10H, Ph).

$^{19}$F-NMR(DMSO-d6, 400 MHz): δ (ppm)−107.8(m, 2F, CF$_2$), (the peak of hexafluorobenzene was regarded as −160 ppm).

From the results above, it was confirmed that the compound (f') had a structure shown below.

[Chemical Formula 72.]

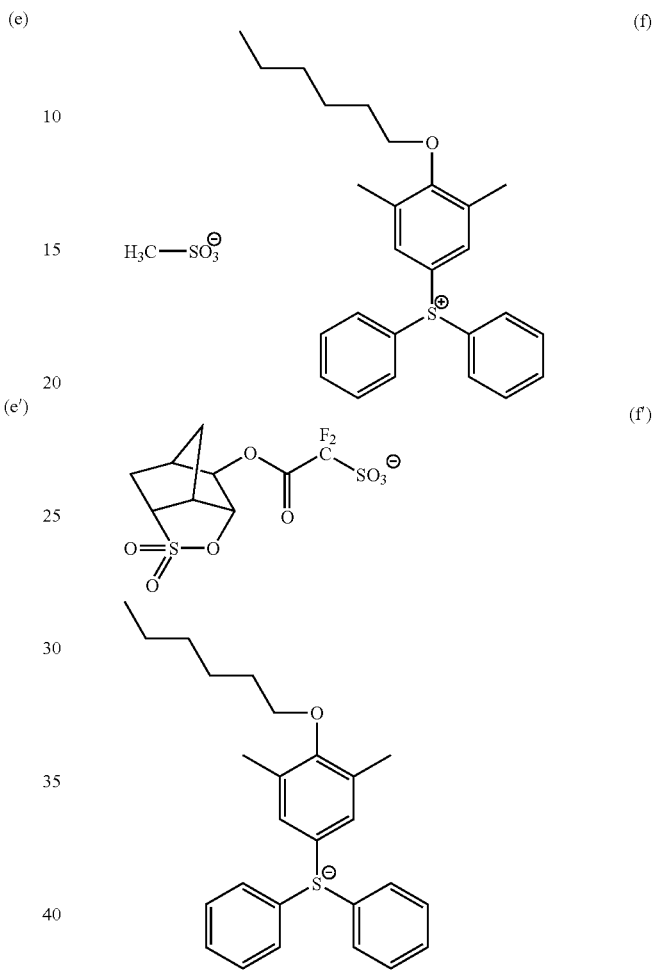

(f)

(f')

Example 9

5.00 g of the compound (4) was dissolved in 50.0 g of pure water, and 6.16 g of a compound (g) was added thereto. Then, 50.0 g of methylene chloride was added thereto, and stirred at room temperature for 10 hours. Thereafter, the resultant was subjected to liquid separation to take out the organic phase. The organic phase was washed three times with a 1% aqueous solution of HCl, and four times with pure water. The resulting organic phase was concentrated, thereby obtaining 8.13 g of a compound (g') in the form of a white solid (yield: 90.5%).

The obtained compound (g') was analyzed by $^1$H-NMR and $^{19}$F-NMR.

$^1$H-NMR(DMSO-d6, 400 MHz):δ(ppm)=1.66-2.03 (m, 15H, Ad, 3H, ST), 2.12-2.36(m, 6H, PhCH$_3$, 1H,ST), 2.49(m, 1H, ST), 3.59(m,1H,ST), 3.87(m, 1H, ST), 4.65(t,1H,ST), 4.78(m,1H,ST), 7.69(s, 2H, Ph), 7.75-7.87(m, 10H, Ph).

$^{19}$F-NMR(DMSO-d6, 400 MHz):δ(ppm)−107.7(m,2F, CF$_2$), (the peak of hexafluorobenzene was regarded as −160 ppm).

From the results above, it was confirmed that the compound (g') had a structure shown below.

[Chemical Formula 73.]

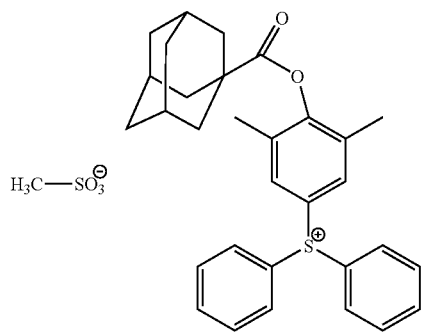

(g)

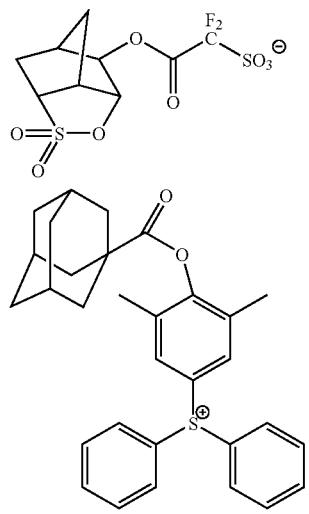

(g')

From the results above, it was confirmed that the compound (h') had a structure shown below.

[Chemical Formula 74.]

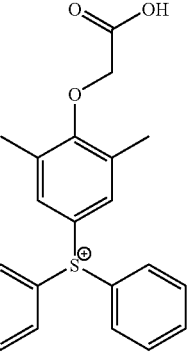

(h)

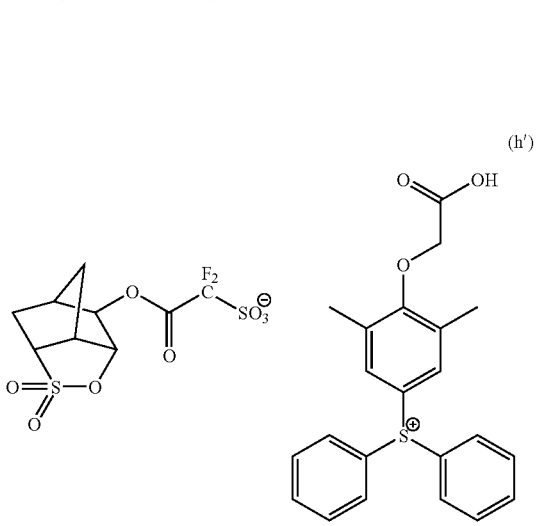

(h')

Example 10

5.00 g of the compound (4) was dissolved in 50.0 g of pure water, and 4.86 g of a compound (h) was added thereto. Then, 50.0 g of methylene chloride was added thereto, and stirred at room temperature for 10 hours. Thereafter, the resultant was subjected to liquid separation to take out the organic phase. The organic phase was washed three times with a 1% aqueous solution of HCl, and four times with pure water. The resulting organic phase was concentrated, thereby obtaining 6.84 g of a compound (h') in the form of a white solid (yield: 86.4%).

The obtained compound (h') was analyzed by $^1$H-NMR and $^{19}$F-NMR.

$^1$H-NMR(DMSO-d6, 400 MHz): δ(ppm)=1.73-1.97(m, 3H, ST), 2.17-2.30(m, 6H, PhCH$_3$, 1H, ST), 2.50(m, 1H, ST), 3.59(m, 1H, ST), 3.88(t, 1H, ST), 4.39(s, 2H, CH$_2$), 4.66(t, 1H, ST), 4.78(m, 1H, ST), 7.32(s, 2H, Ph), 7.70-7.87(m, 10H, Ph).

$^{19}$F-NMR(DMSO-d6, 400 MHz): δ(ppm)−107.5(m, 2F, CF$_2$), (the peak of hexafluorobenzene was regarded as −160 ppm).

Example 11

5.00 g of the compound (4) was dissolved in 50.0 g of pure water, and 4.98 g of a compound (i) was added thereto. Then, 50.0 g of methylene chloride was added thereto, and stirred at room temperature for 2 hours. Thereafter, the resultant was subjected to liquid separation to take out the organic phase. The organic phase was washed three times with a 1% aqueous solution of HCl, and four times with pure water. The resulting organic phase was concentrated, thereby obtaining 6.02 g of a compound (i') in the form of a white solid (yield: 87.6%).

The obtained compound (i') was analyzed by $^1$H-NMR and $^{19}$F-NMR.

$^1$H-NMR(DMSO-d6, 400 MHz):δ(ppm) 1.73-1.96(m, 3H, ST), 2.17-2.21(m, 6H, PhCH$_3$, 1H, ST), 2.48(m, 1H, ST), 3.60(m, 1H, ST), 3.88(t, 1H, ST), 4.64(t, 1H, ST), 4.77(m, 1H, ST), 7.51(m, 2H, Ph), 7.72-7.83(m, 10H, Ph), 9.99(s, 1H, OH).

$^{19}$F-NMR(DMSO-d6, 400 MHz):δ(ppm)−107.6(m, 2F, CF$_2$), (the peak of hexafluorobenzene was regarded as −160 ppm).

From the results above, it was confirmed that the compound (i') had a structure shown below.

[Chemical Formula 75.]

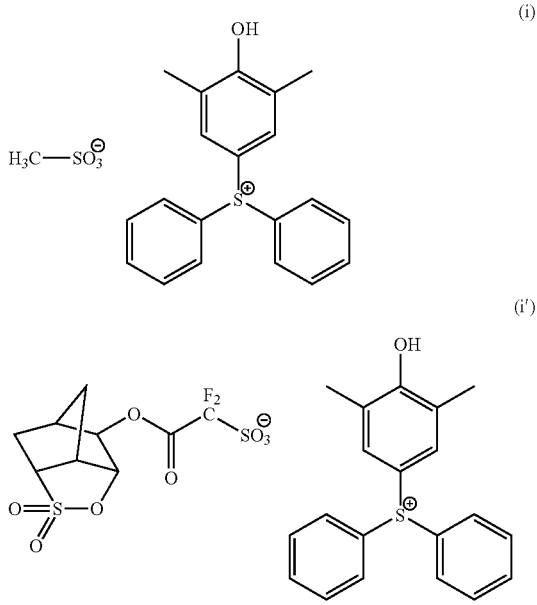

Example 12

5.00 g of the compound (4) was dissolved in 50.0 g of pure water, and 3.13 g of a compound (j) was added thereto. Then, 50.0 g of methylene chloride was added thereto, and stirred at room temperature for 10 hours. Thereafter, the resultant was subjected to liquid separation to take out the organic phase. The organic phase was washed twice with a 1% aqueous solution of HCl, and four times with pure water. The resulting organic phase was concentrated, thereby obtaining 4.24 g of a compound (j') in the form of a white solid (yield: 72.4%).

The obtained compound (j') was analyzed by $^1$H-NMR and $^{19}$F-NMR.

$^1$H-NMR(DMSO-d6, 400 MHz):δ(ppm) 1.74-1.96(m, 3H, ST), 2.14-2.25(m, 4H, SCH$_2$CH$_2$, 1H, ST), 2.47(m, 1H, ST), 3.47-3.59(m, 4H, SCH$_2$CH$_2$, 1H, ST), 3.88(t, 1H), ST), 4.66 (t, 1H, ST), 4.77(m, 1H, ST), 5.29(s, 2H, CH$_2$), 7.56(m, 2H, Ph), 7.71(m, 1H, Ph), 7.98(s, 2H, Ph).

$^{19}$F-NMR(DMSO-d6, 400 MHz):δ(ppm)–107.6(m, 2F, CF$_2$), (the peak of hexafluorobenzene was regarded as –160 ppm).

From the results above, it was confirmed that the compound (j') had a structure shown below.

[Chemical Formula 76.]

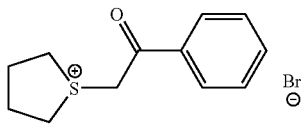

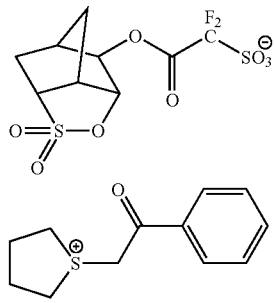

Example 13

5.00 g of the compound (4) was dissolved in 50.0 g of pure water, and 3.67 g of a compound (k) was added thereto. Then, 50.0 g of methylene chloride was added thereto, and stirred at room temperature for 10 hours. Thereafter, the resultant was subjected to liquid separation to take out the organic phase. The organic phase was washed twice with a 1% aqueous solution of HCl, and four times with pure water. The resulting organic phase was concentrated, thereby obtaining 3.98 g of a compound (k') in the form of a white solid (yield: 68.1%).

The obtained compound (k') was analyzed by $^1$H-NMR and $^{19}$F-NMR.

$^1$H-NMR(DMSO-d6, 400 MHz):δ(ppm) 1.74-2.01(m, 4H, SCH$_2$CH$_2$, 3H, ST), 2.14-2.30(m, 2H, SCH$_2$CH$_2$CH$_2$, 1H, ST), 2.47(m, 1H, ST), 3.60(m, 1H, ST), 3.70-4.01(m, 4H, SCH$_2$, 1H, ST), 4.66(t, 1H, ST), 4.77(m, 1H, ST), 7.28-7.73 (m, 3H, Ph), 8.05(m, 2H, Ph).

$^{19}$F-NMR(DMSO-d6, 400 MHz):δ(ppm)–107.7(m, 2F, CF$_2$), (the peak of hexafluorobenzene was regarded as –160 ppm).

From the results above, it was confirmed that the compound (k') had a structure shown below.

[Chemical Formula 77.]

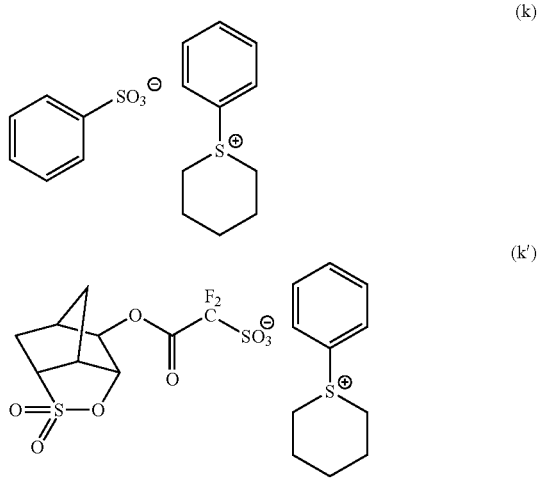

Example 14

5.00 g of the compound (4) was dissolved in 50.0 g of pure water, and 7.23 g of a compound (l) was added thereto. Then, 50.0 g of methylene chloride was added thereto, and stirred at room temperature for 2 hours. Thereafter, the resultant was subjected to liquid separation to take out the organic phase. The organic phase was washed three times with a 1% aqueous solution of HCl, and four times with pure water. The resulting organic phase was concentrated, thereby obtaining 8.66 g of a compound (1') in the form of a white solid (yield: 85.9%).

The obtained compound (1') was analyzed by $^1$H-NMR and $^{19}$F-NMR.

$^1$H-NMR(DMSO-d6, 400 MHz):δ(ppm) 1.74-1.96(m, 3H, ST), 2.14-2.40(m, 4H, CF$_2$CH$_2$CH$_2$, 6H, PhCH$_3$, 1H, ST), 2.47(m, 1H, ST), 3.60(m, 1H, ST), 3.90(t,1H, ST), 4.64(t, 1H, ST), 4.75-4.78(m, 2H, OCH$_2$,1H, ST), 7.42(m, 2H, Ph), 7.63-7.80(m, 10H, Ph).

$^{19}$F-NMR(DMSO-d6, 400 MHz):δ(ppm)−81.0(t, 3F, CF$_3$), −107.5(m, 2F, SO3CF$_2$), −114.1(m, 2F, CF$_3$CF$_2$), −124.3(m, 2F, CF$_3$CF$_2$CF$_2$), −126.0(m, 2F, CH$_2$CH$_2$), (the peak of hexafluorobenzene was regarded as −160 ppm).

From the results above, it was confirmed that the compound (1') had a structure shown below.

The organic phase was washed three times with a 1% aqueous solution of HCl, and four times with pure water. The resulting organic phase was concentrated, thereby obtaining 7.23 g of a compound (m') in the form of a white solid (yield: 89.5%).

The obtained compound (m') was analyzed by $^1$H-NMR and $^{19}$F-NMR.

$^1$H-NMR(DMSO-d6, 400 MHz):δ(ppm) 0.82(t, 3H, CH$_3$), 1.24-1.26(m, 4H, CH$_3$CH$_2$CH$_2$), 1.37(m, 2H, CH$_3$CH$_2$CH$_2$CH$_2$), 1.69-1.97(m, 2H, OCH$_2$CH$_2$, 6H, PhCH$_3$, 3H, ST), 2.16(m, 1H, ST), 2.46(m, 1H, ST), 3.63(m, 1H, ST), 3.88(t, 1H, ST), 4.05(t, 2H, OCH$_2$), 4.66(t, 1H, ST), 4.77(m, 1H, ST), 6.38(s, 1H, Ph), 7.20(s, 1H, Ph), 7.74(t, 3H, Ph), 7.95(t, 3H, Ph), 8.27(d, 2H, Ph), 8.53(d, 2H, Ph).

$^{19}$F-NMR(DMSO-d6, 400 MHz):δ(ppm)−107.4(m, 2F, CF$_2$), (the peak of hexafluorobenzene was regarded as −160 ppm).

From the results above, it was confirmed that the compound (m') had a structure shown below.

[Chemical Formula 78.]

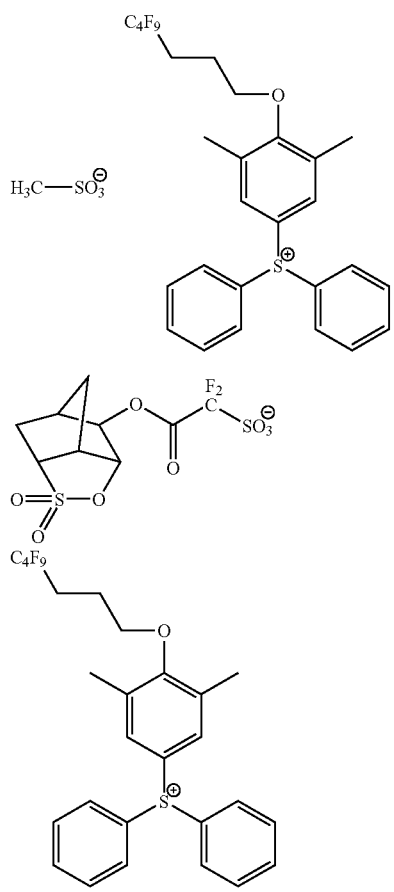

Example 15

[Chemical Formula 79.]

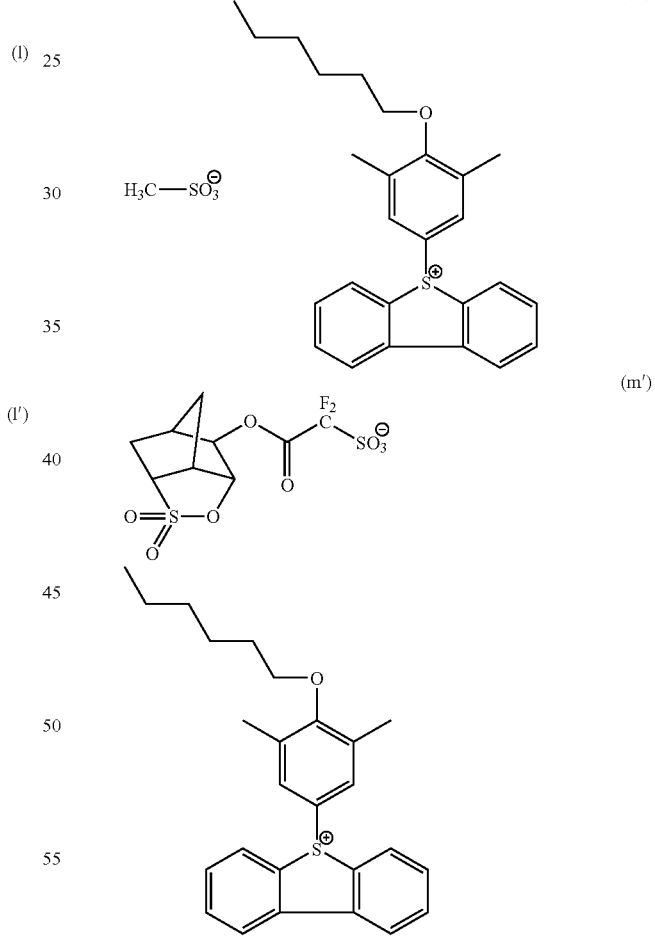

Example 16

5.00 g of the compound (4) was dissolved in 50.0 g of pure water, and 5.28 g of a compound (m) was added thereto. Then, 50.0 g of methylene chloride was added thereto, and stirred at room temperature for 2 hours. Thereafter, the resultant was subjected to liquid separation to take out the organic phase.

5.00 g of the compound (4) was dissolved in 50.0 g of pure water, and 5.17 g of a compound (n) was added thereto. Then, 50.0 g of methylene chloride was added thereto, and stirred at room temperature for 10 hours. Thereafter, the resultant was subjected to liquid separation to take out the organic phase.

The organic phase was washed three times with a 1% aqueous solution of HCl, and four times with pure water. The resulting organic phase was concentrated, thereby obtaining 6.78 g of a compound (n') in the form of a white solid (yield: 84.6%).

The obtained compound (n') was analyzed by $^{1}$H-NMR and $^{19}$F-NMR.

$^{1}$H-NMR(DMSO-d6, 400 MHz):δ(ppm) 1.74-1.96(m, 3H, ST), 2.14-2.29(m, 6H, PhCH$_{3}$, 1H, ST), 2.47(m, 1H, ST), 3.55(m, 1H, ST), 3.70(s, 3H, OCH$_{3}$), 3.88(t, 1H, ST), 4.64-4.66(s, 2H, OCH$_{2}$, t, 1H, ST), 4.77(m, 1H, ST), 7.59(m, 2H, Ph), 7.72-7.84(m, 10H, Ph).

$^{19}$F-NMR(DMSO-d6, 400 MHz):δ(ppm)–107.7(m, 2F, CF$_{2}$), (the peak of hexafluorobenzene was regarded as –160 ppm).

From the results above, it was confirmed that the compound (n') had a structure shown below.

[Chemical Formula 80.]

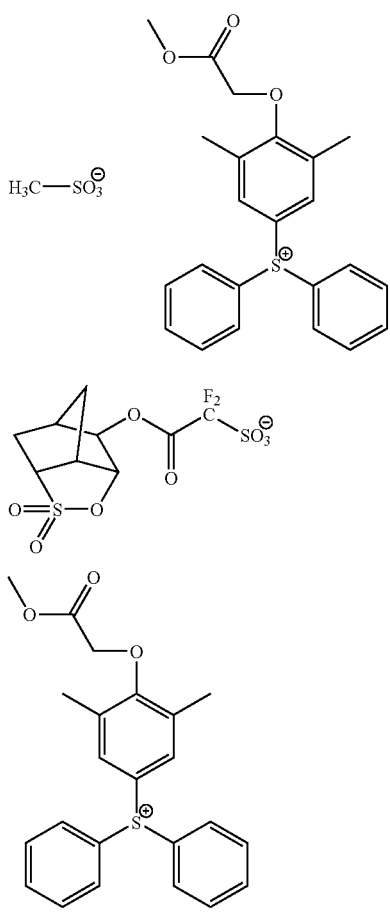

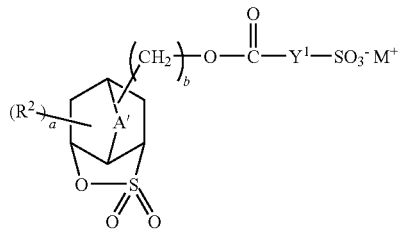

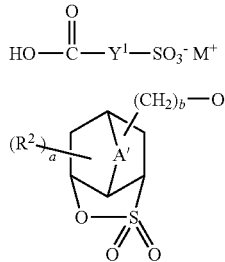

wherein A' represents an alkylene group of 1 to 5 carbon atoms, —O—, —S—, —O—R$^{3}$— or —S—R$^{4}$—, wherein each of R$^{3}$ and R$^{4}$ independently represents an alkylene group of 1 to 5 carbon atoms; R$^{2}$ represents an alkyl group of 1 to 6 carbon atoms, an alkoxy group of 1 to 6 carbon atoms, a halogenated alkyl group of 1 to 6 carbon atoms, a halogen atom, a hydroxyl group, —COOR", —OC(=O)R", a hydroxyalkyl group or a cyano group; a represents an integer of 0 to 2; b represents an integer of 0 to 5; Y$^{1}$ represents an alkylene group which may have a substituent or a fluorinated alkylene group which may have a substituent; and M$^{+}$ represents an alkali metal ion.

2. The method according to claim 1, wherein the acidic catalyst is at least one member selected from the group consisting of p-toluenesulfonic acid, sulfuric acid and hydrochloric acid.

3. The method according to claim 1, wherein the amount of the acidic catalyst is in the range of 0.001 to 5 moles, per 1 mole of the compound (I-4).

4. The method according to claim 1, wherein the dehydration/condensation is performed in an aprotic organic solvent.

5. The method according to claim 4, wherein the aprotic organic solvent is selected from the group consisting of dichloroethane, benzene, toluene, ethylbenzene, chlorobenzene, acetonitrile, xylene and N,N-dimethylformamide.

6. The method according to claim 1, wherein the dehydration/condensation is performed at a temperature of 20° C. to 200° C.

7. The method according to claim 1, wherein the dehydration/condensation is performed for 1 to 30 hours.

8. The method according to claim 1, wherein the amount of the compound (I-3) is in the range of 0.2 to 3 moles, per 1 mole of the compound (I-4).

9. The method according to claim 1, wherein the dehydration/condensation is performed while removing water by using a Dean-Stark apparatus.

10. The method according to claim 1, wherein the dehydration/condensation is performed using a dehydrating agent.

11. The method according to claim 10, wherein the amount of the dehydrating agent is in the range of 0.2 to 5 moles, per 1 mole of the compound (I-4).

12. A method of producing a compound represented by general formula (b1-1) shown below, comprising reacting a

What is claimed is:

1. A method of producing a compound represented by general formula (I-11) shown below, comprising subjecting a compound (I-3) represented by general formula (I-3) shown below and a compound (I-4) represented by general formula (I-4) shown below to dehydration/condensation in the presence of an acidic catalyst:

compound (I) represented by general formula (I) shown below with a compound (II) represented by general formula (II) shown below:

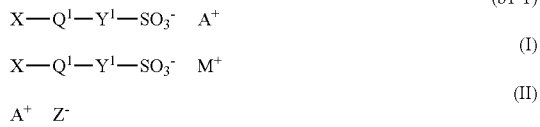

wherein $Q^1$ represents a divalent linking group or a single bond; $Y^1$ represents an alkylene group which may have a substituent or a fluorinated alkylene group which may have a substituent; X represents a cyclic group which forms a ring skeleton and comprises 3 to 30 carbon atoms which may have a substituent, and has a S atom of an —$SO_2$— group in the ring skeleton thereof; $A^+$ represents an organic cation; $M^+$ represents an alkali metal ion ; and $Z^-$ represents a low nucleophilic halogen ion, an ion which is capable of forming an acid exhibiting a lower acidity than the compound (I), $BF_4^-$, $AsF_6^-$, $SbF_6^-$, $PF_6^-$ or $ClO_4^-$.

13. The method according to claim 12, wherein $Z^-$ represents a halogen ion.

14. The method according to claim 12, wherein $Z^-$ represents a p-toluenesulfonic acid ion, a methanesulfonic acid ion, a benzenesulfonic acid ion or a trifluoromethanesulfonic acid ion.

15. The method according to claim 12, wherein reacting the compound (I) with the compound (II) is performed by dissolving the compound (I) and the compound (II) in a solvent selected from the group consisting of water, dichloromethane, acetonitrile, methanol, chloroform and methylene chloride, and stirring the resulting solution.

16. The method according to claim 12, wherein reacting the compound (I) with the compound (II) is performed at a temperature of 0° C. to 150° C.

17. The method according to claim 12, wherein reacting the compound (I) with the compound (II) is performed for 0.5 to 10 hours.

18. The method according to claim 12, the amount of the compound (II) is in the range of 0.5 to 2 moles, per 1 mole of the compound (I).

19. The method according to claim 13, wherein the halogen ion is a bromine ion.

* * * * *

UNITED STATES PATENT AND TRADEMARK OFFICE
CERTIFICATE OF CORRECTION

PATENT NO. : 8,124,313 B2
APPLICATION NO. : 12/692513
DATED : February 28, 2012
INVENTOR(S) : Takehiro Seshimo et al.

It is certified that error appears in the above-identified patent and that said Letters Patent is hereby corrected as shown below:

Title Page, (Item 73 Assignee) Line 2, Change "Kawaski-shi" to --Kawasaki-shi--.

In Column 2, Line 59 (Approx.), Change "Problem" to --Problems--.

In Column 4, Line 61, Change "$CH_2$—and" to --$CH_2$— and--.

In Column 5, Line 26, Change "prefe1" to --preferably 1--.

In Column 5, Line 27, After "example" delete "rably".

In Column 5, Line 27, Change "include" to --include —$CF_2$—,--.

In Column 5, Line 46, Change "include" to --include —$CF_2$—,--.

In Column 5, Line 53, Change "these," to --these, —$CF_2$—,--.

In Column 6, Line 51, Change "10.Examples" to --10. Examples--.

In Column 7, Line 1, Change "12.Here," to --12. Here,--.

In Column 13, Line 28 (Approx.), Change "1.As" to --1. As--.

In Column 13, Line 32 (Approx.), Change "1.It" to --1. It--.

In Column 18, Line 8 (Approx.), Change "formula" to --formula:--.

In Column 18, Lines 52-53, Change "tetracycicododecanyl" to --tetracyclododecanyl--.

In Column 25, Line 63 (Approx.), Change "(b'-1-16)," to --(b'-1-16)--.

In Column 30, Line 47 (Approx.), Change "(al"-6)" to --(a1"-6)--.

In Column 32, Line 61 (Approx.), Change "R'''" to --$R^{1'}$--.

In Column 74, Line 57, Change "(a-1-1-6)," to --(a1-1-6),--.

In Column 86, Line 66, Change "1 is" to --l is--.

In Column 87, Line 2, Change "1.When" to --1. When--.

In Column 87, Line 11 (Approx.), Change "norbonyl" to --norbornyl--.

In Column 87, Line 14, Change "1,1" to --1, 1--.

In Column 87, Line 16, Change "2-norbonyl" to --2-norbornyl--.

Signed and Sealed this
Twenty-first Day of August, 2012

David J. Kappos
*Director of the United States Patent and Trademark Office*

CERTIFICATE OF CORRECTION (continued)
U.S. Pat. No. 8,124,313 B2

In Column 87, Line 16, Change "3-norbonyl" to --3-norbornyl--.

In Column 87, Line 19 (Approx.), Change "norbonyl" to --norbornyl--.

In Column 89, Line 19, Change "20,000.By" to --20,000. By--.

In Column 89, Line 29, Change "2.5.Here," to --2.5. Here,--.

In Column 91, Line 33, After "group" insert --.--.

In Column 91, Line 53, Change "R3''" to --$R^3$"--.

In Column 91, Line 65, Change "$R^1$-," to --$R^1$",--.

In Column 94, Line 31 (Approx.), Change "$n_i$" to --$n_1$--.

In Column 96, Line 51, Change "phenantryl" to --phenanthryl--.

In Column 97, Line 34-35, Change "phenyl]acetonitrile," to --phenyl] acetonitrile,--.

In Column 97, Line 36, Change "phenyl]acetonitrile," to --phenyl] acetonitrile,--.

In Column 99, Line 38, Change "[4.3.01]-5" to --[4.3.0]-5--.

In Column 99, Line 38, Change "[5.4.01]-7" to --[5.4.0]-7--.

In Column 100, Lines 36-37, Change "y-butyrolactone;" to --γ-butyrolactone;--.

In Column 102, Line 23, Change "at it" to --as it--.

In Column 106, Line 20 (Approx.), Change "1h," to --1H,--.

In Column 107 (3rd Structure), Line 29 (Approx.), Change " 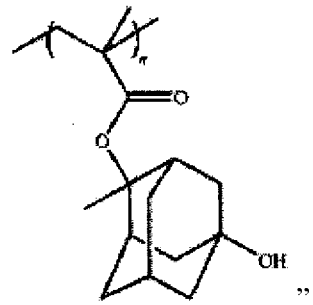 "

to -- 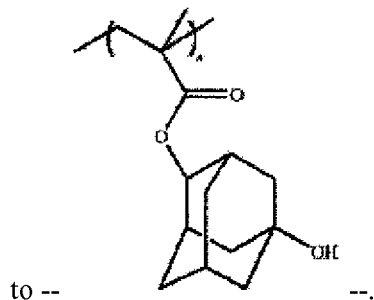 --.

In Column 107, Line 31 (Approx.), Change "Sensitivity]" to --sensitivity]--.

In Column 110, Line 50 (Approx.), Change "$(|E1-E2/Eop) \times 100$" to --$(|E1 - E2|/Eop) \times 100$--.

In Column 111, Line 32, Change "1L" to --1 L--.

In Column 112, Line 4, Change "($H^b$)," to --($H^b$)),--.

In Column 112, Line 4, Change "($H^c$)," to --($H^c$)),--.

In Column 112, Line 5, Change "($H^e$)." to --($H^e$)).--.

In Column 112, Line 45 (Approx.), Change " 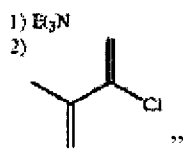 " to -- 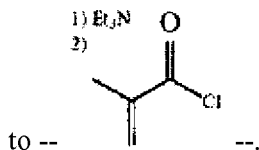 --.

In Column 112, Line 55 (Approx.), Change " 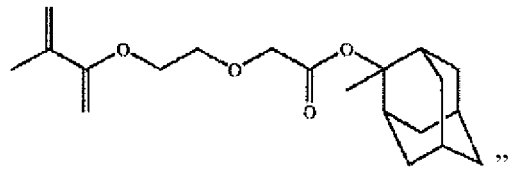 " to -- 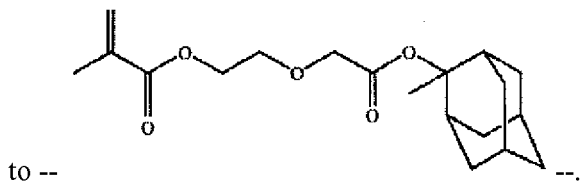 --.

In Column 112, Line 66 (Approx.), Change "(H$^e$))," to --(H$^e$)),--.

In Column 113, Line 57, Change "1/m/" to --l/m/--.

In Column 115, Line 33 (Approx.), Change "Sensitivity]" to --sensitivity]--.

In Column 116, Line 18 (Approx.), Change "(|E1–E2/Eop)×100" to --(|E1 - E2|/Eop) × 100--.

In Column 116, Line 61, Change "δ(ppm) -107.8" to --δ(ppm)-107.8--.

In Column 117, Line 59 (Approx.), Change "CH3)," to --CH$_3$),--.

In Column 117, Line 60 (Approx.), Change "CH$_2$,3H," to --CH$_2$, 3H,--.

In Column 120, Line 53 (Approx.), Change "HC1," to --HCl,--.

In Column 120, Line 59, Change "δ(ppm) 1.73-1.96" to --δ(ppm)=1.73-1.96--.

In Column 121, Line 47, Change "δ(ppm) 1.74-1.96" to --δ(ppm)=1.74-1.96--.

In Column 121, Line 49, Change "1H)," to --1H,--.

In Column 122, Line 25, Change "HC1," to --HCl,--.

In Column 122, Line 30, Change "δ(ppm) 1.74-2.01" to --δ(ppm)=1.74-2.01--.

In Column 123, Line 10 (Approx.), Change "δ(ppm) 1.74-1.96" to --δ(ppm)=1.74-1.96--.

In Column 123, Line 16 (Approx.), Change "SO3CF$_2$)," to --SO$_3$CF$_2$),--.

In Column 123, Line 17 (Approx.), Change "CH$_2$CH$_2$)," to --CH$_2$CF$_2$),--.

In Column 123, Line 20 (Approx.), Change "(l')" to --(1')--.

In Column 124, Line 7, Change "δ(ppm) 0.82" to --δ(ppm)=0.82--.

In Column 125, Line 8 (Approx.), Change "δ(ppm) 1.74-1.96" to --δ(ppm)=1.74-1.96--.

In Column 127, Line 19, In Claim 12, change "ion ;" to --ion;--.